(12) United States Patent
Kim et al.

(10) Patent No.: US 10,400,022 B2
(45) Date of Patent: Sep. 3, 2019

(54) NEUROPILIN-1 SPECIFIC BINDING PEPTIDE, FUSION PROTEIN FUSED WITH SAME, AND USE THEREOF

(71) Applicant: AJOU UNIVERSITY INDUSTRY-ACADEMIC COOPERATION FOUNDATION, Suwon-si, Gyeonggi-do (KR)

(72) Inventors: Yong Sung Kim, Suwon-si (KR); Ye Jin Kim, Busan (KR)

(73) Assignee: Ajou University Industry-Academic Cooperation Foundation, Suwon-si, Gyeonggi-do (KR)

( * ) Notice: Subject to any disclaimer, the term of this patent is extended or adjusted under 35 U.S.C. 154(b) by 0 days.

(21) Appl. No.: 15/560,232

(22) PCT Filed: Mar. 23, 2016

(86) PCT No.: PCT/KR2016/002942
§ 371 (c)(1),
(2) Date: Sep. 21, 2017

(87) PCT Pub. No.: WO2016/153276
PCT Pub. Date: Sep. 29, 2016

(65) Prior Publication Data
US 2018/0051064 A1    Feb. 22, 2018

(30) Foreign Application Priority Data

Mar. 23, 2015    (KR) .................. 10-2015-0040164

(51) Int. Cl.
| | | |
|---|---|---|
| *C07K 14/705* | (2006.01) | |
| *A61K 9/127* | (2006.01) | |
| *G01N 33/574* | (2006.01) | |
| *G01N 33/68* | (2006.01) | |
| *C07K 19/00* | (2006.01) | |
| *G01N 33/53* | (2006.01) | |
| *A61K 47/50* | (2017.01) | |
| *A61K 38/00* | (2006.01) | |

(52) U.S. Cl.
CPC ........... *C07K 14/705* (2013.01); *A61K 9/127* (2013.01); *A61K 47/50* (2017.08); *C07K 19/00* (2013.01); *G01N 33/53* (2013.01); *G01N 33/57492* (2013.01); *G01N 33/6845* (2013.01); *G01N 33/6872* (2013.01); *G01N 33/6893* (2013.01); *A61K 38/00* (2013.01); *C07K 2317/52* (2013.01); *C07K 2317/522* (2013.01); *C07K 2317/524* (2013.01); *C07K 2317/526* (2013.01); *C07K 2317/55* (2013.01); *C07K 2317/56* (2013.01); *C07K 2317/622* (2013.01); *C07K 2319/30* (2013.01); *G01N 2333/70596* (2013.01); *G01N 2800/7014* (2013.01)

(58) Field of Classification Search
CPC ........ A61K 38/00; A61K 47/50; A61K 9/127; C07K 14/705; C07K 19/00; C07K 2317/52; C07K 2317/522; C07K 2317/524; C07K 2317/526; C07K 2317/55; C07K 2317/56; C07K 2317/622; C07K 2319/30; G01N 2333/70596; G01N 2800/7014; G01N 33/53; G01N 33/57492; G01N 33/6845; G01N 33/6872; G01N 33/6893
See application file for complete search history.

(56) References Cited

U.S. PATENT DOCUMENTS

| | | | | |
|---|---|---|---|---|
| 2007/0087001 A1* | 4/2007 | Taylor | ................. | C07K 16/22 424/145.1 |
| 2013/0121915 A1* | 5/2013 | Paas | ................. | B82Y 5/00 424/9.1 |

FOREIGN PATENT DOCUMENTS

| | | | | |
|---|---|---|---|---|
| JP | 2010-511397 A | 4/2010 | | |
| JP | 2011514160 A | 5/2011 | | |
| JP | 2012530787 A | 12/2012 | | |
| KR | 10-2014-0138539 A | 12/2014 | | |
| WO | WO-03029275 A2 * | 4/2003 | ........... | C07K 14/001 |

(Continued)

OTHER PUBLICATIONS

Mechanisms of Carcinogenesis, section 3, 2008, International Agency for research on cancer.*

(Continued)

*Primary Examiner* — Rachael E Bredefeld
*Assistant Examiner* — Erinne R Dabkowski
(74) *Attorney, Agent, or Firm* — Mintz Levin Cohn Ferris Glovsky and Popeo, P.C.; Kongsik Kim

(57) ABSTRACT

A peptide that binds specifically to neuropilin-1 (NRP1) without binding to neuropilin-2 (NRP2) is provided. A fusion protein, a fusion antibody, small-molecule drug, a nanoparticle, or a liposome, which comprises the peptide, and a pharmaceutical composition for treating or preventing cancer or angiogenesis-related diseases, and a composition for diagnosing cancer or angiogenesis-related diseases are provided. A polynucleotide encoding the peptide that binds specifically to NRP1 and a method for screening the peptide that binds specifically to NRP1 are provided. An antibody heavy-chain constant region Fc-fused peptide binding specifically to NRP1 has the property of binding specifically to NRP1, and thus when it is administered in vivo, it accumulates selectively in tumor tissue, and widens the intercellular space between tumor-associated endothelial cells to promote its extravasation and increases its tumor tissue penetration.

22 Claims, 35 Drawing Sheets
(26 of 35 Drawing Sheet(s) Filed in Color)
Specification includes a Sequence Listing.

(56) References Cited

FOREIGN PATENT DOCUMENTS

| WO | 2009/050691 A2 | 4/2009 |
|---|---|---|
| WO | 2014/189303 A1 | 11/2014 |

OTHER PUBLICATIONS

Belal Chaudhary, Neuropilin 1: function and therapeutic potential in cancer, Cancer Immunol Immunother (2014) 63:81-99.*

Andrew M. Scott et al., "Antibody therapy of cancer", Nature Reviews | Cancer, Apr. 2012, pp. 278-287, vol. 12.

Rebecca L. Vega Thurber et al., "Metagenomic analysis indicates that stressors induce production of herpes-like viruses in the coral Porites compressa", PNAS, Nov. 25, 2008, pp. 18413-18418, vol. 105, No. 47.

Virginia S Baker et al., "Cytokine-associated neutrophil extracellular traps and antinuclear antibodies in Plasmodium falciparum infected children under six years of age", Malaria Journal, 2008, pp. 1-12, vol. 7, No. 41.

Thomas M. Behr et al., "Reducing the renal uptake of radiolabeled antibody fragments and peptides for diagnosis and therapy: present status, future prospects and limitations", European Journal of Nuclear Medicine, Feb. 1998, pp. 201-212, vol. 25, No. 2.

Mark S. Dennis et al., "Imaging Tumors with an Albumin-Binding Fab, a Novel Tumor-Targeting Agent", Cancer Res, Jan. 1, 2007, pp. 254-261, vol. 67, No. 1.

Fabrizio Marcucci et al., "Improving drug uptake and penetration into tumors: current and forthcoming opportunities", Frontiers in Oncology | Pharmacology of Anti-Cancer Drugs, Jun. 2013, pp. 1-3, vol. 3, Article 161.

M.P. Hofmann et al., "High-strength resorbable brushite bone cement with controlled drug-releasing capabilities", Acta Biomaterialia, 2009, pp. 43-49, vol. 5.

Live Eikenes et al., "Collagenase Increases the Transcapillary Pressure Gradient and Improves the Uptake and Distribution of Monoclonal Antibodies in Human Osteosarcoma Xenografts", Cancer Research, Jul. 15, 2004, pp. 4768-4773, vol. 64.

Ines Beyer et al., "Epithelial Junction Opener JO-1 Improves Monoclonal Antibody Therapy of Cancer", Cancer Res, Nov. 15, 2011, pp. 7080-7090, vol. 71, No. 22.

Kazuki N. Sugahara et al., "Coadministration of a Tumor-Penetrating Peptide Enhances the Efficacy of Cancer Drugs", Science, May 21, 2010, pp. 1031-1035, vol. 328.

Alex L. Kolodkin et al., "Neuropilin Is a Semaphorin III Receptor", Cell, Aug. 22, 1997, pp. 753-762, vol. 90.

Brent A Appleton et al., "Structural studies of neuropilin/antibody complexes provide insights into semaphorin and VEGF binding", The EMBO Journal, 2007, pp. 4902-4912, vol. 26.

Qi Pan et al., "Blocking Neuropilin-1 Function Has an Additive Effect with Anti-VEGF to Inhibit Tumor Growth", Cancer Cell, Jan. 2007, pp. 53-67, vol. 11.

Maresa Caunt et al., "Blocking Neuropilin-2 Function Inhibits Tumor Cell Metastasis", Cancer Cell, Apr. 2008, pp. 331-342, vol. 13.

Matthew W. Parker et al., "Mechanism of Selective VEGF-A Binding by Neuropilin-1 Reveals a Basis for Specific Ligand Inhibition", PLOS ONE, Nov. 2012, pp. 1-7, vol. 7, No. 11, e49177.

David Zanuy et al., "Sequence dependence of C-end rule peptides in binding and activation of neuropilin-1 receptor", Journal of Structural Biology, 2013, pp. 78-86, vol. 182.

David W. Colby et al., "Engineering Antibody Affinity by Yeast Surface Display", Methods in Enzymology, 2004, pp. 348-358, vol. 388.

Camille Grandclement et al, "Neuropilin-2 Expression Promotes TGF-b1-Mediated Epithelial to Mesenchymal Transition in Colorectal Cancer Cells", PLoS ONE, Jul. 2011, pp. 1-14, vol. 6, Issue 7, e20444.

Tambet Teesalu et al., "Tumor-penetrating peptides", Frontiers in Oncology | Pharmacology of Anti-Cancer Drugs, Aug. 2013, pp. 1-8, vol. 3, Article 216.

Tambet Teesalu et al., "C-end rule peptides mediate neuropilin-1-dependent cell, vascular, and tissue penetration", PNAS, Sep. 22, 2009, pp. 16157-16162, vol. 106, No. 38.

Tae-Hwan Shin et al., "Enhancement of the Tumor Penetration of Monoclonal Antibody by Fusion of a Neuropilin-Targeting Peptide Improves the Antitumor Efficacy", Molecular Cancer Therapeutics, Mar. 2014, pp. 651-661, vol. 13, No. 3.

International Search Report of PCT/KR2016/002942 dated Jun. 16, 2016 [PCT/ISA/210].

Hanae Ueyama et al., "Semaphorin 3A lytic hybrid peptide binding to neuropilin-1 as a novel anti-cancer agent in pancreatic cancer", Biochemical and Biophysical Research Communications, vol. 414, No. 1, Sep. 14, 2011 (Sep. 14, 2011), pp. 60-66, XP028316371 (7 pages total).

Claus Christensen et al., "Proteolytic processing converts the repelling signal Sema3E into an inducer of invasive growth and lung metastasis", Cancer Research, American Association for Cancer Research, US, vol. 65, No. 14, Jul. 15, 2005 (Jul. 15, 2005), pp. 6167-6177, XP002522809 (11 pages total).

G Neufeld et al., "Semaphorins in cancer", Frontiers in Bioscience, Albertson, NY, US, vol. 10, Jan. 1, 2005 (Jan. 1, 2005), pp. 751-760, XP002657015 (10 pages total).

European Patent Office; communication dated Aug. 6, 2018 issued in counterpart application No. 16769094.0.

Wronski, et al., "Tuftsin Binds Neuropilin-1 through a Sequence Similar to That Encoded by Exon 8 of Vascular Endothelial Growth Factor*", The Journal of Biological Chemistry, Mar. 3, 2006, vol. 281, No. 9, pp. 5702-5710.

Parker, et al., "Structural Basis for Selective Vascular Endothelial Growth Factor-A (VEGF-A) Binding to Neuropilin-1*", The Journal of Biological Chemistry, 2012, vol. 287, No. 14, Mar. 30, 2012, pp. 11082-11089.

Ce'Be-Suarez, et al., "Orf virus VEGF-E NZ2 promotes paracellular NRP-1/VEGFR-2 coreceptor assembly via the peptide RPPR", The FASEB Journal, Aug. 2008, vol. 22, pp. 3078-3086.

Communication dated Oct. 23, 2018, from Japanese Patent Office from counterpart application No. 2017-549504.

* cited by examiner

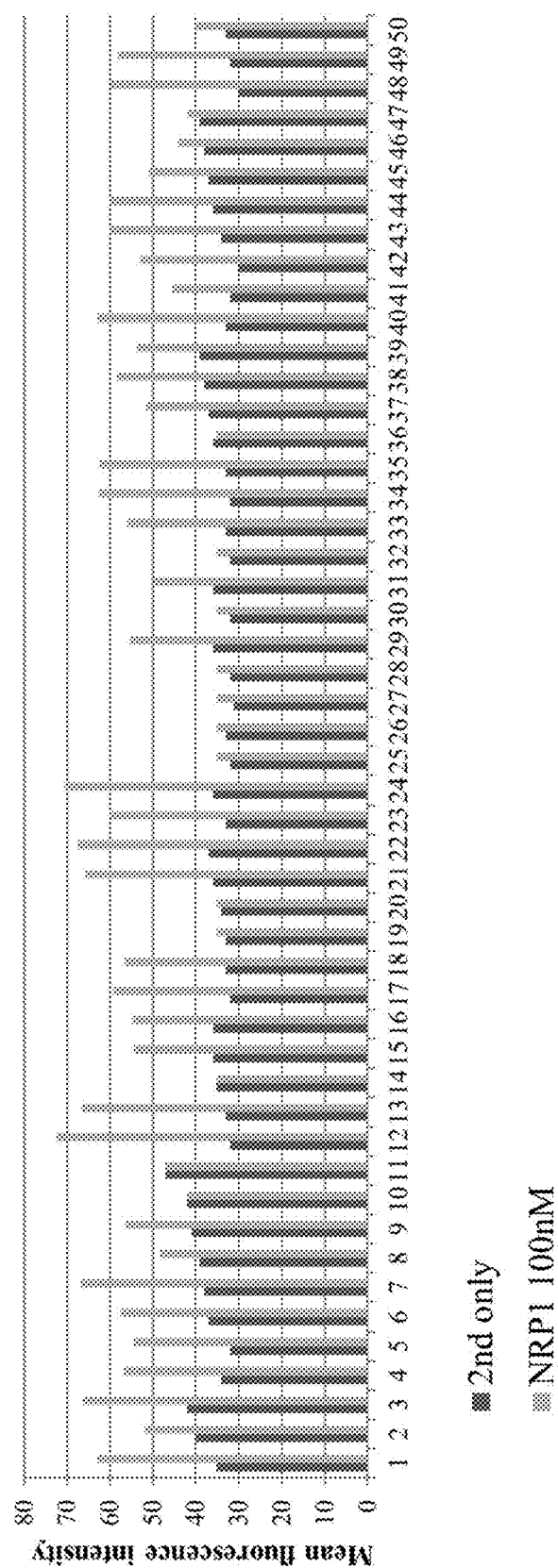

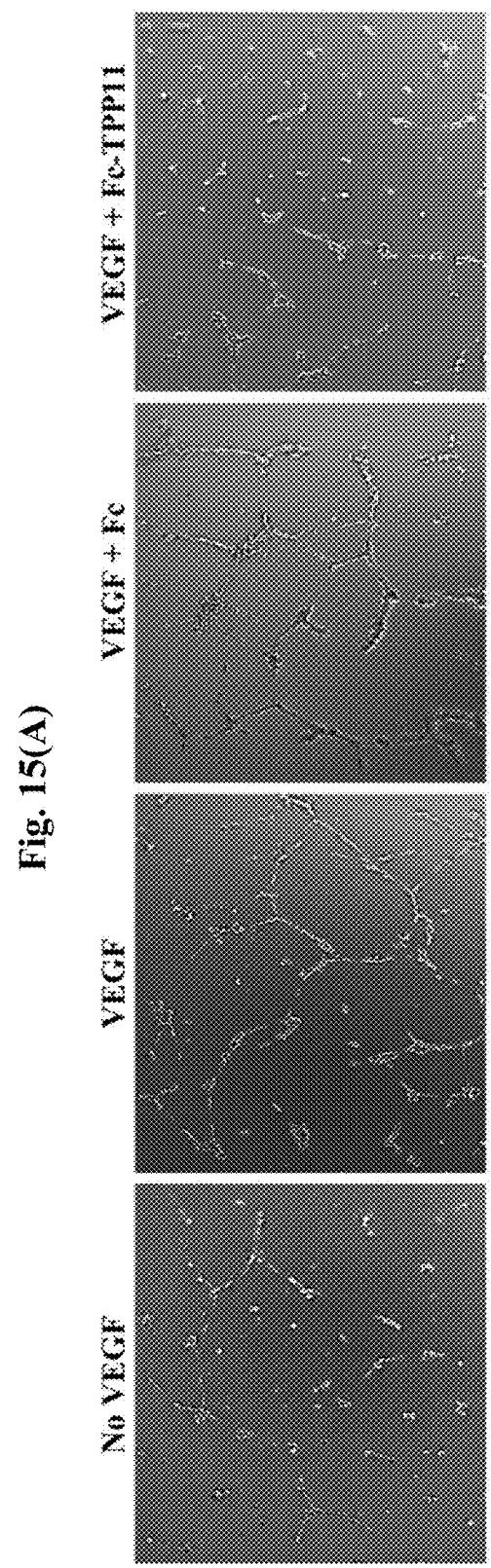

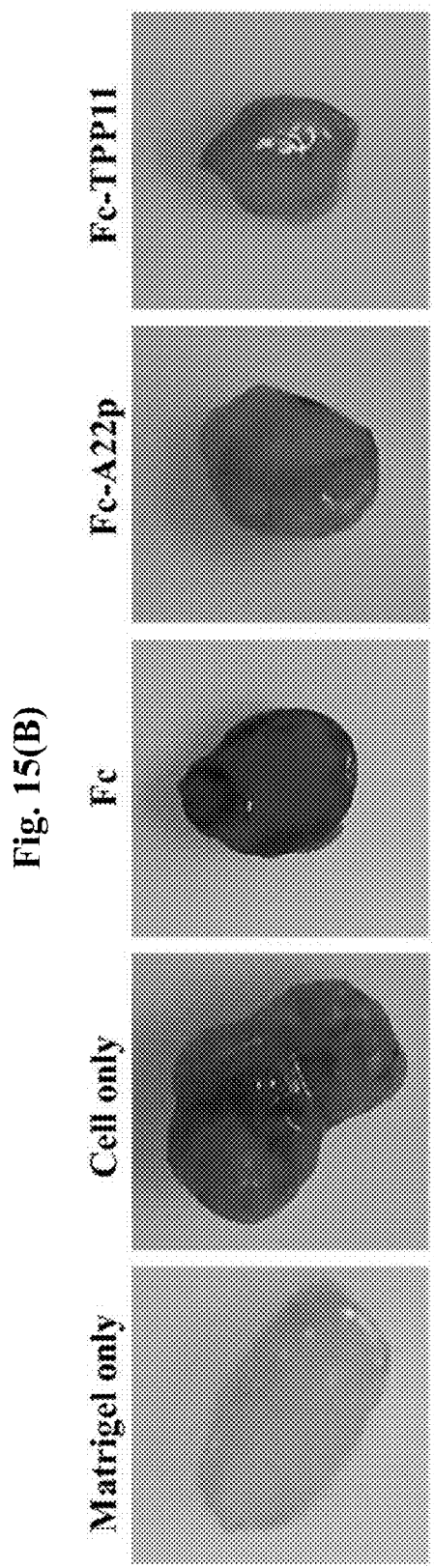

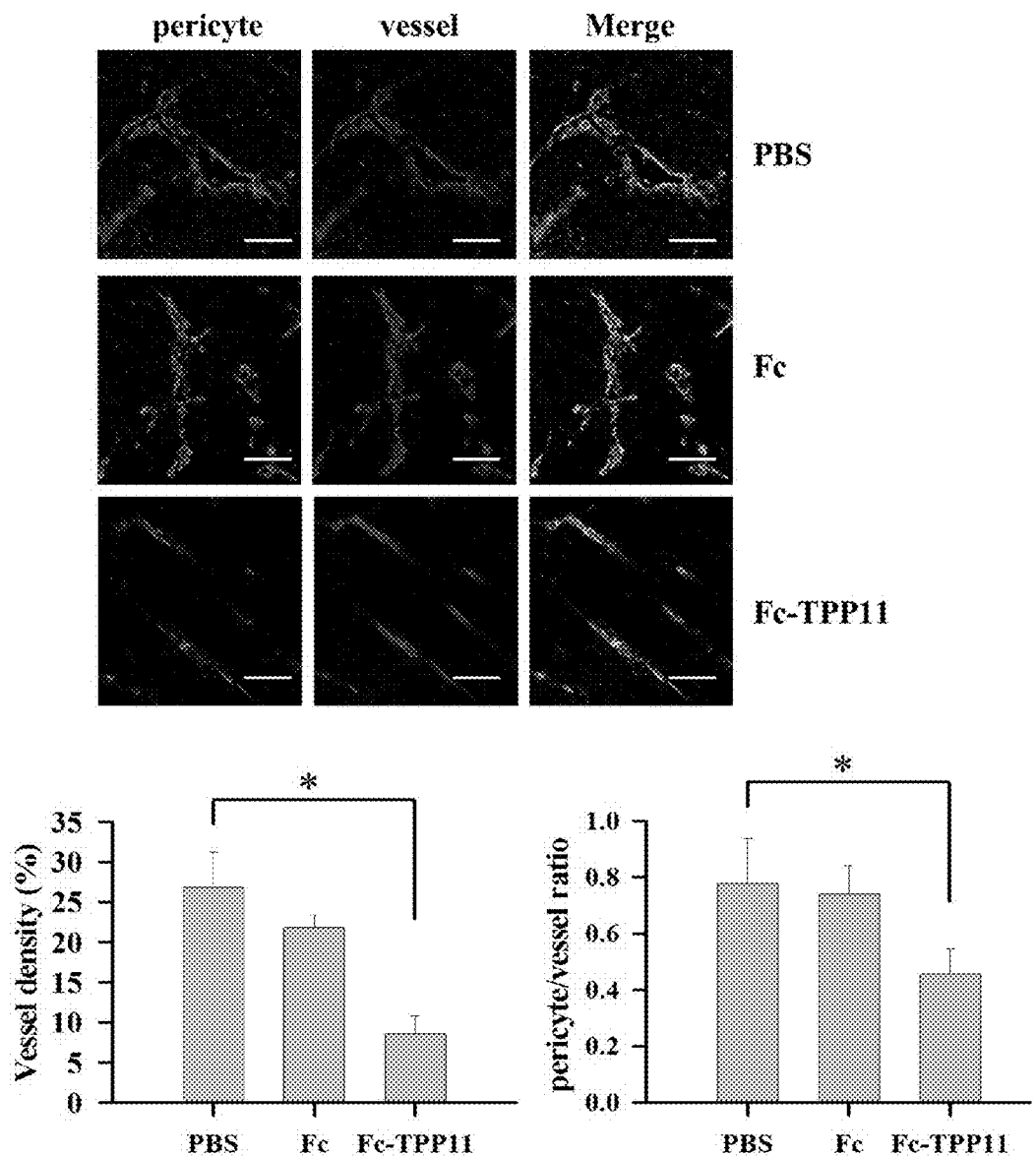

Cetuximab-TPP11

NEUROPILIN-1 SPECIFIC BINDING PEPTIDE, FUSION PROTEIN FUSED WITH SAME, AND USE THEREOF

CROSS REFERENCE TO RELATED APPLICATIONS

This application is a National Stage of International Application No. PCT/KR2016/002942, filed Mar. 23, 2016, claiming priority based on Korean Patent Application No. 10-2015-0040164, filed Mar. 23, 2015, the contents of all of which are incorporated herein by reference in their entirety.

TECHNICAL FIELD

The present disclosure relates to a tumor-penetrating peptide (TPP) that binds specifically to neuropilin-1 (NRP1). Specifically, the peptide of the present disclosure is a peptide that binds specifically only to NRP1 with high affinity, which is screened from a library constructed on the basis of peptide that bind to both neuropilin-1 (NRP1) and neuropilin-2 (NRP2).

Moreover, the present disclosure relates to a fusion protein, a fusion antibody, a small-molecule drug, a nanoparticle or a liposome, which the above-described peptide that binds specifically to NRP1 is fused thereto.

In addition, the present disclosure relates to a polynucleotide that encodes the above-described peptide binding specifically to NRP1.

In addition, the present disclosure relates to a pharmaceutical composition for treating or preventing cancer or angiogenesis-related diseases, comprises: the above-described peptide binding specifically to NRP1; or a fusion protein, a fusion antibody, a small-molecule drug, a nanoparticle or a liposome, which the above-described peptide that binds specifically to NRP1 is fused thereto.

In addition, the present disclosure relates to a composition for diagnosing cancer or angiogenesis-related diseases, comprises: the above-described peptide binding specifically to NRP1; or a fusion protein, a small-molecule drug, a nanoparticle or a liposome, which the above-described peptide that binds specifically to NRP1 is fused thereto.

In addition, the present disclosure relates to a method for selecting peptide that binds specifically to NRP1 comprising constructing a yeast surface-displayed immunoglobulin Fc-fused peptide library.

BACKGROUND ART

Antibody is a protein that binds to an antigen with high specificity and high affinity to neutralize the antigen. Furthermore, the antibody has antibody-dependent cellular cytotoxicity and complement-dependent cellular cytotoxicity, which are the functions of the heavy-chain constant region thereof, and has a long serum half-life by binding to FcRn (neonatal Fc receptor). Due to the property of binding to an antigen with high specificity and high affinity, undesirable side effects can be reduced, and due to antibody-dependent cellular cytotoxicity and complement-dependent cellular cytotoxicity, the antibody can induce apoptosis of disease-causing cells, and the long serum half-life of the antibody enables the long-lasting effects of the antibody. Because of such properties of the antibody, studies have been actively conducted to develop the antibody into therapeutic proteins.

Cancer therapeutic antibodies developed to date are divided into two categories: antibodies for treatment of solid tumors; and antibodies for treatment of blood cancer (leukemia/lymphoma). According to the single administration of the antibodies in each category, the two antibodies show different response rates. When referring to statistics of several commercially available antibodies, in case where a single administration of an antibody for treatment of blood cancer, the response rate reaches 30 to 51%, whereas in case where a single administration of an antibody for treatment of solid tumors, the response rate is 8 to 15%, which is relatively low. This is because the antibody for treatment of blood cancer targets cancer cells in blood, whereas the antibody for treatment of solid tumors should be subjected to the following processes in order to exhibit its therapeutic effects: 1) reaching tumor blood vessels in solid tumor tissue through blood vessels after systemic intravenous injection or subcutaneous injection (tumor homing step); 2) flowing out from tumor blood vessels toward tumor tissue (extravasation step); 3) penetrating into vessel-free tissue even in tumor tissue (tumor tissue penetration step); and 4) binding to an antigen expressed in tumor cells and acting on the antigen (targeted antigen binding & effector function step) (Scott A M et al. 2012). In such series of processes, various factors are present which interfere with tumor tissue accumulation, and penetration into tumor tissue of the solid tumor therapeutic antibody, which leads an arrival of the antibody at tumor cells in the tumor tissue. For this reason, the amount of antibody that is accumulated to the tumor tissues in human body is very small (0.01 to 0.0001% of injected dose per gram tumor tissue), and thus the antibody shows a low response rate (Thurber et al. 2008). Accordingly, the development of antibody technology that enables an antibody to be accumulated selectively in tumor tissue and to have a high ability to penetrate tumor tissue makes it possible to increase the therapeutic effect of a solid tumor therapeutic antibody, and thus is very important.

There are two major reasons that an antibody has a deficiency in penetrating tissue: 1) intrinsic properties of the antibody (size (~150 kDa), antigen-binding barrier, etc.) (Thurber and Dane Wittrup, 2012), and 2) microstructural/physiological properties of tumor tissue (e.g., incomplete and abnormal angiogenesis, very low lymphatic gland formation, high cellular density, high extracellular density, etc.), which differ from those of normal tissue (Jain and Stylianopoulos, 2010). Thus, efforts have been made to increase the tumor tissue penetrability of antibodies by use of various methods, including an antibody engineering technique that regulates the size and antigen binding specificity of antibodies, or a method of combination administration an antibody with a molecule (i.e., promoter agent) that promotes the tumor tissue penetration of the antibody.

Antibodies in blood are hardly delivered to tumor tissue by diffusion or convection, because the antibody is a 150-kDa large molecule consisting of 12 domains (Baker et al. 2008). To overcome this difficulty, there has been an attempt to administer antibody fragments alone, such as an antigen-binding fragment (Fab) (50 kDa), a single-chain variable fragment (scFv) (30 kDa), and a heavy-chain variable domain (VH) (14 kDa), which have reduced sizes. However, the antibody fragment has no Fc fragment and is small in size, and for this reason, when it is administered in vivo, it is released in large amounts through the kidneys to reduce the half-life thereof, indicating that the efficacy of the antibody is not significantly improved (Behr et al. 1998).

Another reason why an antibody is not distributed in a large amount in tissue is an antigen-binding capability of the antibody. An antibody for treatment of solid tumors is overexpressed on a tumor-associated antigen or in a tumor, and has a high affinity for a target which is important for tumor growth. Even when the antibody may reach the tissue where a specific antigen is present, in a tumor tissue composed of cells with a great amount of antigen expression, the antibody is stayed on the surface of the tumor tissue while binding to an antigen expressed in cells on the tumor tissue surface, due to its high affinity (Lee and Tannock, 2010). After binding to the antigen, the antibody is endocytosed, i.e., penetrates into the cells along with the antigen and is degraded in the cells. In other words, the antibody may be located on the tumor tissue surface, but is degraded after binding to an overexpressed tumor antigen, and thus does not efficiently penetrate the tumor tissue. Accordingly, the antibody cannot reach a tumor cell antigen in a tissue distant from tumor blood vessels, and thus the anti-tumor activity of antibody may decrease, and antibody resistance and tumor recurrence may be induced. To overcome this shortcoming, studies have been conducted to regulate antibody affinity or increase antibody half-life (Dennis et al. 2007).

The physiological properties of tumor tissue, which interfere with the penetration and distribution of antibodies in tumor tissue, can be largely classified into four cases: endothelial barrier; high tumor interstitial fluid pressure; stromal impediment; and epithelial barrier.

As for the endothelial barrier, a tumor overexpresses and secretes a pro-angiogenic factor that promotes the growth of vascular endothelial cells located around blood vessels, in order to receive large amounts of nutrients due to its rapid growth rate. Accordingly, a large amount of new blood vessels are non-uniformly produced to reduce the overall blood flow rate. In an attempt to overcome this shortcoming, there has been proposed a method of increasing extravasation to enable a therapeutic agent to flow out from blood vessels so as to be distributed to tissue. Furthermore, a case has been reported in which TNF-α and IL-2, which are pro-inflammatory cytokines associated with extravasation, a promoter chemical drug that promotes extravasation, and a therapeutic agent were co-administered to promote drug to tumor tissue (Marcucci et al. 2013). However, these attempts are difficult to be commercialized and clinically experimented in that it is required to produce two substances such as antibody and extravasation promoter.

High tumor interstitial fluid pressure results from a situation where a pressure difference allowing a drug to be convected from a blood vessel to tissue is small, or where the fluid pressure of tissue is higher than that of blood. High tumor interstitial fluid pressure is mainly caused due to the accumulation of interstitial fluid pressure in the absence of a lymphatic duct in tumor tissue, unlike in normal tissue, and also contributes to abnormal angiogenesis. In an attempt to overcome this, there has been proposed a method of inhibiting the activity of a factor promoting the growth of vascular endothelial cell, particularly vascular endothelial cell growth factor-A (VEGF165A), to inhibit angiogenesis to normalize the blood vessel, or a method of increasing the fluid pressure of blood vessel. With regard to the method of increasing the fluid pressure of blood vessel, a case has been reported in which the plasma protein albumin was administered in combination with an antibody to increase the osmotic pressure of blood vessels, thereby enhancing delivery of the antibody to tumor tissue (Hofmann et al. 2009).

The stromal impediment is an extracellular matrix barrier that an antibody meets when being convected to tissue after flowing out from micro-vessels. The stromal impediment mainly consists of collagen and hyaluronan. The extracellular matrix greatly affects the shape of tumor. Accordingly, there is a great difference between an area where a drug is well distributed and an area where the drug is not well distributed, and thus drug distribution becomes non-uniform. Additionally, as the expression level of extracellular matrix increases, the tumor interstitial fluid pressure increases due to high cell density with solid tumor stress (solid stress). In an attempt to overcome this limitation, there has been a method of inducing apoptosis of tumor tissue cells to reduce cell density in tumor tissue. Additionally, there has been reported an example in which solid stress was reduced by treatment with collagenase degrading collagen of tumor tissue, thereby increasing drug delivery about twice compared to a control group (Eikenes et al. 2004).

In the epithelial barrier, intercellular adhesion factors of interstitial epithelial cells in tumor tissue densely fill up an intercellular space, and thus they prevent a therapeutic agent from being diffused and convected between the cells. E-cadherin is well known as a main factor of the intercellular adhesion. Since a substance that reduces E-cadherin was found in virus (adenovirus-3), a case has been reported in which only a portion (JO-1) having an activity of reducing cellular E-cadherin, among proteins constituting the virus, was co-administered with an antibody, thereby increasing the anti-cancer effect of the antibody (Beyer et al. 2011).

In addition, there have been proposed methods in which a peptide that binds to neuropilin (NRP) that is overexpressed in tumor-associated endothelial cells and tumor cells is used to enhance antibody penetration into tumor tissue. One of the methods that use the neuropilin-binding peptide is to co-administer an iRGD peptide with an antibody (Sugahara et al. 2010). However, in the case of the method of co-administering the peptide, the amount and frequency of peptide that is actually administered to a patient should be very large due to pharmacokinetics attributable to the small molecular size of the peptide. Furthermore, the industrial feasibility of the method is low, because a therapeutic agent and a tumor-penetrating peptide are separately produced due to an inevitable process of co-administration. In recent technologies to overcome this limitation, there has been an example in which an A22p peptide that binds to neuropilin is fused to the heavy-chain C-terminus of a monoclonal antibody, so that the long half-life of the antibody will be maintained and tumor tissue penetration of the antibody will be enhanced (Shin et al. 2014; Korean Patent Application No. 10-2014-0061751; and PCT Patent Application No. PCT/KR2014/004571).

Neuropilin, a transmembrane glycoprotein, is divided into two types: neuropilin-1 (NRP1) and neuropilin-1 (NRP2) (Kolodkin et al. 1997). Neuropilin-1 and -2 consist of 923 and 931 amino acids, respectively, and show an amino acid sequence homology of about 44%, and share several structural aspects and biological activities. Neuropilin-1 and 2 consist commonly of extracellular a1, a2, b1, b2 and MAM domains and an intracellular PDZ-binding domain (Appleton et al. 2007). Neuropilin is very weakly expressed in normal cells, but is overexpressed in most tumor-associated endothelial cells, solid tumor cells and blood tumor cells (Grandclement, C. and C. Borg 2011). Neuropilin acts as a co-receptor of VEGF receptors (VEGFRs) by binding to VEGF family ligands. Particularly, NRP1 acts as a co-receptor of VEGFR1, VEGFR2 and VEGFR3 to bind to various VEGF ligands, thereby contributing to angiogenesis, cell migration & adhesion and invasion. On the other hand, NRP2 acts as a co-receptor of VEGFR2 and VEGFR3, thereby contributing to lymphangiogenesis and cell adhesion. Furthermore, neuropilin 1 and 2 act as a co-receptor of plexin family receptors to bind to secreted class-3 semaphorin ligands (Sema3A, Sema3B, Sema3C, Sema3D, Sema3E, Sema3F, Sema3G). Since neuropilin has no domain in functional cells, it has no activity by itself, even if a ligand is binding thereto. It is known that neuropilin signal transduction occurs through VEGF receptor, which is a co-receptor, or through plexin co-receptor. Sema3 binds to neuropilin and plexin receptor at a ratio of 2:2:2 and acts. However, many study results show that neuropilin protein alone can perform signal transduction without its interaction with the VEGF receptor or plexin co-receptor. However, an exact molecular mechanism for this signal transduction is still unclear.

Cases have been reported in which the activities of neuropilin and co-receptor are inhibited even when only neuropilin is targeted. For example, it has been reported that anti-neuropilin-1 antibody binds to only neuropilin-1 competitively with VEGF-A known to bind to VEGFR2 and neuropilin-1, and functions to inhibit angiogenesis, cell survival, migration & adhesion and invasion, which are the actions of VEGFR2 (Pan Q et al. 2007). It has been reported that anti-neuropilin-2 antibody binds to neuropilin-2 competitively with VEGF-C known to binds to both VEGFR3 and neuropilin-2, and functions to inhibit lymphangiogenesis and cell adhesion, which are the operations of VEGFR3 (Caunt M et al. 2008).

The C-terminal region of each of the VEGF ligand family and Sema3 ligands, which bind to neuropilin 1 and 2, binds to the VEGF-binding sites (so-called arginine-binding pocket) in the b1 domain present commonly in neuropilin 1 and 2 (MW Parker et al. 2012). Herein, binding to the arginine-binding pocket occurs by a motif of R/K-x-x-R/K (R=arginine, K=lysine, and x=any amino acids), which is present commonly in the C-terminal region of neuropilin binding ligands. When mutation is induced with an amino acid sequence deviating from the motif, the ligands have a reduced binding affinity for neuropilin or do not bind to neuropilin, and thus lose their biological activity. Particularly, cationic arginine (Arg) or lysine (Lys) in the C-terminal region is essential for binding, and thus when it is substituted with another amino acid residue, the ligand loses its binding affinity for neuropilin, and loses its biological activity. Accordingly, the necessity of the R/K-x-x-R/K motif in the C-terminal region of such neuropilin binding ligands is called "C-end rule" (CendR) (Teesalu et al. 2009). A protein or peptide containing a C-end rule sequence is capable of binding to neuropilin by the C-terminal arginine (Arg) or lysine (Lys) residue (Zanuy et al, 2013).

The C-terminal regions of VEGF ligands and Sema3 ligands commonly have the R/K-x-x-R/K motif, and thus most of the ligands have the property of binding to both neuropilin 1 and 2 rather than binding selectively to any one of neuropilin 1 and 2.

In addition to ligands that bind to neuropilin 1 and 2, many peptides that bind to neuropilin have been selected or designed and reported. These peptides all have the R/K-x-x-R/K motif, and thus appear to bind to the arginine-binding pocket in the b1 domain of neuropilin 1 and 2. Furthermore, an iRGD peptide (Sugahara et al. 2010) that binds to neuropilin 1 and 2 to increase tumor tissue penetration of a co-administered drug, and an A22p peptide (Shin et al. 2014) that is fused to the heavy-chain end of an antibody to increase tumor tissue penetration of the antibody, also have amino acid sequences, following the CendR rule.

With respect to the peptides that bind to neuropilin, a peptide that binds specifically to any one of neuropilin 1 and 2 has not been reported, and these peptides have the CendR sequence motif, and thus bind to the arginine-binding pocket of both neuropilin 1 and 2.

As described above, neuropilin-1 is overexpressed only in newly formed blood vessels and plays an important role in angiogenesis, and neuropilin-2 is expressed in lymphatic vessels and contributes to lymphatic vessel production. Thus, a peptide that binds specifically to neuropilin-1 or neuropilin-2 with high affinity may have the capability to specifically regulate the biological activity of each neuropilin, but has not yet been reported. Furthermore, neuropilin 1 and 2 are activated as a homodimer or a heterodimer, and conventional peptides have been developed as monomeric peptides that have a very weak ability to regulate biological activity. Thus, a peptide that binds neuropilin-1 as a homodimer to regulate the biological activity of neuropilin-1 is preferred. Moreover, neuropilin-1 is overexpressed in endothelial cells and is stimulated by VEGF ligands, and thus plays an important role in angiogenesis. Accordingly, a peptide, which binds to only neuropilin-1 with high specificity and high affinity competitively with VEGF ligands, may have the ability to home and accumulate in tumor tissue and to inhibit angiogenesis. Furthermore, neuropilin-1 is overexpressed in tumor tissue blood vessels and tumor cells (epithelial cells) and stimulated by VEGF ligands, and thus plays an important role in tumor growth and angiogenesis. Accordingly, a peptide, which binds specifically to neuropilin-1 competitively with VEGF ligands, may have an activity of inhibiting tumor growth. In addition, when neuropilin-1 is activated, it has an activity of reducing the endothelial barrier VE-cadherin and the epithelial barrier E-cadherin. Accordingly, a peptide, which binds specifically to neuropilin to reduce the levels of VE-cadherin in vascular endothelial cells and E-cadherin in tumor cells, may increase tumor extravasation and tumor tissue penetration of a protein, an antibody, a nanoparticle or a small-molecule drug, with which the peptide is fused or co-administered, and may also increase tumor tissue penetration.

Accordingly, the present inventors have attempted to overcome the limitation of conventional peptides that bind to both neuropilin 1 and 2 and to identify a novel peptide that binds specifically to neuropilin 1 with high affinity without binding to neuropilin 2. Furthermore, the present inventors have attempted to identify a novel peptide that binds bivalently to the VEGF-binding pocket (arginine-binding pocket) of the b1 domain of neuropilin-1 to induce signaling to activate neuropilin-1 to be endocytosed into cells, thereby increasing tumor tissue distribution and accumulation of a fused or co-administered protein, antibody or the like and promoting extravasation of this protein or antibody into tumor tissue, and has the ability to penetrate tumor tissue. Therefore, the present inventors have attempted to develop a novel peptide that is always present as a homodimer and is fused to the C-terminus of the heavy-chain constant region of an antibody while maintaining its activity.

To this end, the present inventors have attempted to construct the yeast surface-displayed immunoglobulin Fc-fused peptide library, and then select a clone that binds to the b1 domain of neuropilin-1. To select peptides that bind only to neuropilin-1, neuropilin-2 was used as a competitor in the selection process. Among the selected clones, a clone which has the ability to penetrate tumor tissue and binds to the b1 domain of neuropilin-1 was identified, and this peptide was bound bivalently to the C-terminus of the heavy-chain of an antibody to construct an antibody-peptide fusion protein that retains the intrinsic function of the antibody. According to this fusion antibody technology, the antibody was accumulated selectively in tumor tissue overexpressing neuropilin-1, and had an increased ability to penetrate tumor tissue. In addition, the present inventors have developed a fusion antibody technology that interferes with binding of vascular endothelial growth factor-A (VEGF165A) to neuropilin-1 to thereby inhibit angiogenesis.

DISCLOSURE OF INVENTION

Technical Problem

It is an aspect of the present disclosure is to provide a peptide, particularly, a tumor penetrating peptide (TPP), which binds only to neuropilin-1 with high specificity and high affinity unlike conventional ligands and peptides that bind to both neuropilin-1 (NRP1) and neuropilin-2 (NRP2). Specifically, it is an aspect of the present disclosure is to provide a peptide, which binds only to neuropilin-1 with high specificity and high affinity, binds competitively with VEGF ligands or the like binding to neuropilin-1, to have an activity both in inhibiting angiogenesis in tumor and penetrating tumor.

It is another aspect of the present disclosure is to provide a fusion protein, a small-molecule drug, a nanoparticle or a liposome, which the above-described peptide binding specifically to NRP1 is fused thereto.

Also, it is another aspect of the present disclosure is to provide a polynucleotide that encodes the above-described peptide binding specifically to NRP1.

Also, it is another aspect of the present disclosure to provide a pharmaceutical composition for treating or preventing cancer or angiogenesis-related diseases, comprises: the above-described peptide binding specifically to NRP1; or a fusion protein, a small-molecule drug, a nanoparticle or a liposome, which the above-described peptide binding specifically to NRP1 is fused thereto.

It is still another aspect of the present disclosure is to provide a composition for diagnosing cancer or angiogenesis-related diseases, comprises: the above-described peptide binding specifically to NRP1; or a fusion protein, a small-molecule drug, a nanoparticle or a liposome, which the above-described peptide binding specifically to NRP1 is fused thereto.

It is yet another aspect of the present disclosure is to provide a method for screening the above-described peptide binding specifically to NRP1.

Technical Solution

An aspect of the present disclosure provides a peptide, particularly, a tumor penetrating peptide (TPP), which binds only to neuropilin-1 with high specificity and high affinity. This neuropilin-1-specific peptide has a sequence different from those of conventional ligands and peptides that bind to both neuropilin-1 (NRP1) and neuropilin-2 (NRP2).

Hereinafter, the present disclosure will be described in detail.

The peptide according to the present disclosure comprises 5 to 50 amino acids, and the C-terminus of the peptide is represented by X1-X2-X3-X4, wherein X1 is arginine, lysine, or any amino acid residue, X2 and X3 are each independently any amino acid residue, and X4 is arginine or lysine.

In one example of the present disclosure, a peptide library fused to the carboxy (C)-terminus of the heavy-chain constant region (Fc) of an antibody was designed to construct Fc-fusion peptide library by displaying the designed peptide library on the yeast cell surface, followed by selection of a clone that binds specifically to the b1 domain of neuropilin-2 to isolate and identify the obtained peptide.

In order to isolate peptides, which bind specifically to neuropilin-1 with high affinity, from the Fc-peptide library, selection was performed using the b1b2 domain protein of neuropilin-1, and the b1b2 domain protein of neuropilin-2 was used as a competitor in the selection process.

In another example of the present disclosure, in order for the peptide binds only to neuropilin-1 with high specificity and high affinity to exhibit biological activity by binding bivalently to neuropilin-1, Fc-fusion peptide comprising a heavy-chain constant region (Fc) and a linker composed of a 15-amino-acid sequence (Gly-Gly-Gly-Gly-Ser)X3 which is fused to the carboxy (C)-terminus of the heavy-chain constant region (Fc) is constructed to isolate and identify the peptide, which shows an activity both in penetrating tumor and inhibiting angiogenesis in tumor.

As used herein, the term "tumor penetrating" refers having one or more of the properties of, for example, 1) specifically recognizing a tumor, particularly, a tumor-specific vascular endothelial cell, a tumor cell or tumor tissue, to accumulate therein, or 2) widening the intercellular space between tumor-associated endothelial cells to promote extravasation, or 3) regulating the intercellular space between tumor cells in a tumor to promote deep penetration into the tumor.

As used herein, the term "inhibition of angiogenesis" refers the property of, for example, binding to neuropilin 1 competitively with VEGF ligands or the like, which bind to neuropilin-1 to promote angiogenesis, to inhibit the activity of the ligands, thereby exhibiting anti-angiogenesis in tumor tissue.

The peptide of the present disclosure may comprise or consist of 5 to 50 amino acids, preferably 7 to 30 amino acids.

In the peptide of the present disclosure, the amino acid residue constituting X3 from the N-terminus may be any amino acid residue, but preferably may be serine, threonine, tyrosine, asparagine, glutamine, histidine, glycine, phenylalanine, leucine, isoleucine, valine, alanine, methionine, proline, lysine, aspartic acid, glutamic acid, or stop codon, more preferably may be selected from the group consisting of histidine, glycine, asparagine, serine, glutamine, phenylalanine, valine, leucine, threonine, arginine, proline, isoleucine, alanine, and lysine. In addition, in the peptide of the present disclosure, the N-terminus may preferably comprise histidine-threonine-proline-glycine (H-T-P-G).

In an embodiment of the present disclosure, the peptide may comprise an amino acid sequence of any one of SEQ ID NO: 1 to SEQ ID NO: 3, and the specific sequence information about SEQ ID NO: 1 to SEQ ID NO: 3 is as follows.

| Name of TPP | NRP1-targeting peptide sequence (N-to-C terminus direction) | SEQ ID NOs: |
|---|---|---|
| TPP1 | HTPGNSNQFVLTSTRPPR | SEQ ID NO: 1 |
| TPP8 | HTPGIATRTPR | SEQ ID NO: 2 |
| TPP11 | HTPGNSKPTRTPRR | SEQ ID NO: 3 |

The most preferred example of the peptide according to the present disclosure is TPP11 of SEQ ID NO: 3.

The peptide binding specifically to NRP1 of an aspect of the present disclosure may further comprise a linker peptide. The linker peptide may comprise or consist of 1 to 50 amino acids, preferably 4 to 20 amino acids, more preferably 4 to 15 amino acids. In addition, the linker peptide may comprise or consist of glycine or serine, and may preferably comprise or consist of an amino acid sequence of (GGGGS)n (wherein n is each independently an integer between 1 and 20), may more preferably comprise or consist of an amino acid sequence of (GGGGS)3.

In an embodiment of the present disclosure, the peptide having the linker peptide bound thereto may comprise amino acid sequence of any one of SEQ ID NOs: 4 to 6.

Specific sequence information about SEQ ID NOs: 4 to 6 is as follows.

| Name of TPP | Linker sequence | NRP1-targeting peptide sequence | SEQ ID NOs: |
|---|---|---|---|
| TPP1 | GGGGSGGGGSGGGGS | HTPGNSNQFVLTSTRPPR | SEQ ID NO: 4 |
| TPP8 | GGGGSGGGGSGGGGS | HTPGIATRTPR | SEQ ID NO: 5 |
| TPP11 | GGGGSGGGGSGGGGS | HTPGNSKPTRTPRR | SEQ ID NO: 6 |

Linker-connected, NRP1-targeting peptide sequence (N-to-C terminus direction)

Another aspect of the present disclosure provides fusion proteins, small-molecule drugs, nanoparticles or liposomes, each of which the peptide (SEQ ID NOs: 1 to 6 selectively) binding specifically to NRP1 is fused thereto.

The proteins may be antibodies, antibody fragments, immunoglobulin, peptides, enzymes, growth factors, cytokines, transcription factors, toxins, antigen peptides, hormones, carrier proteins, motor function proteins, receptors, signaling proteins, storage proteins, membrane proteins, transmembrane proteins, internal proteins, external proteins, secretory proteins, viral proteins, glycoproteins, cleaved proteins, protein complexes, chemically modified proteins, or the like.

As used herein, the term "small-molecule drugs" refers to organic compounds, inorganic compounds or organometallic compounds that have a molecular weight of less than about 1000 Da and are active as therapeutic agents against diseases. The term is used in a broad sense herein. The small-molecule drugs herein encompass oligopeptides and other biomolecules having a molecular weight of less than about 1000 Da.

In the present disclosure, a nanoparticle refers to a particle including substances ranging between 1 and 1,000 nm in diameter. The nanoparticle may be a metal nanoparticle, a metal/metal core shell complex consisting of a metal nanoparticle core and a metal shell enclosing the core, a metal/non-metal core shell consisting of a metal nanoparticle core and a non-metal shell enclosing the core, or a non-metal/metal core shell complex consisting of a non-metal nanoparticle core and a metal shell enclosing the core. According to an embodiment, the metal may be selected from gold, silver, copper, aluminum, nickel, palladium, platinum, magnetic iron and oxides thereof, but is not limited thereto, and the non-metal may be selected from silica, polystyrene, latex and acrylate type substances, but is not limited thereto.

According to the present disclosure, liposomes include at least one lipid bilayer enclosing the inner aqueous compartment, which is capable of being associated by itself. Liposomes may be characterized by membrane type and size thereof. Small unilamellar vesicles (SUVs) may have a single membrane and may range between 20 and 50 nm in diameter. Large unilamellar vesicles (LUVs) may be at least 50 nm in diameter. Oliglamellar large vesicles and multilamellar large vesicles may have multiple, usually concentric, membrane layers and may be at least 100 nm in diameter. Liposomes with several nonconcentric membranes, i.e., several small vesicles contained within a larger vesicle, are referred to as multivesicular vesicles.

Furthermore, the peptide may bind to neuropilin-1 bivalently or multivalently.

As used herein, the term "fusion" refers to unifying two molecules having the same or different function or structure, and the methods of fusing may include any physical, chemical or biological method capable of binding the peptide to the protein, the small-molecule drug, the nanoparticle or the liposome. Preferably, the fusion may be mediated by a linker peptide, and for example, the linker peptide may be fused to the C-terminus of a fragment of an antibody light-chain variable region (Fc).

In an embodiment of the present disclosure, the fusion protein may be an intact antibody to which the peptide binds.

In the present disclosure, an intact antibody has a structure with two full-length light chains and two full-length heavy chains, and each light chain is linked to each heavy chain by a disulfide bond (SS-bond). A constant region of the antibody is divided into a heavy-chain constant region and a light-chain constant region, and the heavy-chain constant region has γ, μ, α, δ, and ε types, and γ1, γ2, γ3, γ4, α1 and α2 subclasses. The light-chain constant region has κ and λ types.

The term "heavy chain" as used herein may be interpreted to include a full-length heavy chain including heavy chain variable region domain VH including an amino acid sequence having a variable region sequence sufficient to confer antigen-specificity and three heavy chain constant region domains CH1, CH2 and CH3, and a fragment thereof. Also, the term "light chain" as used herein may be interpreted to include a full-length light chain including a light chain variable region domain VL including an amino acid sequence having a variable region sequence sufficient to confer antigen-specificity and a light chain constant region domain CL, and a fragment thereof.

In the present disclosure, the term "antibody fragment" refers the heavy-chain or light-chain domain of the antibody, or a fragment thereof. For example, the antibody fragment may be a heavy-chain constant region fragment (CH1, CH2, or CH3), a heavy-chain variable region fragment (VH), a light-chain constant region fragment (CL), a light-chain variable region fragment (VL), an antigen binding fragment (Fab), a single-chain variable fragment (scFv), or a fragment thereof. Preferably, the antibody fragment may be a heavy-chain constant region crystalizable fragment (Fc) comprising hinge-CH2-CH3 of the antibody.

Moreover, the antibody fragment may be a monomer, a dimer, or a multimer.

The antibody includes monoclonal antibodies, non-specific antibodies, non-human antibodies, human antibodies, humanized antibodies, chimeric antibodies, single-chain Fvs (scFV), single chain antibodies, Fab fragments, F(ab') fragments, disulfide-linked Fvs (sdFV) and anti-idiotype (anti-Id) antibodies, and epitope-binding fragments of these antibodies, but is not limited thereto.

The monoclonal antibody may be IgG, IgM, IgA, IgD, or IgE. For example, the monoclonal antibody may be IgG1, IgG2, IgG3, IgG4, IgM, IgE, IgA1, IgA5, or IgD type, and may be IgG1 type. In addition, the light-chain constant region of the antibody may be of λ or κ type.

The peptide may bind to a heavy chain constant region (Fc) fragment of an antibody, preferably to the C-terminus of a heavy chain constant region (Fc) fragment of an antibody. The binding may be performed by a linker peptide.

In addition, another aspect of the present disclosure provides a polynucleotide that encodes the above-described peptide.

The term "polynucleotide" as used herein refers to a deoxyribonucleotide or ribonucleotide polymer present in a single-stranded or double-stranded form. It includes RNA genome sequence, DNA (gDNA and cDNA), and RNA sequence transcribed therefrom. Unless otherwise described, it also includes an analog of the natural polynucleotide.

The polynucleotide comprises not only a nucleotide sequence encoding the above-described peptide, but also a complementary sequence thereto. The complementary sequence includes a sequence fully complementary to the nucleotide sequence and a sequence substantially complementary to the nucleotide sequence. For example, this means a sequence that may be hybridized with a nucleotide sequence encoding an amino acid sequence of any one of SEQ ID NO:1 to SEQ ID NO: 3 and SEQ ID NO:4 to SEQ ID NO: 6 under stringent conditions known in the pertinent art.

Also, the polynucleotide may be modified. The modification includes the addition, deletion, or non-conservative substitution or conservative substitution of nucleotides. The polynucleotide encoding the amino acid sequence is interpreted to include a nucleotide sequence that has a substantial identity to the nucleotide sequence. The substantial identity may refer to a sequence having a homology of at least 80%, a homology of at least 90%, or a homology of at least 95% when aligning the nucleotide sequence to correspond to any other sequence as much as possible and analyzing the aligned sequence using an algorithm generally used in the pertinent art.

Another aspect of the present disclosure provides a recombinant vector comprising the polynucleotide.

The term "vector" as used herein refers to means for expressing a target gene in a host cell. For example, the vector may include plasmid vector, cosmid vector, bacteriophage vector, and virus vectors such as adenovirus vector, retrovirus vector, and adeno-associated virus vector. The vector that may be used as the recombinant vector may be produced by operating plasmid (for example, pSC101, pGV1106, pACYC177, ColE1, pKT230, pME290, pBR322, pUC8/9, pUC6, pBD9, pHC79, pIJ61, pLAFR1, pHV14, pGEX series, pET series and pUC19, etc.), phages (for example, λgt4λB, λ-Charon, λΔz1 and M13, etc.), or virus (for example, CMV, SV40, etc.) commonly used in the pertinent art.

A polynucleotide encoding an amino acid sequence of any one of SEQ ID NO: 1 to SEQ ID NO: 3 and SEQ ID NO: 4 to SEQ ID NO: 6 in the recombinant vector may be operatively linked to a promoter. The term "operatively linked" as used herein refers a functional linkage between a nucleotide expression control sequence (such as a promoter sequence) and a second nucleotide sequence. Accordingly, the regulation sequence may control the transcription and/or translation of the second nucleotide sequence.

The recombinant vector may be generally constructed as a vector for cloning or a vector for expression. As the vector for expression, vectors generally used for expressing foreign protein from plants, animals or microorganisms in the pertinent art may be used. The recombinant vector may be constructed by various methods known in the pertinent art.

The recombinant vector may be constructed to be a vector that employs a prokaryotic cell or an eukaryotic cell as a host. For example, when the vector used is an expression vector and employs a prokaryotic cell as a host, the vector generally includes a strong promoter which may promote transcription (for example, pLλ promoter, trp promoter, lac promoter, tac promoter, T7 promoter, etc.), a ribosome binding site for initiation of translation, and termination sequences for transcription/translation. When the vector employs an eukaryotic cell as a host, a replication origin operating in the eukaryotic cell included in the vector may include an f1 replication origin, an SV40 replication origin, a pMB1 replication origin, an adeno replication origin, an AAV replication origin, a CMV replication origin and a BBV replication origin, etc., but is not limited thereto. In addition, a promoter derived from a genome of a mammal cell (for example, a metathionine promoter) or a promoter derived from a virus of a mammal cell (for example, an adenovirus anaphase promoter, a vaccinia virus 7.5K promoter, a SV40 promoter, a cytomegalo virus (CMV) promoter, or a tk promoter of HSV) may be used, and the promoter generally has a polyadenylated sequence as a transcription termination sequence.

Meanwhile, the vector may express not only the peptide that binds specifically to NRP1 according to the present disclosure, but also an antibody having the peptide fused thereto or a fragment thereof. In the case of an antibody having the peptide fused thereto or a fragment thereof, the vector may use both a vector system that expresses a peptide and an antibody or a fragment thereof in one vector, and a vector system that expresses the peptide and the antibody or the fragment thereof in separate vectors. For the latter, the two vectors may be introduced into the host cell through co-transformation and targeted transformation.

The recombinant vector of the present disclosure may have a cleavage map shown in, for example, FIG. 6 or FIG. 20.

Another aspect of the present disclosure provides a host cell transformed with the recombinant vector.

Any kind of host cell known in the pertinent art may be used as a host cell. Examples of a prokaryotic cell comprise strains such as *E. coli* JM109, *E. coli* BL21, *E. coli* RR1, *E. coli* LE392, *E. coli* B, *E. coli* X 1776, *E. coli* W3110, or strains belonging to the genus *Bacillus* such as *Bacillus subtilus* and *Bacillus thuringiensis*, *Salmonella typhimurium*, *Serratia marcescens* and intestinal flora and strains such as various *Pseudomonas* Spp., etc. In addition, when the vector is transformed in an eukaryotic cell, a host cell such as yeast (*Saccharomyces cerevisiae*), an insect cell, a plant cell, and an mammalian cell, for example, SP2/0, CHO (Chinese hamster ovary) K1, CHO DG44, PER.C6, W138, BHK, COS-7, 293, HepG2, Huh7, 3T3, RN, and MDCK cell line, etc., may be used.

Another aspect of the present disclosure provides a method for preparing a peptide that binds specifically to NRP1, comprising culturing the above-described host cell.

The polynucleotide and a recombinant vector including the polynucleotide the may be inserted into a host cell using an insertion method well known in the pertinent art. For example, when a host cell is a prokaryotic cell, the transfer may be carried out according to $CaCl_2$ method or an electroporation method, etc., and when a host cell is an eukaryotic cell, the vector may be transferred into a host cell according to a microscope injection method, calcium phosphate precipitation method, an electroporation method, a liposome-mediated transformation method, and a gene bombardment method, etc., but the transferring method is not limited thereto. When using microorganisms such as *E. coli*, etc. the productivity is higher than using mammalian cells. However, although it is not suitable for production of intact Ig form of antibodies due to glycosylation, it may be used for production of antigen binding fragments such as Fab and Fv.

The method for selecting the transformed host cell may be readily carried out according to a method well known in the pertinent art using a phenotype expressed by a selected label. For example, when the selected label is a specific antibiotic resistance gene, the transformant may be readily selected by culturing the transformant in a medium containing the antibiotic.

The aspect is a concept including the preparation of a tumor-penetrating peptide (TPP) that binds specifically to NRP1, and an antibody having the peptide fused thereto or a fragment thereof.

An example of a method for preparing a heavy-chain constant region (Fc) fragment of an antibody having fused thereto a peptide that binds specifically to NRP1, specifically, a tumor-penetrating peptide (TPP), comprises the steps of:

1) constructing a recombinant expression vector for expressing the TPP-fusion heavy-chain constant region by cloning the nucleic acids coding antibody heavy-chain constant region hinge-CH2-CH3-linker-TPP, which is a fusion protein of an antibody heavy-chain constant region and the selected peptide that binds specifically to NRP1;

2) transforming the constructed expression vector into a cell to express the fusion protein of the antibody heavy-chain constant region and the selected peptide that binds specifically to NRP1; and 3) purifying and recovering the expressed fusion protein of the antibody heavy-chain constant region and the selected peptide that binds specifically to NRP1.

Another example of a method for preparing an antibody having fused thereto the peptide of the present disclosure comprises the steps of:

1) constructing a recombinant expression vector for expressing a recombinant TPP fused IgG heavy chain of IgG-TPP by cloning nucleic acids coding VH-CH1-hinge-CH2-CH3-linker-TPP and a recombinant expression vector by cloning nucleic acids coding VL-CL;

2) co-transforming the constructed heavy-chain and light-chain expression vector into cells to express the recombinant IgG-TPP protein; and 3) purifying and recovering the expressed recombinant IgG-TPP protein.

An aspect of the present disclosure also provides a pharmaceutical composition for treating or preventing cancer, which comprises the above-described peptide binding specifically to NRP1; or a fusion protein, a small-molecule drug, a nanoparticles or a liposome, which the above-described peptide is fused thereto.

The peptide that binds specifically to NRP1 according to the present disclosure binds specifically to NRP1, and thus is distributed specifically in a tumor and exhibits the ability to penetrate the tumor.

Furthermore, the peptide that binds specifically to NRP1 binds specifically to neuropilin-1, so that the peptide is competitive in binding to neuropilin-1 with VEGF165A. Thus, the peptide can inhibit angiogenesis caused by VEGF165A binding to neuropilin-1 to exhibit therapeutic effects against angiogenesis-related diseases, in addition to cancer therapeutic effects.

An antibody fused with the peptide that binds specifically to NRP1 according to the present disclosure shows a production yield similar to that a wild-type antibody, and has the properties of a bispecific antibody capable of simultaneously targeting two kinds of antigens, that is, an antigen to which the antibody binds, and neuropilin-1 to which the peptide binds. Accordingly, the fused antibody has the capability to reach tumor tissue with high efficiency, and thus can exhibit a high effect on cancer treatment.

The cancer may be selected from the group consisting of squamous cell carcinoma, small cell lung cancer, non-small cell lung cancer, adenocarcinoma of lung, squamous cell carcinoma of lung, peritoneal cancer, skin cancer, skin or ocular melanoma, rectal cancer, anal cancer, esophageal cancer, small intestine cancer, endocrine cancer, parathyroid cancer, adrenal cancer, soft tissue sarcoma, urethral cancer, chronic or acute leukemia, lymphoma, hepatoma, gastrointestinal cancer, pancreatic cancer, glioblastoma, cervical cancer, ovarian cancer, liver cancer, bladder cancer, liver tumor, breast cancer, colon cancer, colorectal cancer, endometrial cancer or uterine cancer, salivary gland cancer, kidney cancer, liver cancer, prostate cancer, vulva cancer, thyroid cancer, liver cancer and head and neck cancer.

The angiogenesis-related disease may be selected from the group consisting of diabetic retinopathy, macular degeneration, age-related macular degeneration, retinopathy of prematurity, corneal graft rejection, neovascular glaucoma, retrolental fibroplasia, epidemic keratoconjunctivitis, vitamin A deficiency, contact lens overwear, atopic keratitis, superior limbic keratitis, pterygium keratitis sicca, sjogren's syndrome, acne rosacea, phylectenulosis, syphilis, mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, trauma, rheumatoid arthritis, systemic lupus, polyarteritis, Wegener's sarcoidosis, scleritis, Stevens-Johnson disease, pemphigoid, radial keratotomy, and corneal graft rejection.

When the composition is prepared as a pharmaceutical composition for preventing or treating cancer or angiogenesis-related diseases, the composition may include a pharmaceutically acceptable carrier. The pharmaceutically acceptable carrier contained in the composition is typically used in the formulation. Examples of the pharmaceutically acceptable carrier included in the composition may include, but are not limited to, lactose, dextrose, sucrose, sorbitol, mannitol, starch, acacia rubber, calcium phosphate, alginate, gelatin, calcium silicate, minute crystalline cellulose, polyvinyl pyrrolidone, cellulose, water, syrup, methyl cellulose, methyl hydroxy benzoate, propyl hydroxy benzoate, talc, magnesium stearate and mineral oil, etc., but are not limited thereto. In addition to the above ingredients, the pharmaceutical composition may further include a lubricant, a wetting agent, a sweetener, a flavoring agent, an emulsifier, a suspension, a preservative, etc.

The pharmaceutical composition for preventing or treating cancer or angiogenesis-related diseases may be administered orally or parenterally. Such a parenteral administration includes intravenous injection, subcutaneous injection, intramuscular injection, intraperitoneal injection, endothelial administration, topical administration, nasal administration, intrapulmonary administration, intrarectal administration, etc. Because a protein or peptide is digested when administered orally, it is preferred that a composition for oral administration is formulated to coat an active substance or to be protected against degradation in stomach. Also, the pharmaceutical composition may be administered by any device which can transport active substances to target cells.

Proper dose of the pharmaceutical composition for preventing or treating cancer or angiogenesis-related diseases may vary according to various factors such as method for formulating, administration method, age, weight, gender, pathological state of patient, food, administration time, administration route, excretion rate and reaction sensitivity, etc. Preferably, a proper dose of the composition is within the range of 0.001 and 100 mg/kg based on an adult. The term "pharmaceutically effective dose" as used herein refers to an amount sufficient to prevent or treat cancer or angiogenesis-related diseases.

The composition may be formulated with pharmaceutically acceptable carriers and/or excipients according to a method that can be easily carried out by those skilled in the art, and may be provided in a unit-dose form or enclosed in a multiple-dose vial. Here, the formulation of the pharmaceutical composition may be in the form of a solution, a suspension, syrup or an emulsion in oily or aqueous medium, or may be extracts, powders, granules, tablets or capsules, and may further include a dispersion agent or a stabilizer. Also, the composition may be administered individually or in combination with other therapeutic agents, and may be administered sequentially or simultaneously with conventional therapeutic agents. Meanwhile, the composition includes an antibody or an antigen-binding fragment, and thus may be formulated into immuno liposome. Liposome including an antibody may be prepared according to a method well known in the pertinent art. The immuno liposome is a lipid composition including phosphatidylcholine, cholesterol and polyethyleneglycol-derived phosphatidylethanolamine, and may be prepared by reverse phase evaporation method. For example, a Fab' fragment of antibody may be conjugated to liposome through disulphide exchange reaction. Liposome may further include chemical therapeutic agents such as Doxorubicin.

The composition of the present disclosure may be administered as an individual therapeutic agent or in combination with therapeutic methods that have been usually used for treatment or prevention of cancer. The composition may be administered in combination with other therapeutic methods, and may be administered sequentially or simultaneously with conventional therapeutic methods.

Examples of conventional therapeutic methods include, but are not limited to, surgery, chemotherapy, radiotherapy, hormonal therapy, biological therapy, and immunotherapy. Furthermore, the composition of the present disclosure may be used for prevention or treatment of diseases or disorders other than cancer, which are related to or characterized by undesirable angiogenesis. The treatment method of the present disclosure comprises administering to a patient in need of such treatment or prevention a therapeutically or prophylactically effective amount of a specific drug or a pharmaceutically acceptable salt, solvate, hydrate, steric isomer, inclusion complex or prodrug thereof. In one embodiment of the present disclosure, the composition is administered in combination with other drugs ("secondary drugs") or a method for curing, treating or preventing cancer. Examples of the secondary drugs include, but are not limited to, proteins, antibodies, small-molecule drugs, liposomes, nanoparticles, stem cells, and the like.

An aspect of the present disclosure also provides a pharmaceutical composition for treating or preventing cancer, which includes: the above-described peptide binding specifically to NRP1; or a fusion protein, a small-molecule drug, a nanoparticles or a liposome, which the peptide is fused thereto.

The term "diagnosing" as used herein refers to demonstrating the presence or characteristic of a pathophysiological condition. Diagnosing in the present disclosure refers to demonstrating the onset and progress of cancer.

The peptide binding specifically to the NRP1 may bind to a fluorescent substance for molecular imaging in order to diagnose cancer through images.

The fluorescent substance for molecular imaging refers to all substances generating fluorescence. Preferably, red or near-infrared fluorescence is emitted, and more preferably, fluorescence with high quantum yield is emitted. However, the fluorescence is not limited thereto.

Preferably, the fluorescent substance for molecular imaging is a fluorescent substance, a fluorescent protein or other substances for imaging, which may bind to the peptide that specifically binds to NRP1, but is not limited thereto.

The fluorescent substance is preferably, for example, fluorescein, BODYPY, tetramethylrhodamine, Alexa, cyanine, allopicocyanine, or a derivative thereof, but is not limited thereto.

The fluorescent protein is preferably, for example, Dronpa protein, enhanced green fluorescence protein (EGFP), red fluorescent protein (DsRFP), Cy5.5, which is cyanine fluorescent substance presenting near-infrared fluorescence, or other fluorescent proteins, but is not limited thereto.

Other substances for imaging are preferably, for example, ferric oxide, radioactive isotope, etc., but are not limited thereto, and they may be applied to imaging equipment such as MR, PET.

The present disclosure also provides a method for screening the above-described peptide.

Specifically, the method of screening the peptide comprises the steps of: (1) designing a peptide library capable of interacting with the arginine-binding pocket of the NRP1-b1 domain; (2) fusing the peptide library of step (1) to the C-terminus antibody heavy-chain constant Fc region; (3) binding the Fc-fused peptide library of step (2) in the presence of high amount of NRP2-b1b2 as a competitor; and (4) screening desirable Fc-fused peptides based on the binding affinity between the isolated Fc-fused peptide library and NRP1-b1b2 bound in step (3).

In an embodiment of the present disclosure, construction of the library in step (1) is to design a peptide library having an amino acid sequence that is not found in nature, by performing PCR with primers using a conventional antibody heavy-chain constant region (Fc) fragment and a semaphorin 3-derived sequence as templates.

The primer using the semaphorin 3-derived sequence as a template may have the following sequence.

Oligonucleotide sequences for construction of a peptide library fused to antibody heavy-chain constant region (Fc)

| Name of primer | Oligonucleotide sequence | SEQ ID NOs: |
|---|---|---|
| Forward primer | 5'-CAT CGA GAA AAC CAT CTC CAA AGC CA-3' | SEQ ID NO: 7 |
| Reverse primer | 5'-A AAG TCG ATT TTG TTA CAT CTA CAC TGT TGT TAT CAG ATC TCG AGA AGC TTA TCA VDN VDN VDN VDN VDN VDN VDN VDN VDN VDN VDN VDN VDN VDN VDN VDN VDN VDN TCC AGG AGT ATG TGA TCC-3' | SEQ ID NO: 8 |

In an embodiment of the present disclosure, in step (2), the library constructed in step (1) is fused to the antibody heavy-chain constant region. In step (3), the library fused to the heavy-chain constant region is displayed on the yeast cell surface, and then bound to the target molecule NRP1-b1b2. At this time, it is bound competitively with NRP2-b1b2 protein, and a peptide that binds only to NRP1 without binding to NRP2 is selected.

Advantageous Effects

The peptide that binds specifically to NRP1 without binding to NRP2 according to the present disclosure comprises an amino acid sequence capable of binding specifically to NRP1. The peptide that binds specifically to NRP1 according to the present disclosure, and a protein fused with the peptide, have the property of binding specifically to NRP1, and thus are accumulated specifically in tumor tissue, widens the intercellular space between tumor-associated endothelial cells to promote extravasation, and regulate the intercellular space in tumor tissue to increase the penetration thereof into the tumor tissue. Furthermore, an antibody or antibody fragment fused with the peptide that binds specifically to NRP1, when administered at the same dose as that of a control antibody not fused with the peptide, is accumulated specifically in tumor tissue, and the penetration thereof into tumor tissue increases, thereby exhibiting a significantly increased anti-tumor activity in vivo.

An antibody or a fragment thereof, fused with the peptide that binds specifically to NRP1 according to the present disclosure, can be accumulated in tumor tissue with high efficiency while retaining the antigen binding ability of the original antibody, and has an increased ability to penetrate tumor tissue, thereby exhibiting high effects on tumor treatment and diagnosis. Furthermore, an antibody fragment fused with the peptide that binds specifically to NRP1 according to the present disclosure has the property of inhibiting VEGF165A binding to NRP1 to inhibit angiogenesis caused by VEGF165A, and thus can be used for treatment and diagnosis of various diseases, including tumor growth and metastasis, age-related macular degeneration, diabetic retinopathy, rheumatoid arthritis, and the like.

An antibody or a fragment thereof, fused with the peptide that binds specifically to NRP1 according to the present disclosure, shows a production yield similar to that of a wild-type antibody not fused with the peptide. Moreover, the fused antibody or a fragment thereof retains the antigen-binding ability of the original wild-type antibody, and the binding affinity of the heavy-chain constant region (Fc) for protein A and protein G. Thus, it does not require additional production costs, unlike conventional antibodies, and has the property retaining the anticancer activity of the antibody.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1(A) and 1(B) schematically show the structures of neuropilin 1 and 2.

In FIGS. 1(A) and 1(B), neuropilin includes major 5 domains, in which a1 and a2 domains from the N-terminus are classified as CUB domains, to which the semaphorin Ig-like C2 type domain binds. Particularly, this domain forms a complex with plexin to increase the semaphorin-plexin binding affinity. The b 1 and b2 domains are classified as FV/VIII domains, and the C-terminus of VEGF or class 3 semaphorin ligands binds thereto. Particularly, in this portion, a site to which heparin can bind is present and it facilitates the binding of ligands containing many positively charged residues. Further, MAM induces oligomerization, the transmembrane domain (TM) enables neuropilin to be fixed to the cell surface, and in a cytosolic domain, a site capable of binding to a Postsynaptic density 95, Disk large, Zona occludens 1 (PDZ) domain is present.

FIG. 2 shows a binding complex of neuropilin-1 (NRP1) with a fusion protein of an antibody heavy-chain constant region and a selected peptide that binds specifically to NRP1 and a fusion protein of an antibody heavy-chain constant region and a selected peptide that binds specifically to NRP1. A dimeric clone is obtained which binds specifically to the arginine-binding pocket of the NRP1 b 1 domain without binding to NRP2.

FIG. 3 is a schematic view of a library constructed by adding the degenerate codon NHB (ATGC/ACT/TCG) to a 18-residue portion (residues 5 to 22) from the C-terminus of an A22p peptide (N terminus-HTPGNSNKWKHLQENKKGRPRR-C terminus) (SEQ ID NO: 1) that binds to both NRP1 and NRP2. A Fc-fusion peptide library was constructed by fusing a linker comprising 15-amino-acid sequence (Gly-Gly-Gly-Gly-Ser-Gly-Gly-Gly-Gly-Ser-Gly-Gly-Gly-Gly-Ser (SEQ ID NO: 9) to the carboxy (C)-terminus of an antibody heavy-chain constant region (Fc). The constructed Fc-fusion peptide library is fused to Agalp-Aga2p on the yeast cell surface and displayed on the yeast cell surface as shown at the bottom of FIG. 3, and the peptide library is present at the C-terminus of the antibody heavy-chain constant region (Fc) fragment.

FIGS. 4(A) and 4(B) show proteins used to select a peptide that binds specifically to NRP1, and the results of MACS and FACS analysis.

FIG. 4(A) schematically shows the structures of biotinylated neuropilin-1 b1b2 protein and neuropilin-2 b1b2 protein used to select a peptide that binds specifically to NRP1, and also shows the results of SDS-PAGE with expressed and purified neuropilins.

FIG. 4(B) shows FACS analysis results obtained by performing MACS and FACS of the constructed library using biotinylated NRP1-b1b2 as a binding antigen and a 10-fold higher concentration of NRP2-b1b2 as a competitive antigen, and analyzing a pool bound to NRP1-b1b2 in each selection round. The expression level of the antibody heavy-chain constant region (Fc) and binding to biotinylated NRP1-b1b2 could be analyzed, and comparison with cells including Fc-A22p displayed on the yeast cell surface was performed. As MACS and FACS are repeated, the number of clones, which bind to biotinylated NRP1-b1b2 and do not affect the expression of the antibody heavy-chain constant region (Fc), increases.

FIGS. 5(A) and 5(B) show the results of FACS performed to identify binding of selected single clones to biotinylated NRP1-b1b2.

In FIG. 5(A), a total 50 single clones were analyzed competitively with A22p, and the binding affinity for each clone to 100 nM biotinylated NRP1-b1b2 was identified by mean fluorescence intensity shown in FACS. Among the clones, clones, named TPP1, TPP8 and TPP11, which showed higher mean fluorescence intensities, were selected.

Figure 7A:
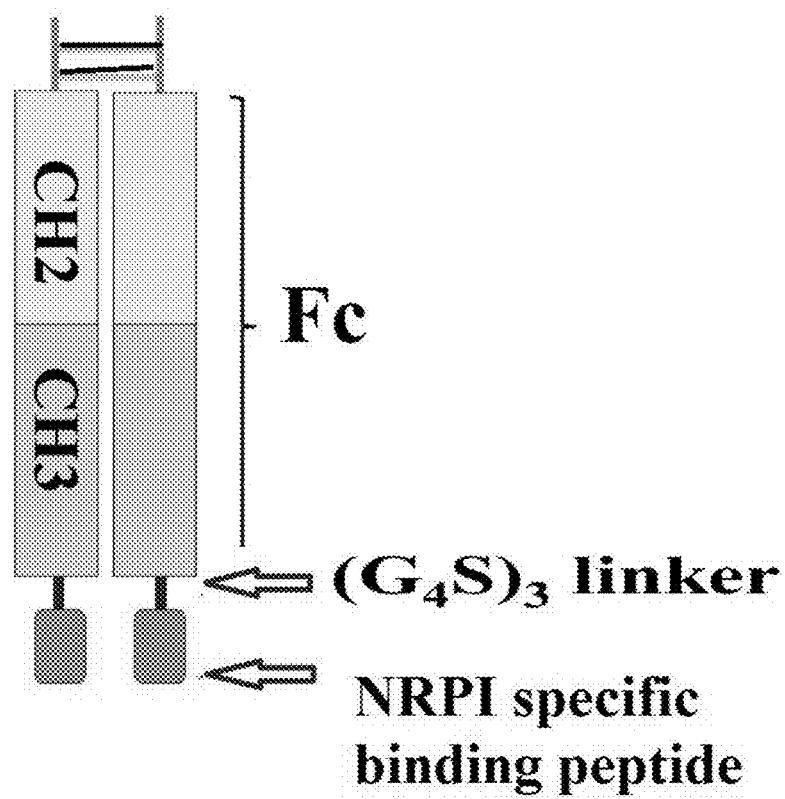
Figure 7B:
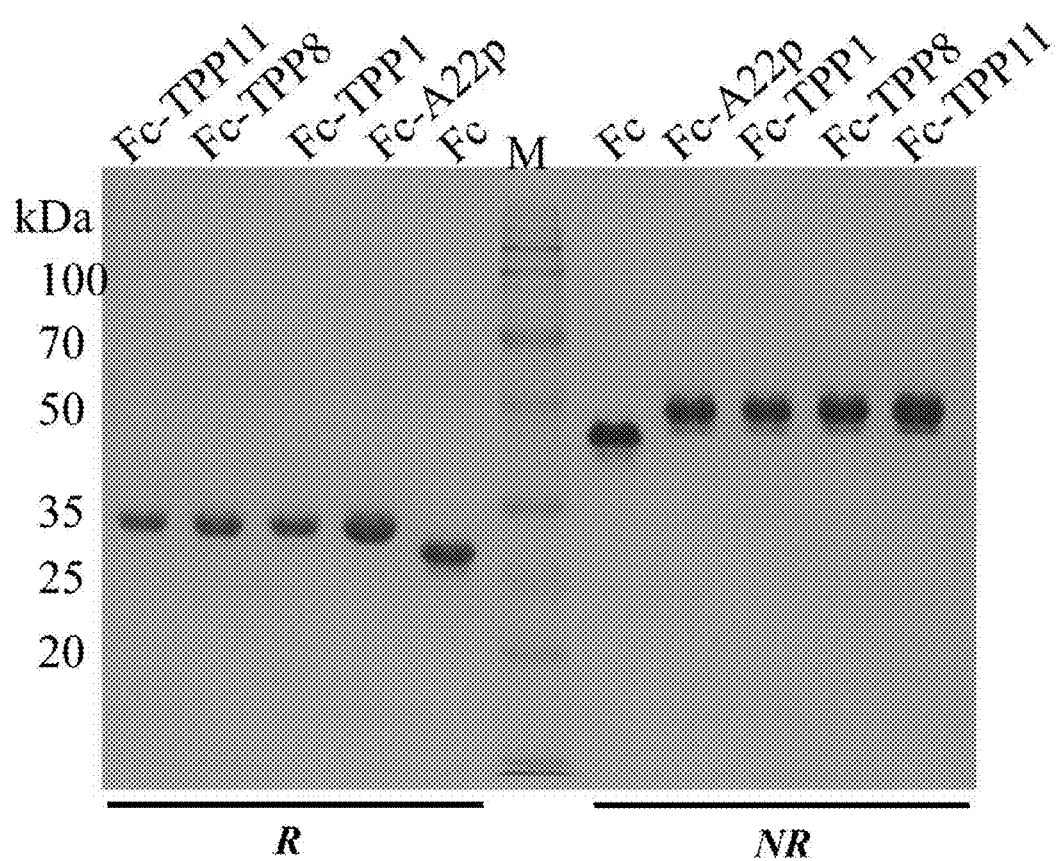

FIGS. 7(A) and 7(B) show a schematic view of a fusion protein of an antibody heavy-chain constant region and a selected peptide that binds specifically to NRP1, and also shows the results of expressed and purified SDS-PAGE.

In FIG. 7(A), the antibody heavy-chain constant region was constructed starting from the N-terminal hinge so as to maintain two disulfide bonds to easily form a dimer. The peptide that binds specifically to NRP1 was fused to the end of CH3 of the antibody heavy-chain constant region by a peptide linker comprising 15 amino acids ((G4S)3).

In FIG. 7(B), dimer formation and purification purity of each clone can be seen on SDS-PAGE. In addition, the difference in size caused by introduction of a linker and a peptide that binds specifically to NRP1 can be seen.

Figure 8A:
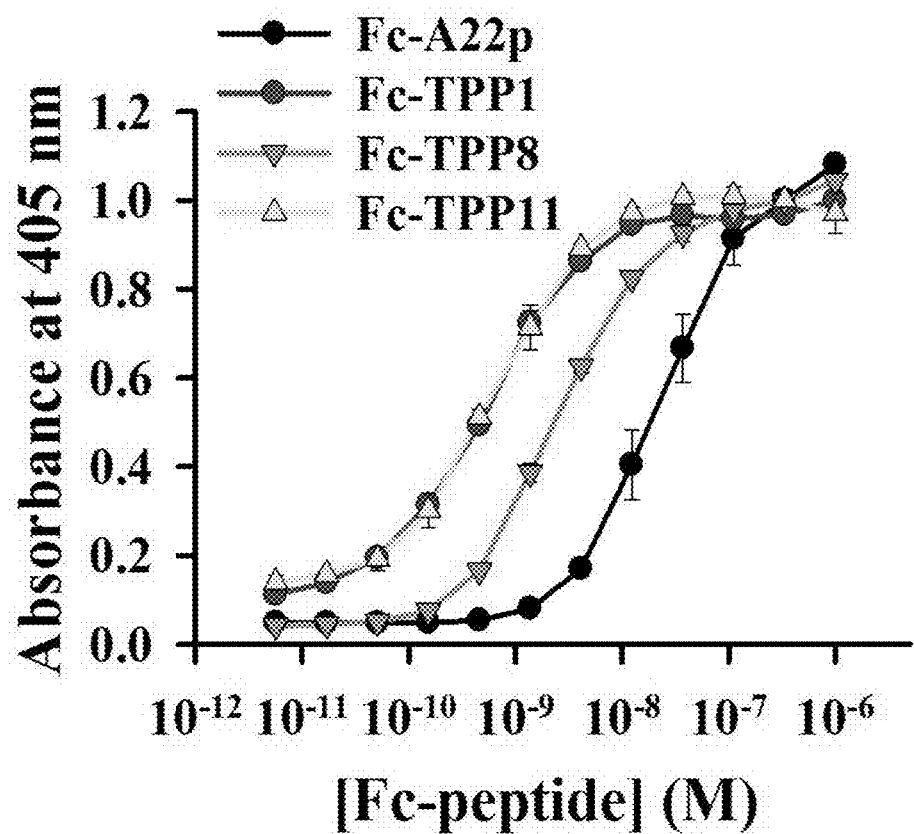
Figure 8B:
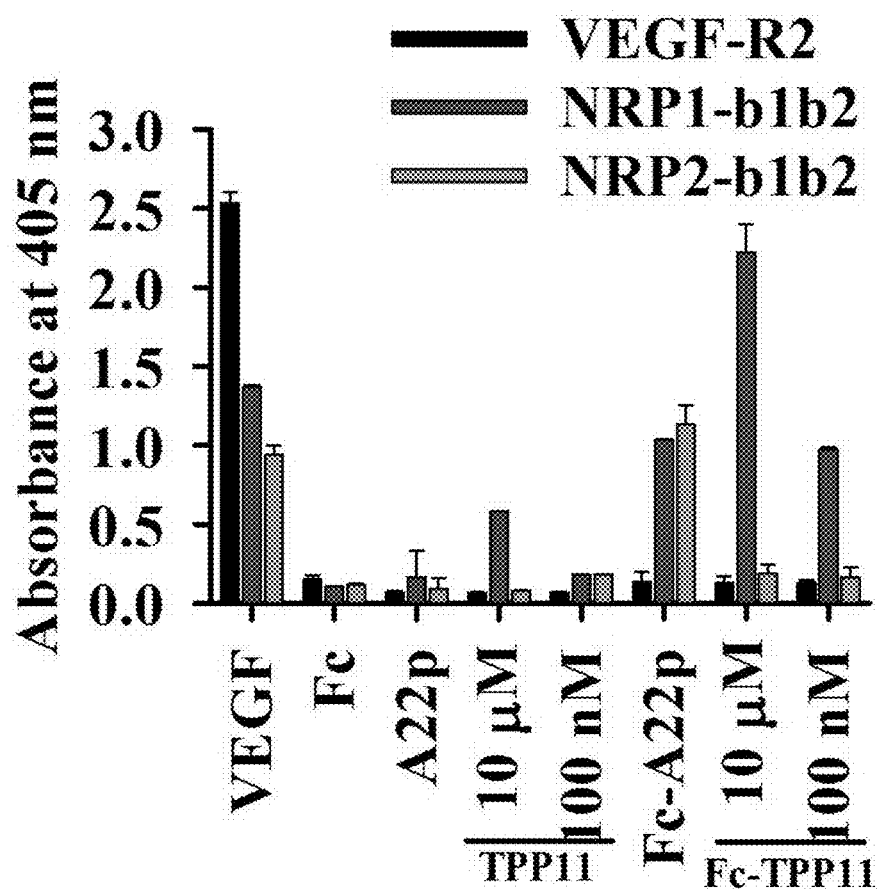

FIG. 8 shows FIGS. 8(A) and 8(B) show the results of ELISA analysis performed to measure the NRP1 binding affinities of Fc-TPP1, Fc-TPP8 and Fc-TPP11, which are each a fusion protein of an antibody heavy-chain constant region, expressed and purified from mammalian cells, and a peptide that binds specifically to NRP1.

In FIG. 8(A), the results of concentration-dependent ELISA indicate that Fc-TPP1, Fc-TPP8 and Fc-TPP11 have about 10-fold to 60-fold higher affinities than Fc-A22p for the NRP1-b1b2 domain.

In FIG. 8(B), Fc-TPP11 binds specifically to NRP1-b1b2 without binding to NRP2-b1b2, unlike Fc-A22p. In addition, it does not bind to the control VEGFR2. The synthetic peptide TPP11 not fused to Fc shows an at least 100-fold lower affinity than Fc-TPP11 for NRP1-b1b2 protein. This indicates that Fc-TPP11 has a high affinity due to the avidity effect.

Figure 9:
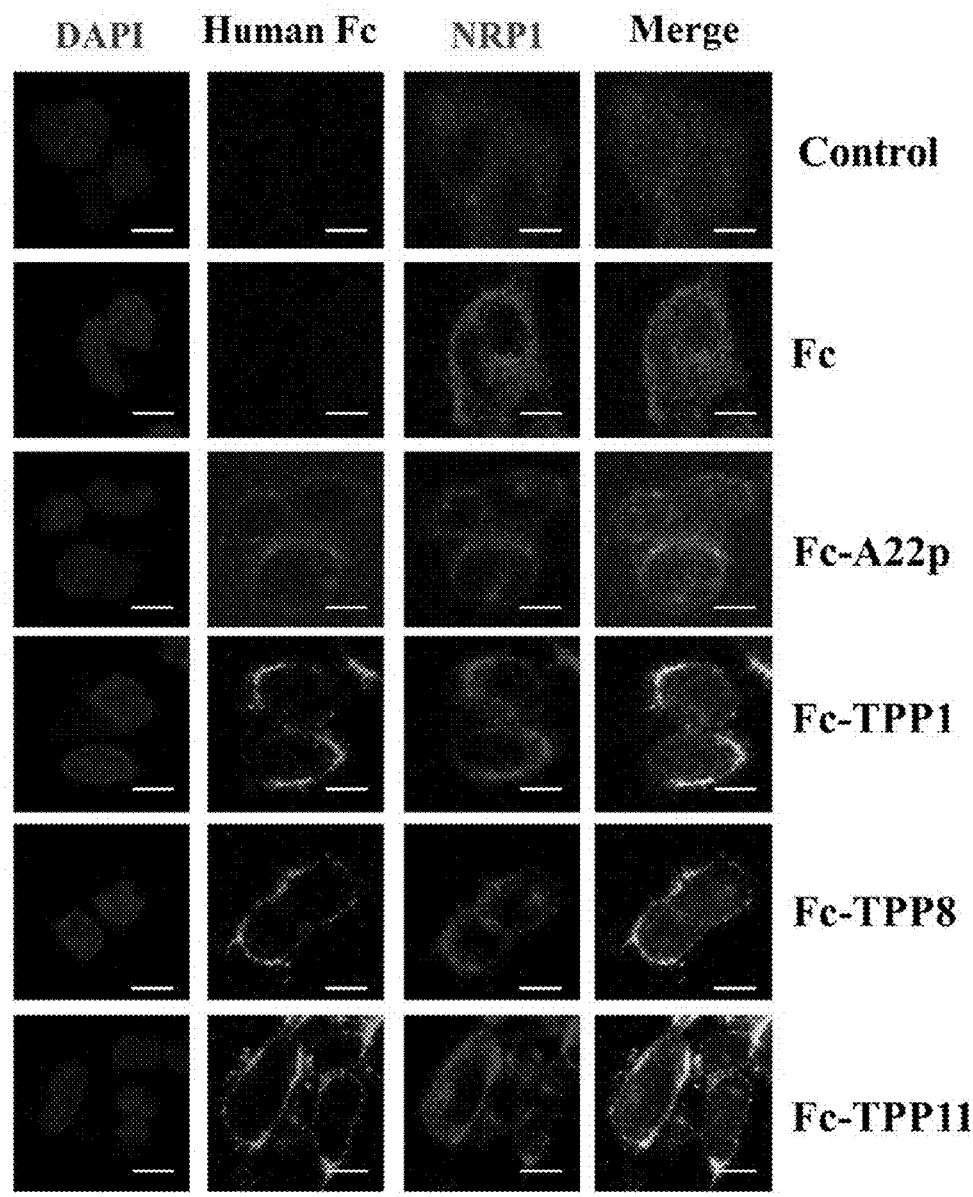

FIG. 9 shows the results of confocal microscopic analysis to observe co-localization with NRP1 displayed on the human umbilical vein endothelial cell (HUVEC) surface in order to determine whether the Fc-TPP1, Fc-TPP8 or Fc-TPP11 protein binds specifically to NRP1 displayed on the cell surface. Fc-TPP1, Fc-TPP8 and Fc-TPP11 were treated with a control (PBS buffer), Fc or Fc-A22p in the same manner, and the degree of binding thereof to the cell surface was observed by staining. As a result, Fc-TPP1, Fc-TPP8 or Fc-TPP11 co-localized with NRP1 on the cell surface, unlike Fc, indicating that the fusion protein of the antibody heavy-chain constant region and the selected peptide that binds specifically to NRP1 binds specifically to NRP1.

Figure 10:
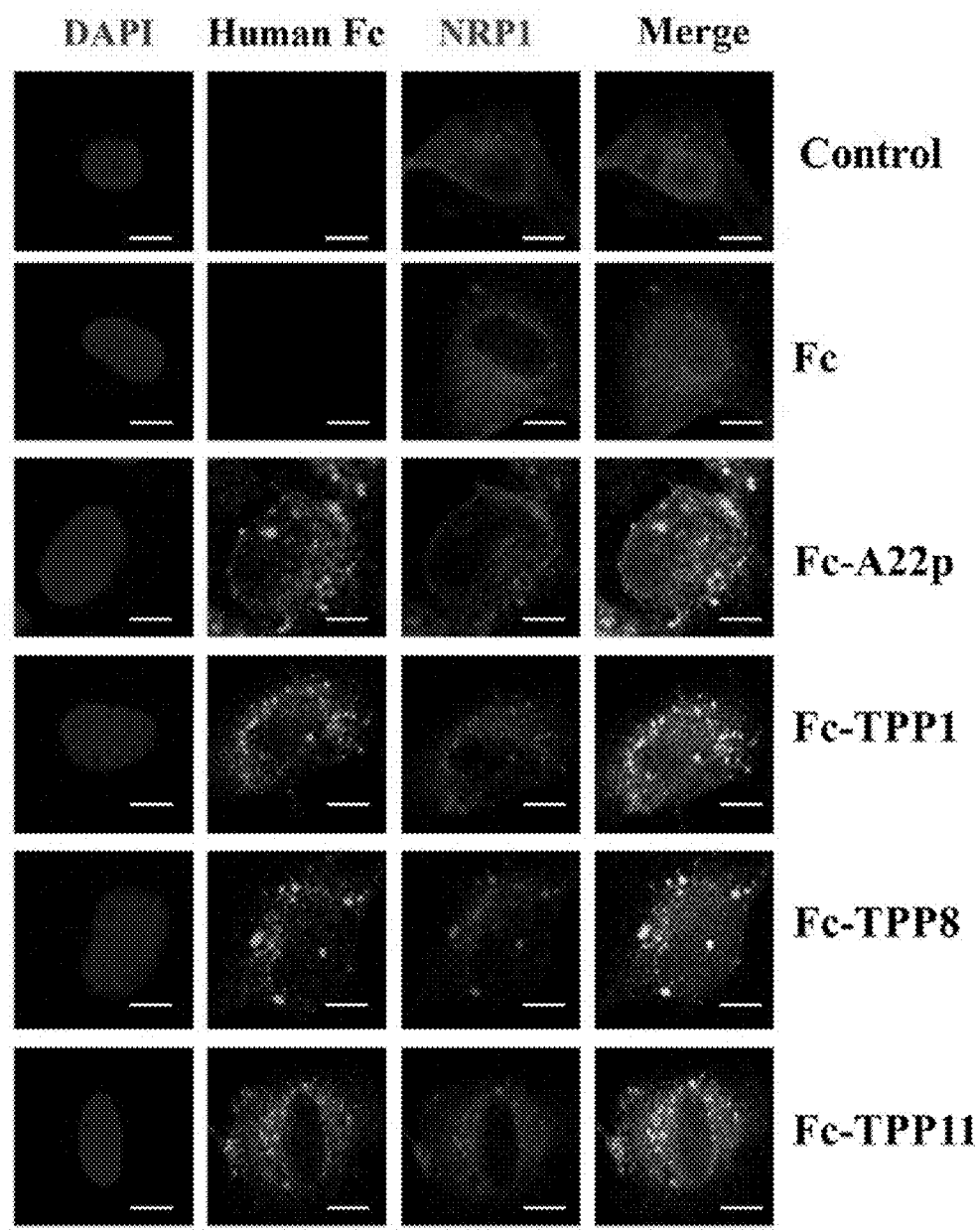

FIG. 10 shows the results of confocal microscopic analysis performed to confirm whether the Fc-TPP1, Fc-TPP8 or Fc-TPP11 protein binds specifically to NRP1 displayed on the cell surface to activate NRP1 and is endocytosed into cells. Human umbilical vein endothelial cells (HUVECs) were treated with a control (PBS buffer), Fc, Fc-A22p, Fc-TPP1, Fc-TPP8 or Fc-TPP11 under the same conditions, and the degree of endocytosis was stained by staining. As a result, it was observed that Fc-TPP1, Fc-TPP8 or Fc-TPP11 endocytosed into the cells while it co-localized with NRP1, unlike Fc. This suggests that Fc-TPP1, Fc-TPP8 or Fc-TPP11 binds specifically to NRP1 and activate NRP1.

Figure 11A:
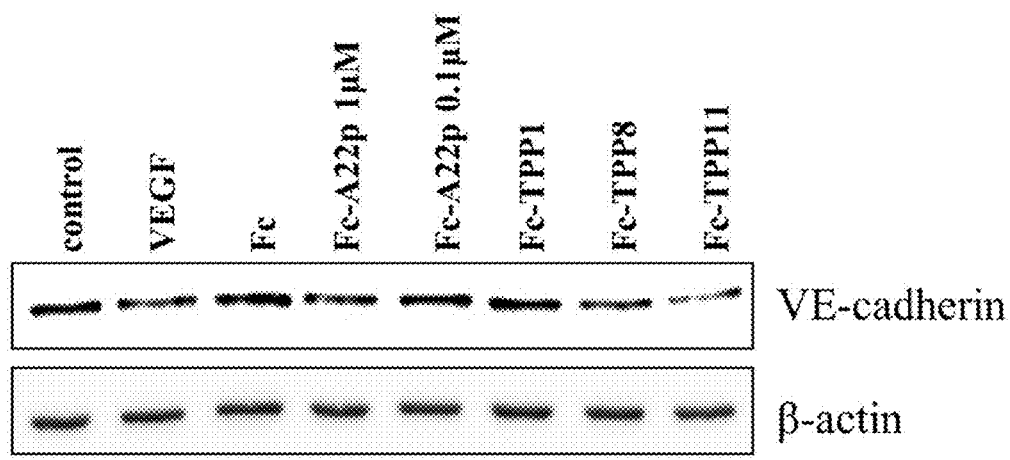
Figure 11B:
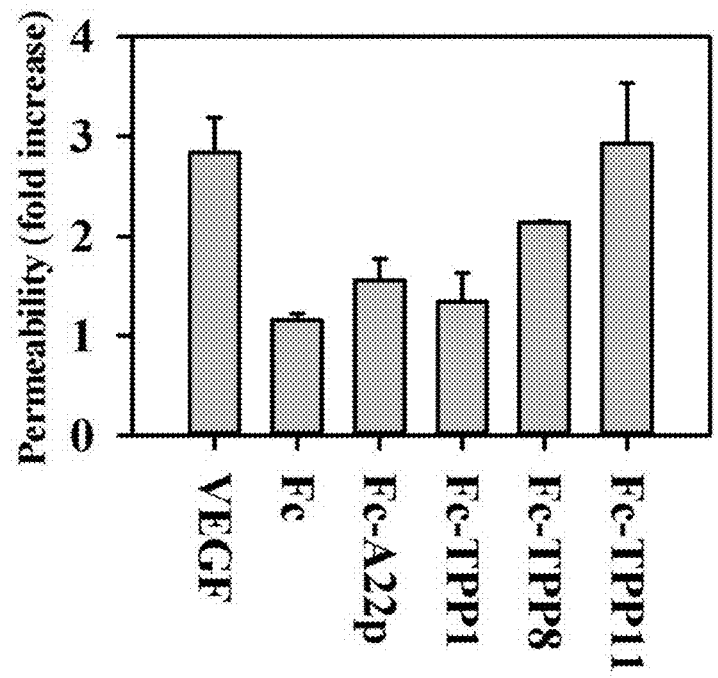

FIGS. 11(A) and 11(B) show the results of analyzing the biological mechanisms of Fc-TPP1, Fc-TPP8 and Fc-TPP11 proteins in HUVEC.

FIG. 11(A) shows the results of Western blot analysis performed to examine the biological mechanisms of Fc-TPP1, Fc-TPP8 and Fc-TPP11 proteins in HUVEC. VEGF165A as a control group showed an improved ability to penetrate HUVEC, as can be seen by a reduction in VE-cadherin, unlike Fc. The control group VEGF165A reduced VE-cadherin, and among selected single clones that bind specifically to NRP1, Fc-TPP11 most effectively reduced VE-cadherin. Moreover, it was shown that Fc-TPP11 more effectively reduced VE-cadherin at a 10-fold lower concentration compared to Fc-A22p protein. FIG. 11(B) shows the results of Transwell assay performed to confirm whether the Fc-TPP1, Fc-TPP8 or Fc-TPP11 protein has an improved ability to penetrate human umbilical vein endothelial cells (HUVEC). The results indicate that VEGF165A, Fc-TPP8 and Fc-TPP11 had an increased ability to effectively penetrate the cells. However, Fc-TPP1 having no ability to reduce VE-cadherin had no increased penetrating ability. Such results have a close connection with the results shown in FIG. 11(A).

Figure 12:
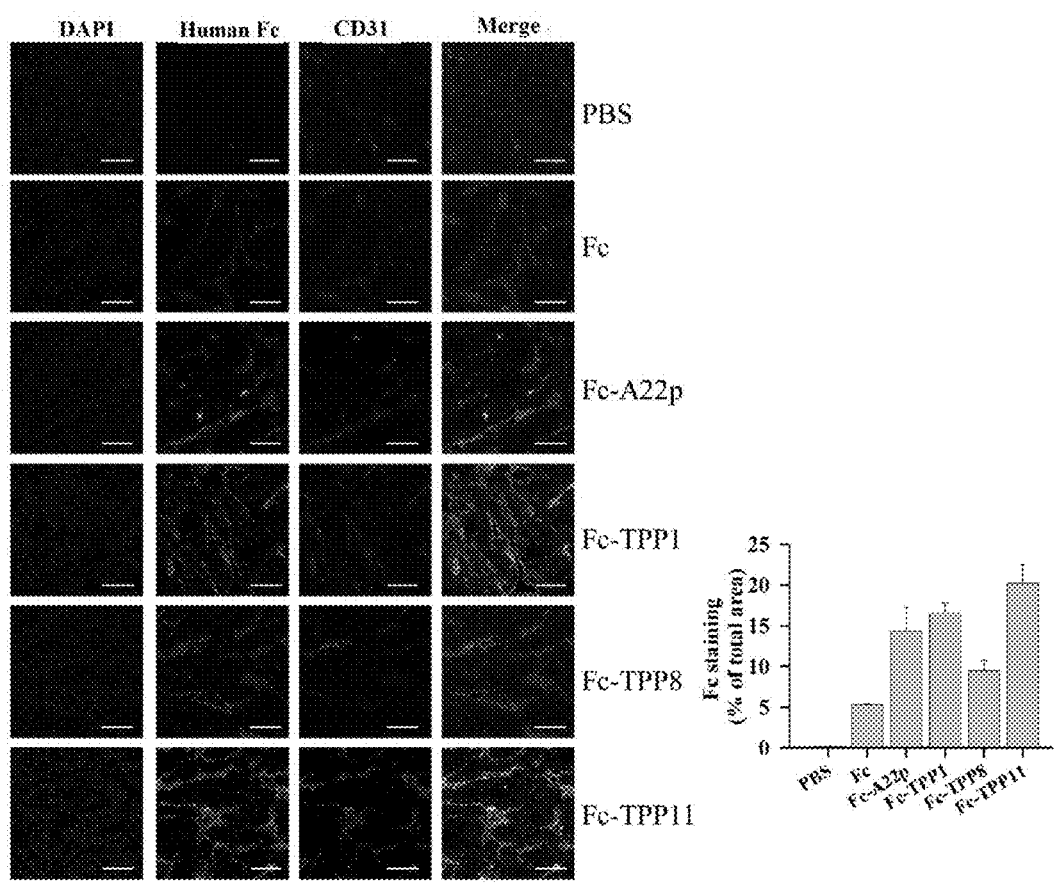

FIG. 12 shows the results of immunohistochemistry performed to identify whether the Fc-TPP1, Fc-TPP8 or Fc-TPP11 protein accumulates in tumor tissue and penetrates tissue. Human epidermoid cancer A431 cells were transplanted and grown in nude mice, after which the Fc-TPP1, Fc-TPP8 or Fc-TPP11 protein was injected into the tail vein, and then the distribution of the Fc-fusion protein was analyzed by double staining with blood vessels (CD31). As a result, it was shown that the Fc-TPP1, Fc-TPP8 or Fc-TPP11 protein selectively reached tumor tissue, unlike the control Fc, and effectively penetrated tumor tissue. Particularly, it was shown that Fc-TPP1 and Fc-TPP11 more effectively penetrated tumor tissue, compared to the Fc-A22p protein. The bar graph on the right side shows the results of quantifying accumulation in tumor tissue.

Figure 13A:
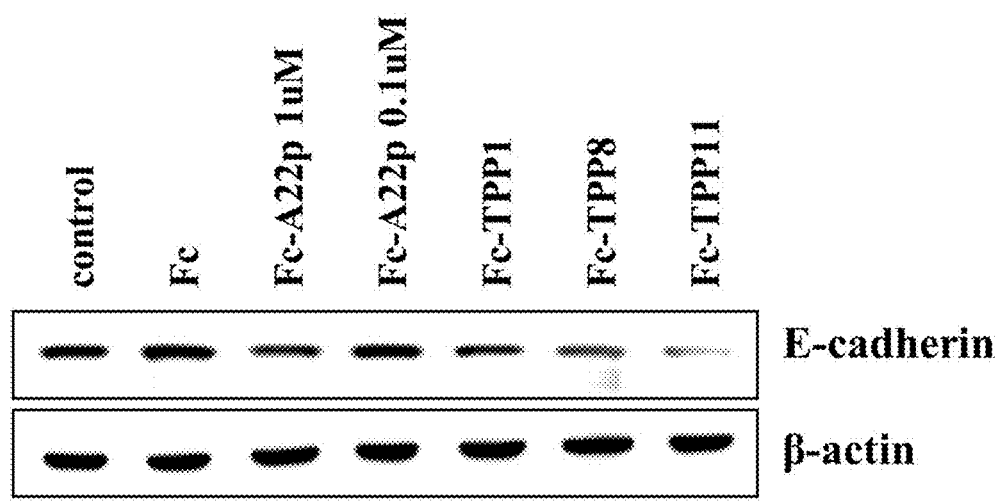
Figure 13B:
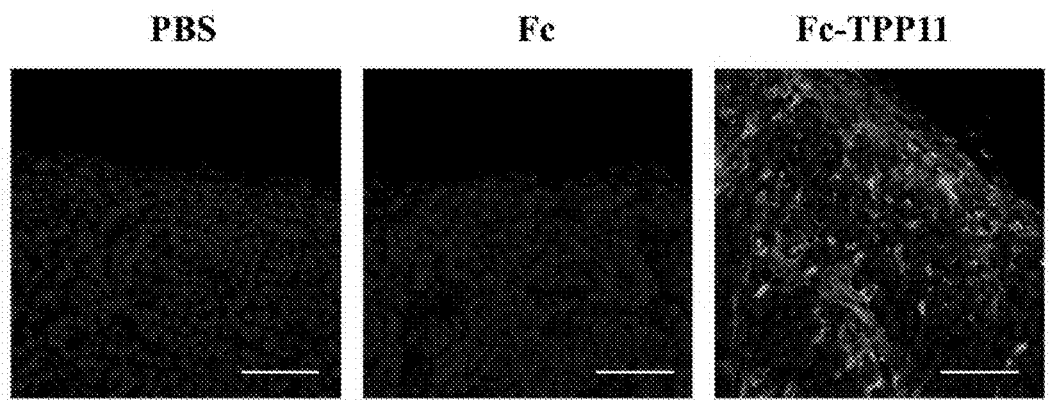

FIGS. 13(A) and 13(B) show the results of measuring the activity of Fc-TPP11 in epithelial cancer-derived tumor cells and tissue.

FIG. 13(A) shows the results of Western blot analysis performed to observe the change in E-cadherin in human head and neck cancer FaDu cells by the Fc-TPP1, Fc-TPP8 or Fc-TPP11 protein. As a result, among the selected single clones that bind specifically to NRP1, Fc-TPP11 most effectively induced a reduction in E-cadherin, unlike Fc, and reduced E-cadherin at a 10-fold lower concentration compared to that of Fc-A22p. FIG. 13(B) shows the results of ex vivo tumor penetration assay performed to confirm whether Fc-TPP11 binds to NRP1 to regulate the intercellular space in epithelial tissue and has the ability to penetrate tumor tissue. It was shown that the control group Fc did not penetrate tumor tissue, whereas Fc-TPP11 had the ability to penetrate tumor tissue even in the absence of blood vessels by regulating the intercellular space derived from the reduction of VE-cadherin and E-cadherin, which are functioning as cell adhesion factors through NRP1.

Figure 14A:
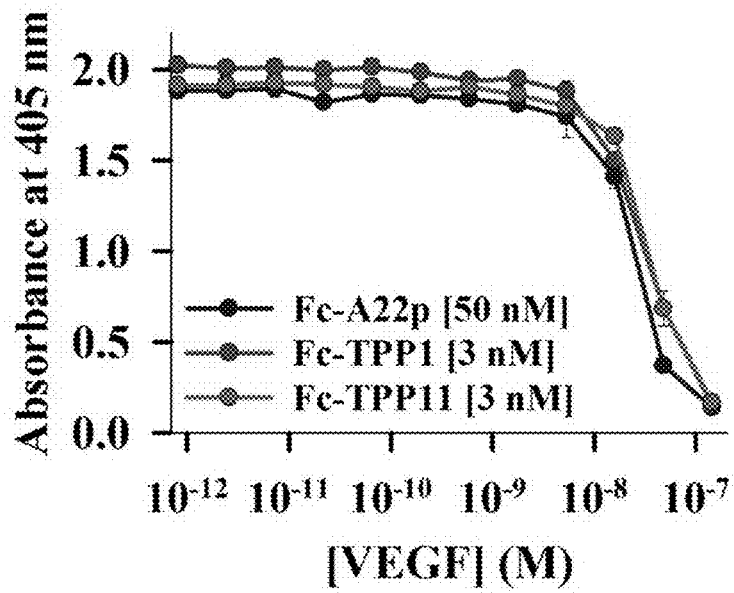
Figure 14B:
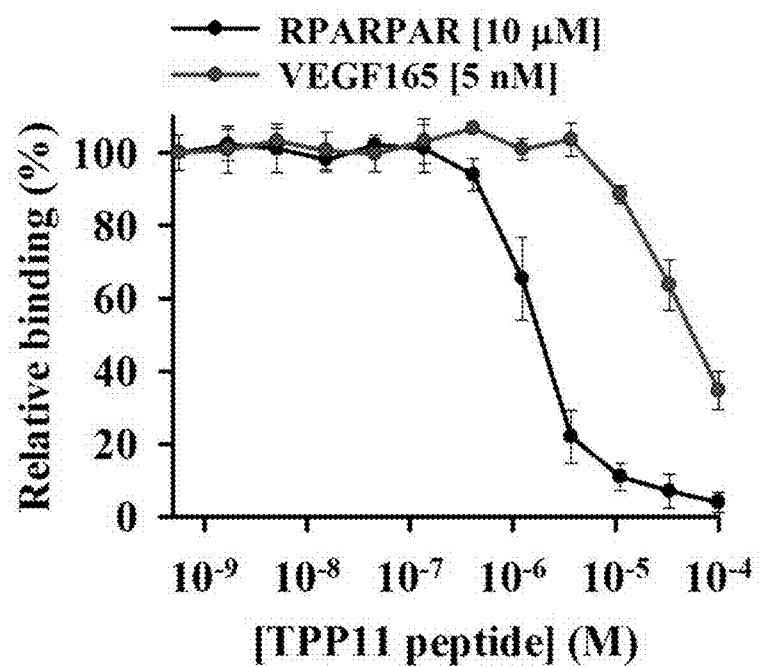

FIGS. 14(A) and 14(B) show the results of evaluating whether the TPP11 peptide binds to NRP1-b1b2 competitively with VEGF165A.

FIG. 14(A) shows results indicating that Fc-TPP1 and Fc-TPP11 bind to NRP1 competitively with VEGF165A to inhibit VEGF165A binding to NRP1, even at very low concentrations compared to Fc-A22p. This suggests that the position at which Fc-TPP1 and Fc-TPP11 bind to NRP1-b1b2 is the identical arginine-binding pocket to which VEGF165A binds.

FIG. 14(B) shows the results of competitive binding ELISA performed to examine whether the synthesized TPP11 peptide binds to NRP1 competitively with a RPAR-PAR peptide (Teesalu et al. 2009) and a VEGF165A ligand, which bind to the arginine-binding pocket located in NRP1-b1. It was shown that the synthesized TPP11 peptide did bind to NRP1 competitively with the RPARPAR peptide and VEGF165A known to bind to the arginine-binding pocket of NRP1-b1. This demonstrates that TPP11 binds to the arginine-binding pocket of NRP1-b1.

Figure 15C:
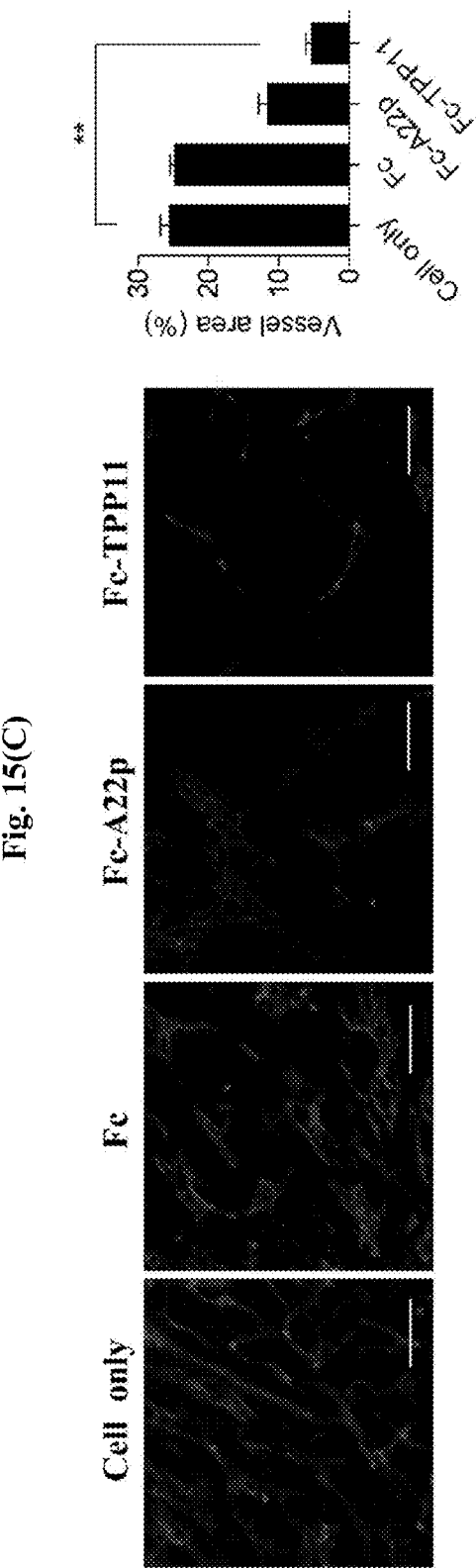

FIGS. 15(A), 15(B), and 15(C) show the results of measuring the anti-angiogenesis activity of Fc-TPP11.

FIG. 15(A) shows the results of a tube formation assay performed to examine whether Fc-TPP11 inhibits VEGF165A-induced tube formation in human umbilical vein endothelial cells (HUVEC). As a result, it was shown that Fc-TPP11 effectively inhibited VEGF165A-induced tube formation in epithelial cells.

FIGS. 15(B) and 15(C) shows the results of an in vivo matrigel plug assay performed to examine whether Fc-TPP11 can inhibit VEGF165A-induced angiogenesis in living mice. In FIG. 15(B), angiogenesis was measured as the density of blood vessels by immunohistochemistry with anti-CD31 antibody. The right side of FIG. 15(C) shows the results of quantification of image. As a result, Fc-A22p and Fc-TPP11 inhibited VEGF165A-induced angiogenesis in living mice. Particularly, it was shown that Fc-TPP11 more effectively inhibited angiogenesis compared to Fc-A22p.

Figure 16A:
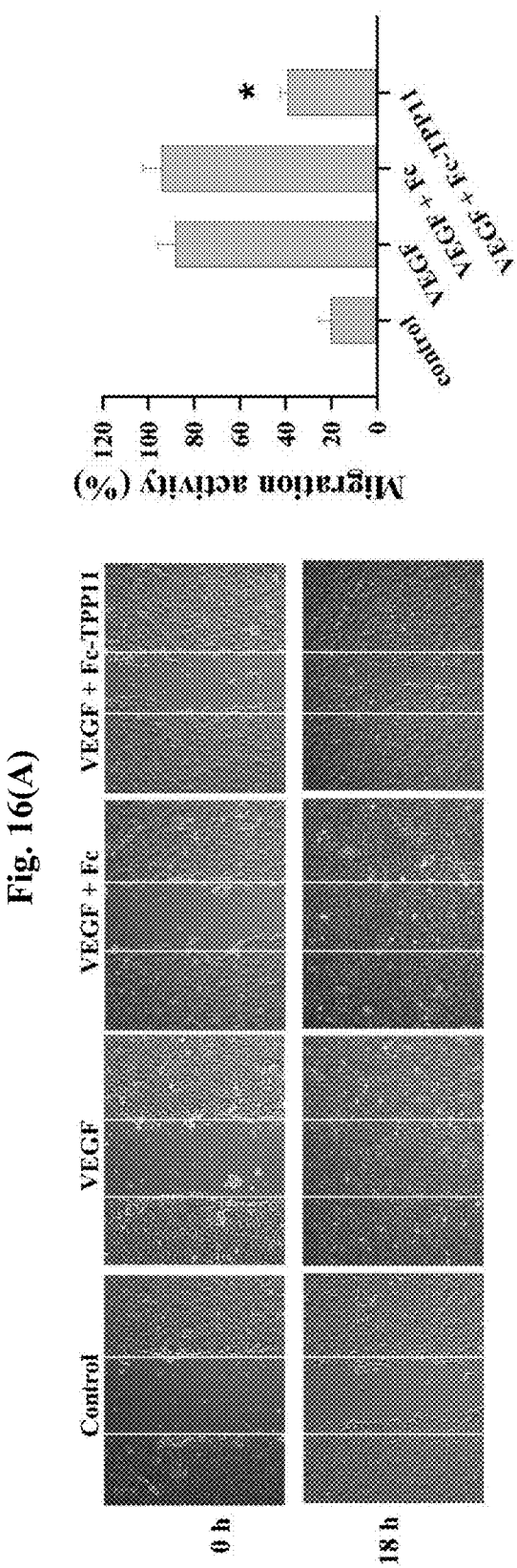
Figure 16B:
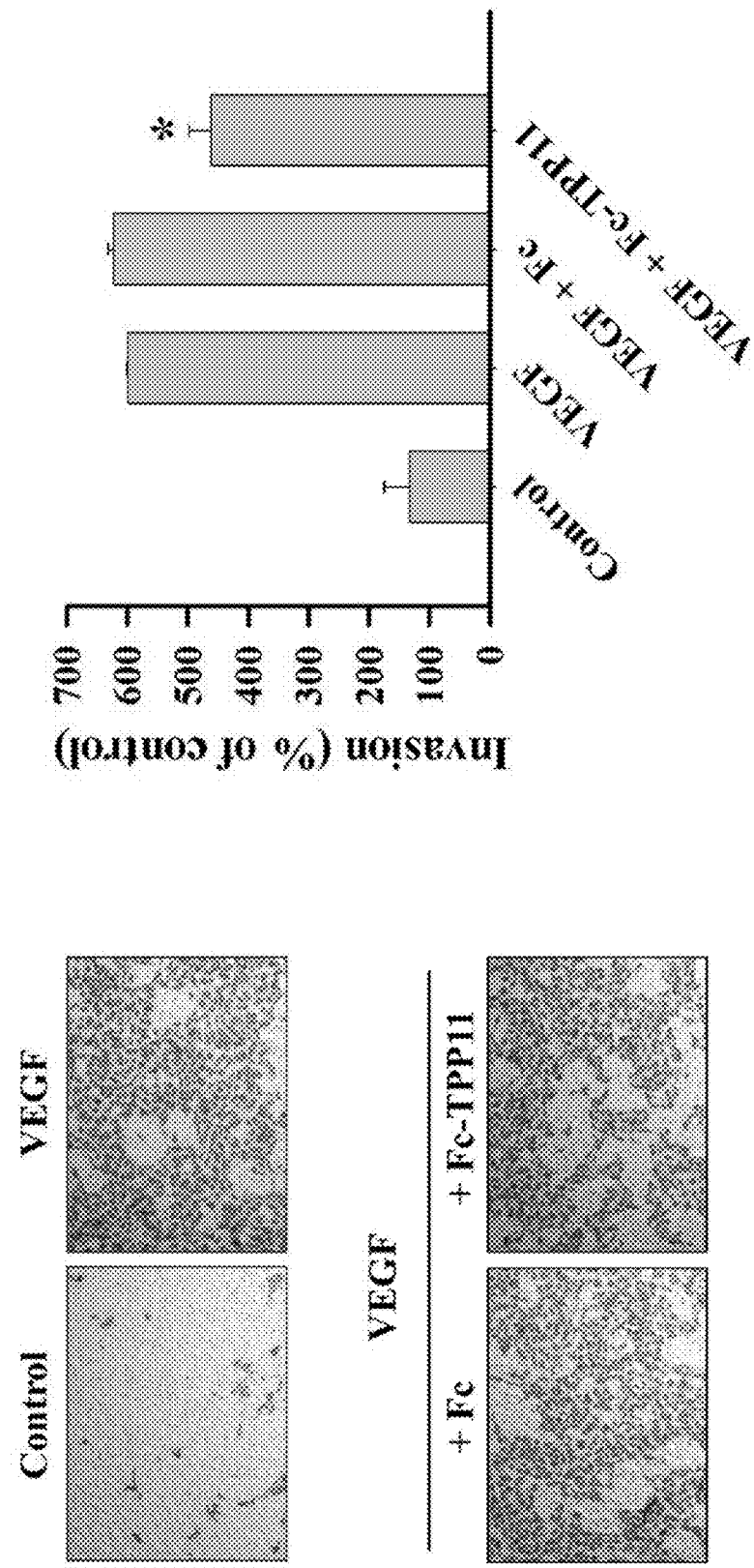

FIGS. 16(A) and 16(B) show the results of measuring the inhibitory activity of Fc-TPP11 against VEGF165A-mediated migration and invasion of vascular endothelial cells.

FIG. 16(A) shows the results of a wound healing assay performed to examine whether Fc-TPP11 inhibits VEGF165A-induced migration of vascular endothelial cells. The control VEGF165A increased the migration activity of vascular endothelial cells, and Fc-TPP11 inhibited the migration activity of vascular endothelial cells, unlike Fc.

FIG. 16(B) shows the results of a Transwell assay performed to examine whether Fc-TPP11 inhibits VEGF165A-induced invasion of HUVEC cells. Fc-TPP11 inhibited the invasion activity of vascular endothelial cells, unlike the control VEGF165A.

Figure 17A:
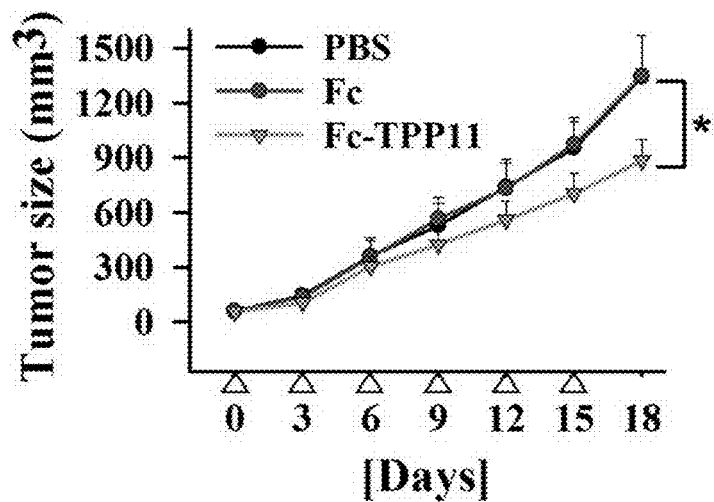
Figure 17B:
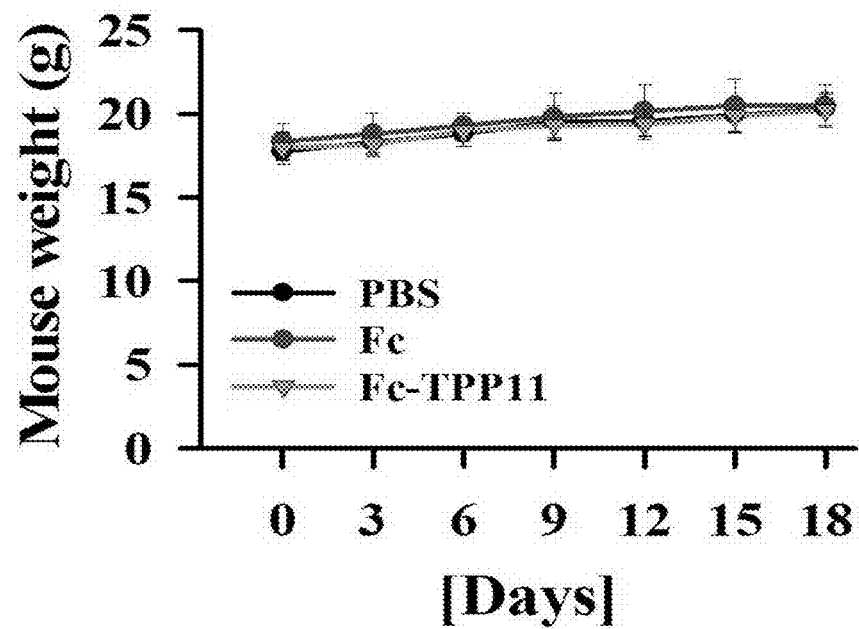

FIGS. 17(A), 17(B), and 17(C) show the results of measuring the tumor growth inhibitory activity of Fc-TPP11 in living mice and the anti-angiogenesis activity of Fc-TPP11 in tumor tissue.

FIG. 17(A) shows the results of a tumor growth inhibitory experiment in nude mouse models, performed to examine whether the anti-angiogenesis activity of Fc-TPP11 actually influences the inhibition of tumor cell growth in vivo. FaDu cells were transplanted into nude mice, and then Fc or Fc-TPP11 was injected into the nude mice. As a result, it was shown that Fc-TPP11 effectively inhibited tumor cell growth, compared to PBS or Fc.

FIG. 17(B) shows the results of measuring the weight of mice in the experiment. There was no significant difference in weight between the mice injected with Fc-TPP11 and the mice injected with PBS or Fc. This indirectly demonstrates that Fc-TPP11 is not toxic to mice.

FIG. 17(C) shows the results of immunohistochemistry for extracted tumors, performed to examine whether the tumor inhibitory activity of Fc-TPP11 in the experiment would be attributable to anti-angiogenesis activity. As a result, in the mice injected with Fc-TPP11, the vascular density of tumor tissue decreased and co-localization of blood vessels and pericytes also decreased, compared to those in the mice injected with the control PBS or Fc.

Figure 18A:
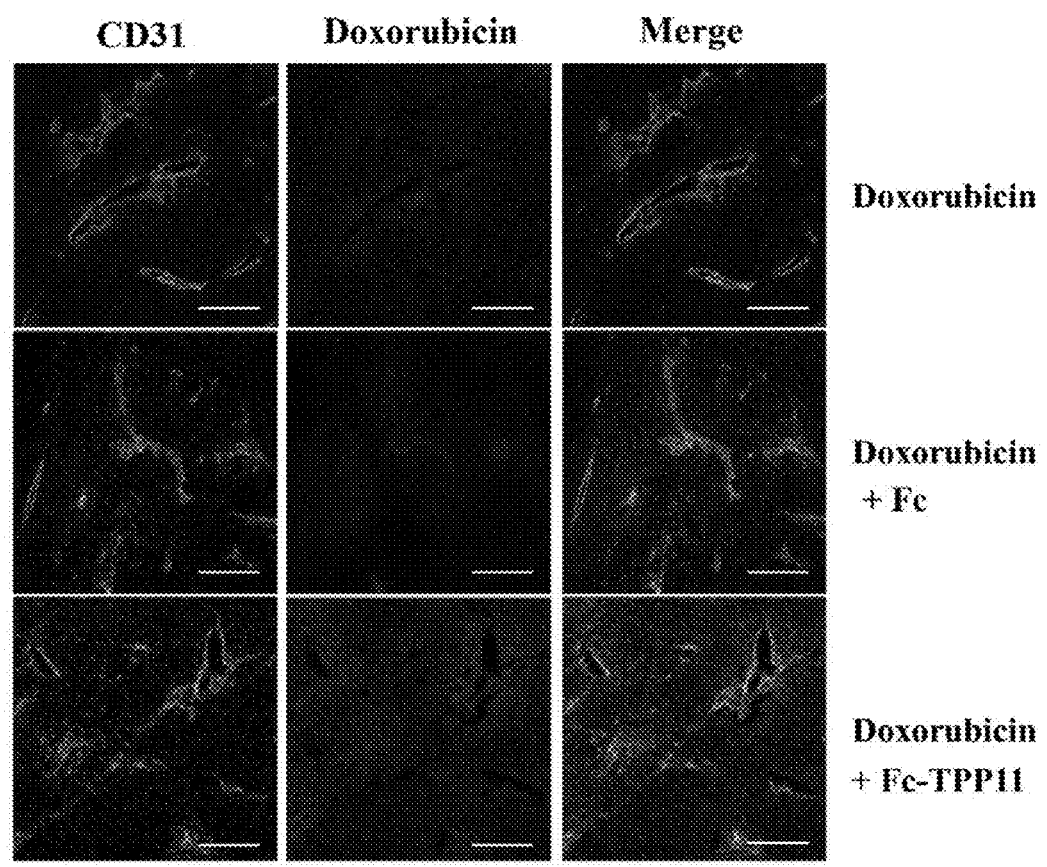

FIG. 18(A) shows the results of immunohistochemistry performed to analyze the tumor-penetrating ability of doxorubicin co-administered with Fc-TPP11. As a result, when doxorubicin was co-administered with Fc-TPP11, the tumor tissue penetration of doxorubicin increased, compared to co-administeration with the control Fc.

Figure 18B:
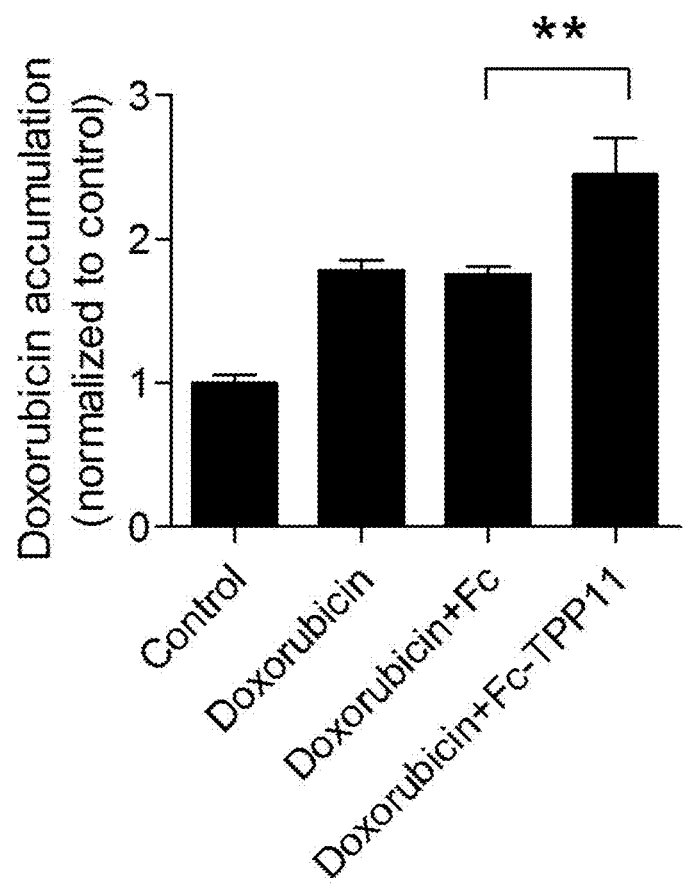

FIG. 18(B) shows the results of quantitatively analyzing the accumulation of doxorubicin in tissue.

Figure 19:
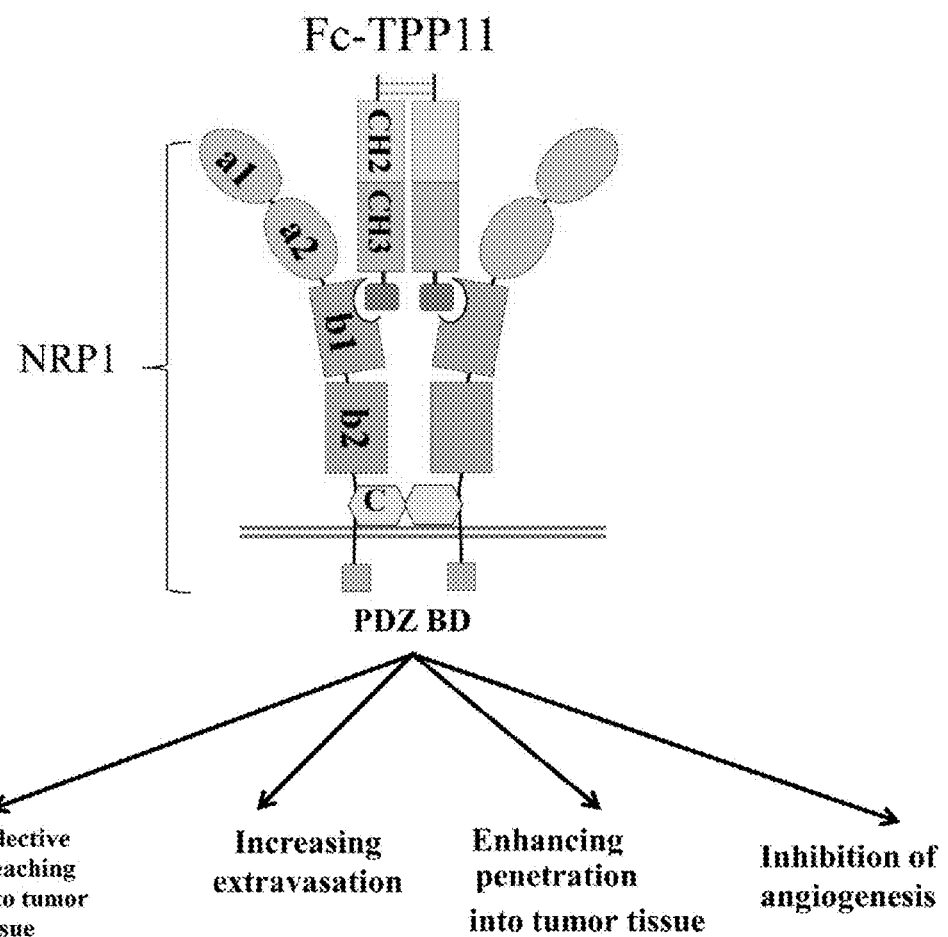

FIG. 19 is a schematic view showing the overall effects of Fc-TPP11. Fc-TPP11 binds to the arginine-binding pocket of the NRP1-b1 domain with high affinity and high specificity without binding to NRP2. Due to this property, Fc-TPP11, when injected in vivo for binding to NRP1, can selectively reach tumor tissue, extravasation thereof into tumor tissue increases, and tumor tissue penetration thereof increases. In addition, Fc-TPP11 binds to NRP1 competitively with the vascular endothelial growth factor VEGF, thereby inhibiting VEGF-induced angiogenesis.

Figure 20:
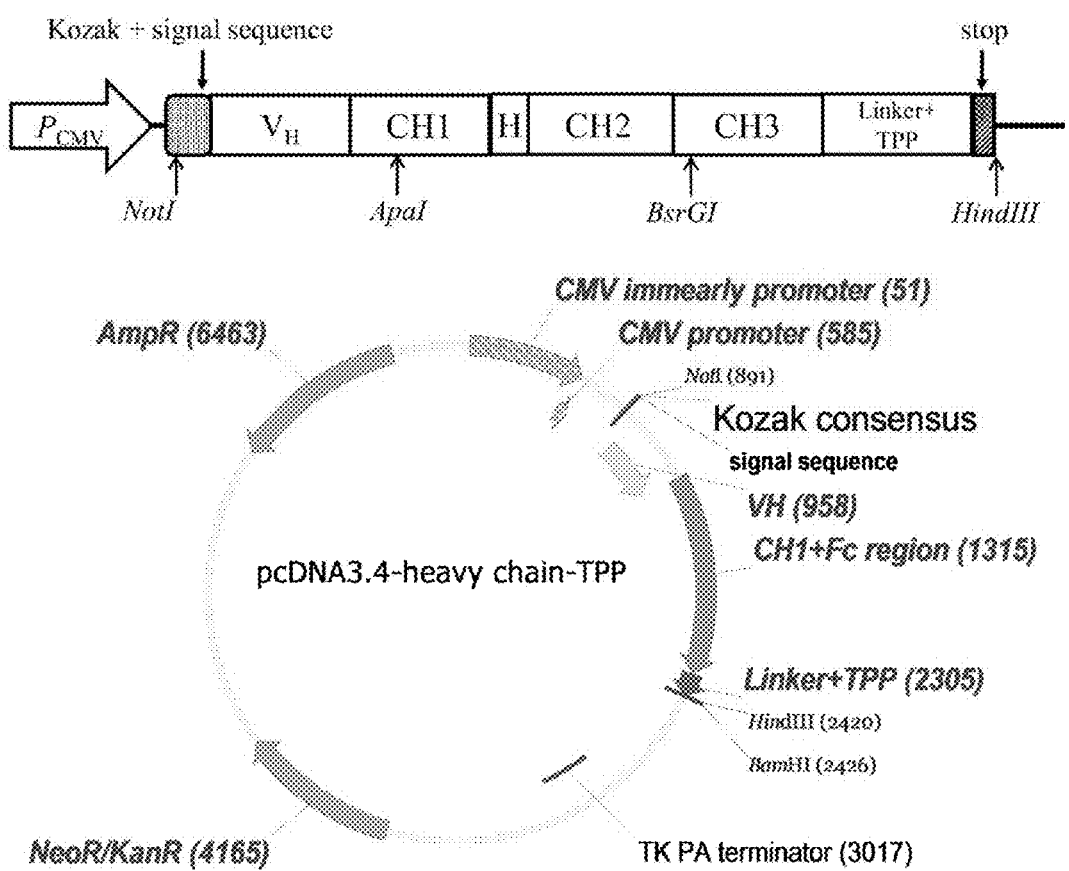

FIG. 20 is an example of a cleavage map of a vector for expressing IgG heavy chain-TPP11.

Figure 21:
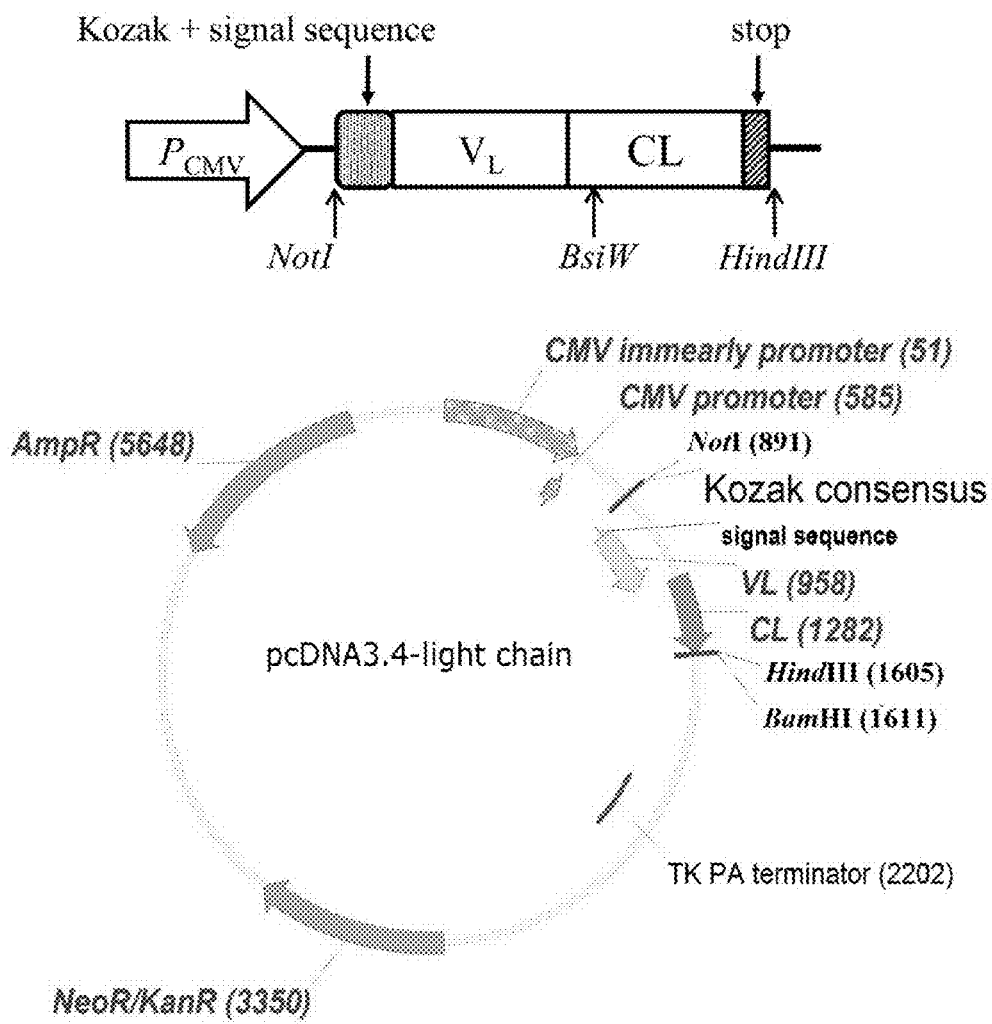
Figure 22A:
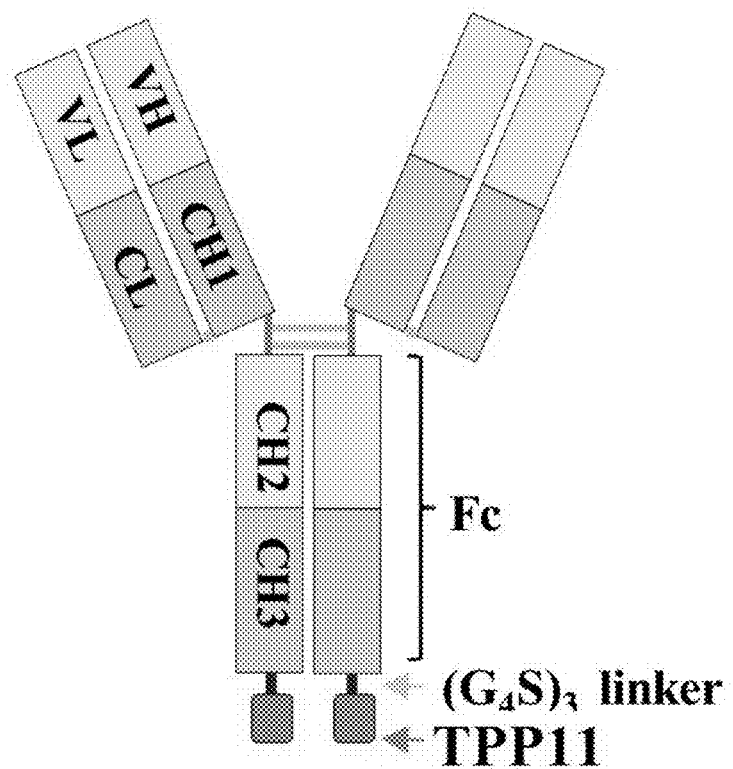

FIG. 21 is an example of a cleavage map of a vector for expressing an IgG light chain. FIG. 22(A) is a schematic view of an antibody constructed by introducing TPP11 into the C-terminus of the heavy chain of the conventional anti-EGFR antibody Cetuximab.

Figure 22B:
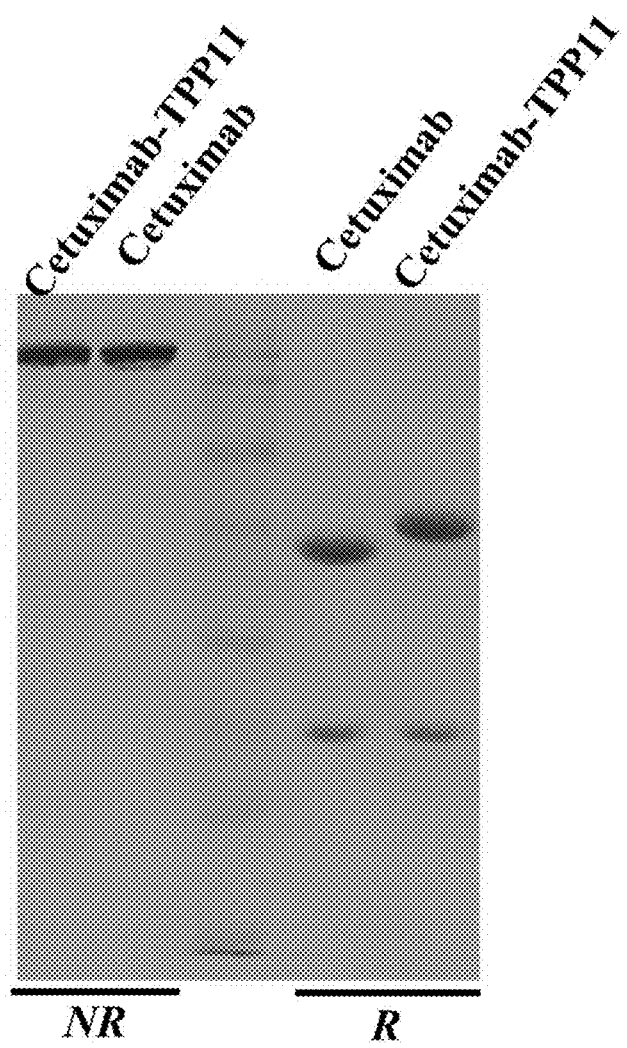

FIG. 22(B) shows the results obtained by co-transforming the antibody into HEK293F cells, transiently expressing and purifying the antibody, and then analyzing the size and purity of the antibody on SDS-PAGE under reducing and non-reducing conditions.

Figure 22C:
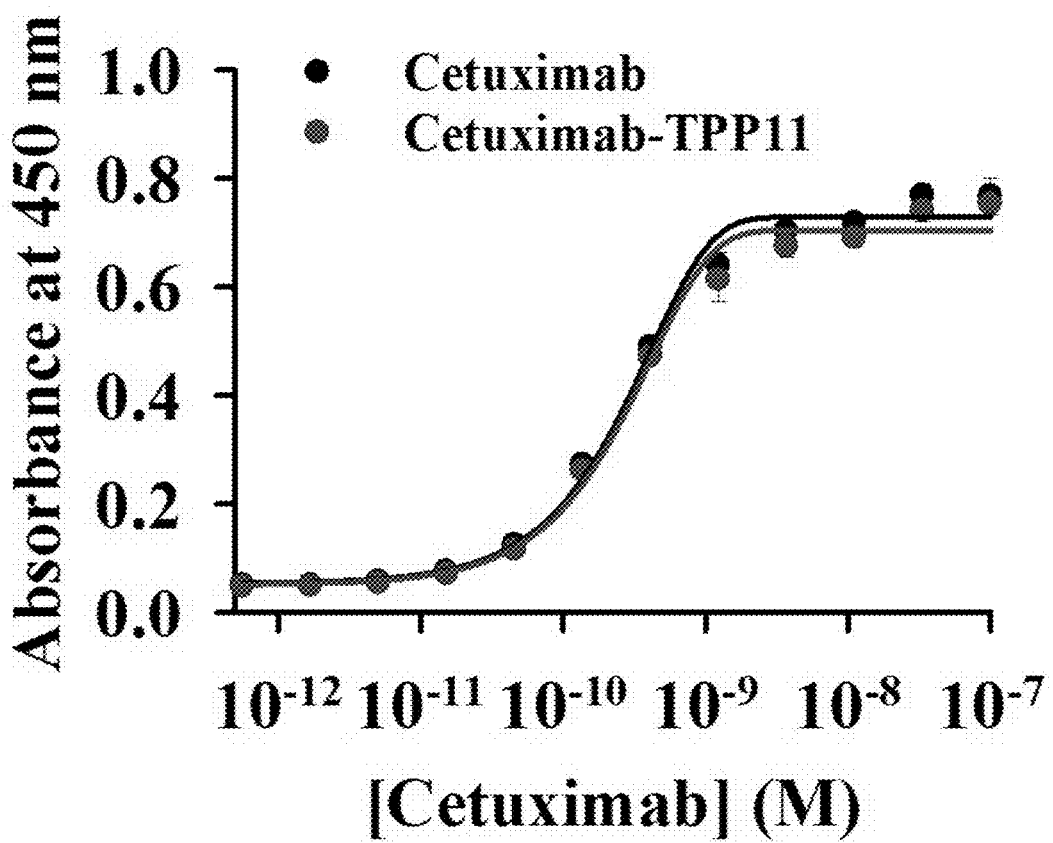

FIG. 22(C) shows the results of ELISA performed to confirm that the binding between Cetuximab-TPP11 does not differ from the binding of Cetuximab to the original antigen EGFR, and shows that TPP11 fusion does not affect the antigen binding ability of the existing antibody.

Figure 23:
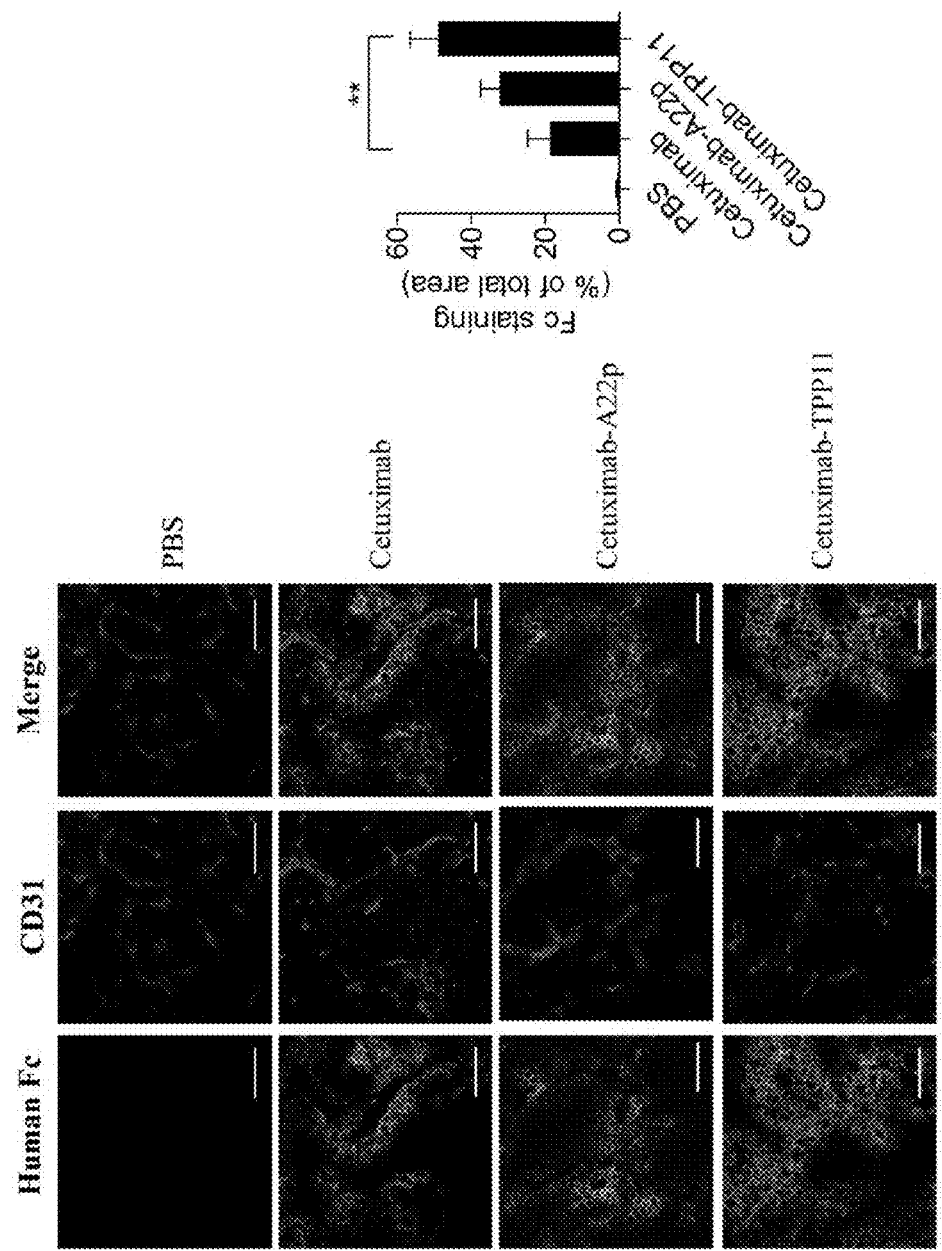

FIG. 23 shows the results of immunohistochemistry performed to examine the ability of Cetuximab-TPP11 to penetrate tumor tissue. Human epidermoid cancer A431 cells expressing EGFR were transplanted into nude mice, after which Cetuximab, Cetuximab-A22p or Cetuximab-TPP11 was injected intravenously into the nude mice, and then tissue penetration thereof was analyzed by double staining with blood vessels (CD31). As a result, it was shown that Cetuximab penetrated only to the periphery of blood vessels, whereas Cetuximab-A22p and Cetuximab-TPP11 penetrated into tissue more distant from blood vessels (left panel). Particularly, Cetuximab-TPP11 more effectively penetrated into tissue compared to Cetuximab-A22p. The penetration was quantified using Image J program (right panel). This suggests that TPP11 has an activity of increasing the tumor tissue accumulation and penetration of a full-length IgG antibody.

BEST MODE FOR CARRYING OUT THE INVENTION

Examples

Hereinafter, the present disclosure will be described in further detail with reference to examples. It will be obvious to a person having ordinary skill in the art that these examples are for illustrative purposes only and are not to be construed to limit the scope of the present disclosure.

Example 1: Construction of Peptide Library that Binds Specifically to Arginine-Binding Pocket of NRP1-b1

Figure 1A:
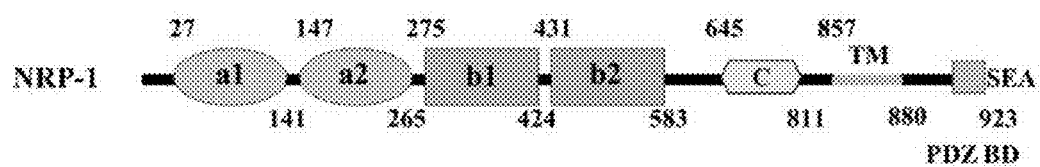
Figure 1B:
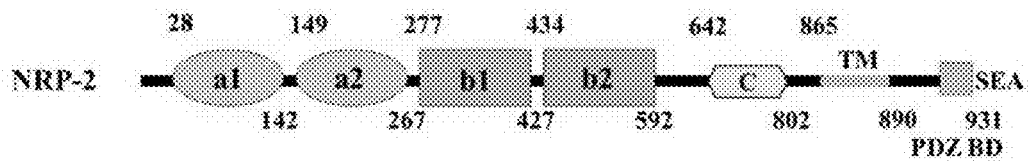
Figure 2:
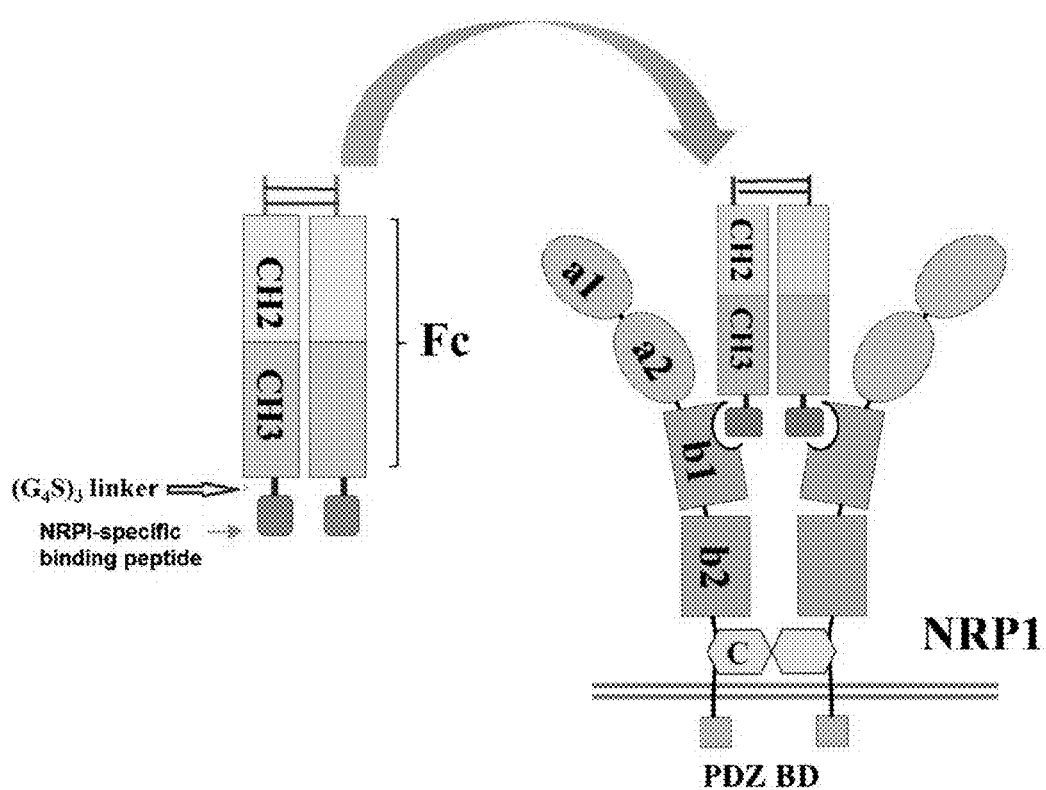

As shown in FIGS. 1(A) and 1(B), neuropilin includes 5 major domains, in which a1 and a2 domains from the N-terminus are classified as CUB domains, to which the semaphorin Ig-like C2 type domain binds. Particularly, this domain forms a complex with plexin to increase the semaphorin-plexin binding affinity. The b1 and b2 domains are classified as FV/VIII domains, and the C-terminus of VEGF or class 3 semaphorin ligands binds thereto. Particularly, in this portion, a site to which heparin can bind is present, and it facilitates the binding of ligands containing many positively charged residues. Further, MAM induces oligomerization, the transmembrane domain (TM) enables neuropilin to be fixed to the cell surface, and in a cytosolic domain, a site capable of binding to a Postsynaptic density 95, Disk large, Zona occludens 1 (PDZ) domain is present. Among these domains, particularly the b1 domain has a pocket-shaped structure to which the C-end rule (CendR) can bind. In fact, when the C-terminal sequences of the ligand Sema3s and the VEGF family, which bind to the arginine-binding pocket of neuropilin b1 as shown in FIG. 2, were analyzed, they all had a sequence corresponding to the C-end rule -R/K-X-X-R/K.

It is known that, among natural ligands that increase tumor tissue penetration by interaction with neuropilin, VEGF165A or Sema3A binds more preferentially to NRP1 than to NRP2. Accordingly, the present inventors anticipated that NRP1 would have a closer connection with tumor tissue penetration than NRP2, and anticipated that NRP1 would be a more preferable target. Thus, as shown in FIG. 2, the present inventors attempted to select Fc-TPP wherein a tumor tissue-penetrating peptide (TPP) that binds specifically to the arginine-binding pocket of NRP1-b1 without binding to NRP2 is fused to the heavy-chain constant region (Fc) of an antibody.

Figure 3:
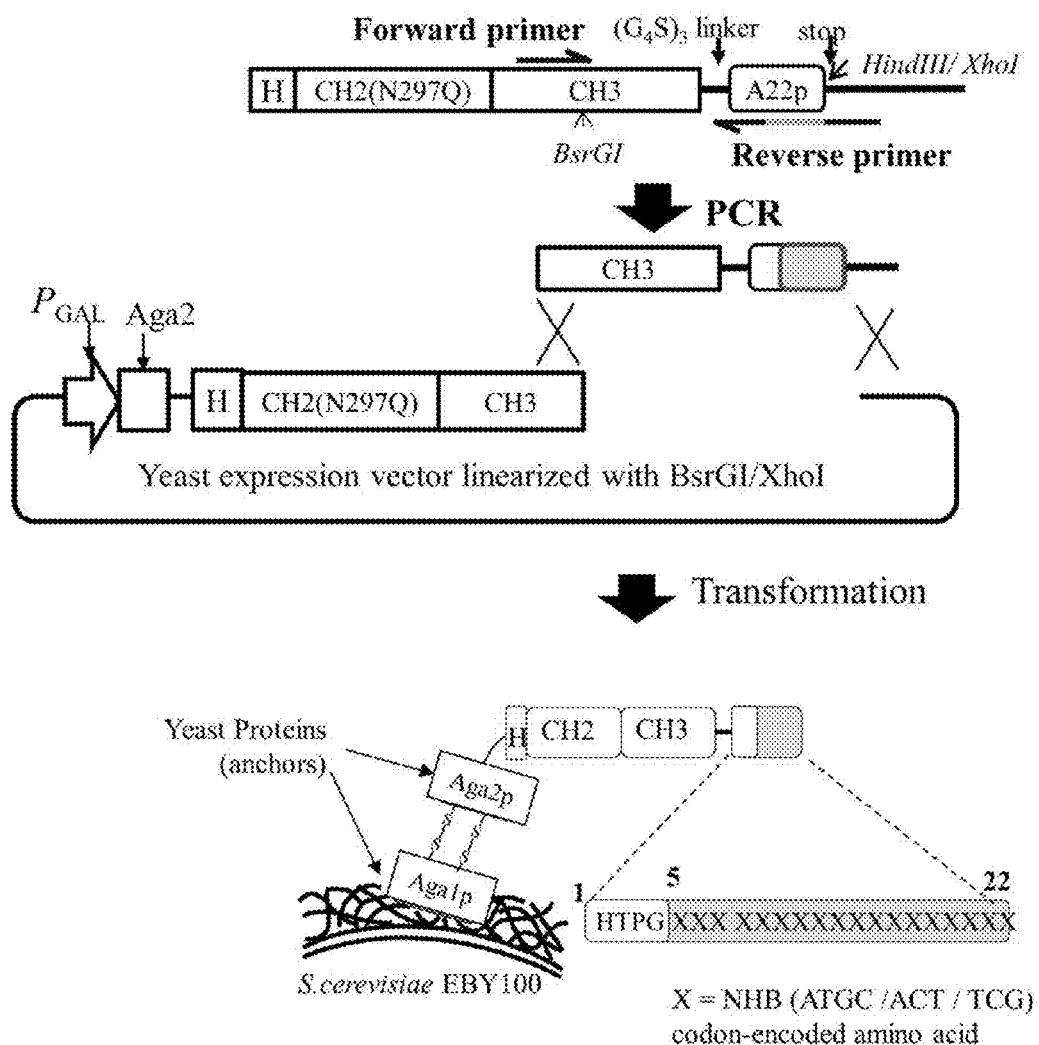

To this end, as shown in FIG. 3, using a conventional A22p sequence (HTPGNSNKWKHLQENKKGRPRR) as a template, a reverse primer comprising the degenerate codon NHB (ATGC/ACT/TCG) was synthesized in which a portion corresponding to 18 residues (5 to 22) from the C-terminus comprises serine, threonine, tyrosine, asparagine, glutamine, histidine, phenylalanine, leucine, isoleucine, valine, alanine, methionine, proline, lysine, asparaginic acid or glutamic acid. Furthermore, a forward primer corresponding to the CH3 region of the antibody heavy-chain constant region (Fc) fragment was synthesized. The forward primer and the reverse primer include the same portion as the sequence of a 50 bp vector so as to enable homologous recombination in yeast cells. The nucleotide sequences of the primers used for construction of the peptide library fused to the antibody heavy-chain constant region (Fc) are shown in Table 1 below.

TABLE 1

Oligonucleotide sequences used for construction of Fc-fusion peptide library

| Name of primer | Oligonucleotide sequence | SEQ ID NOs: |
| --- | --- | --- |
| Forward primer | 5'-CAT CGA GAA AAC CAT CTC CAA AGC CA-3' | SEQ ID NO: 7 |
| Reverse primer | 5'-A AAG TCG ATT TTG TTA CAT CTA CAC TGT TGT TAT CAG ATC TCG AGA AGC TTA TCA VDN VDN VDN VDN VDN VDN VDN VDN VDN VDN VDN VDN VDN VDN VDN VDN VDN VDN VDN VDN TCC AGG AGT ATG TGA TCC-3' | SEQ ID NO: 8 |

Library DNA was prepared by performing PCR. Using a Fc-A22p yeast surface display vector (pCTCON, Colby et al. 2004) as a template and the above-described forward and reverse primers, DNA was amplified. The amplified DNA (a total of 300 μg; 10 μg/transformation) was electroporated 30 times into yeast together with a vector DNA (1 μg/transformation) prepared by treating the Fc yeast surface display vector with BsrGI and XhoI restriction enzymes, thereby constructing a library. Thereafter, as shown in FIG. 3, the library and the vector were connected in the yeast cells by homologous recombination. The size of the peptide library fused to the antibody heavy-chain constant region (Fc) was found to be 2×10$^7$ by measurement of the number of colonies grown in selection medium according to a selectable marker present in the vector, after serial dilution.

Example 2: Selection of Single Clones Binding Specifically to Only NRP1 from Constructed Fc-Peptide Library Obtained by Fusion to Antibody Heavy-Chain Constant Region (Fc)

The target protein NRP1-b1b2 (273-586) and the competitive protein NRP2-b1b2 (275-595) were prepared with a purity of 90% or higher according to conventional methods (BA Appleton et al., 2007). The target protein NRP1-b1b2 was biotinylated as shown in FIG. 4 (EZ-LINK™ Sulfo-NHS-LC-Biotinylation kit (Pierce Inc., USA)).

Figure 4A:
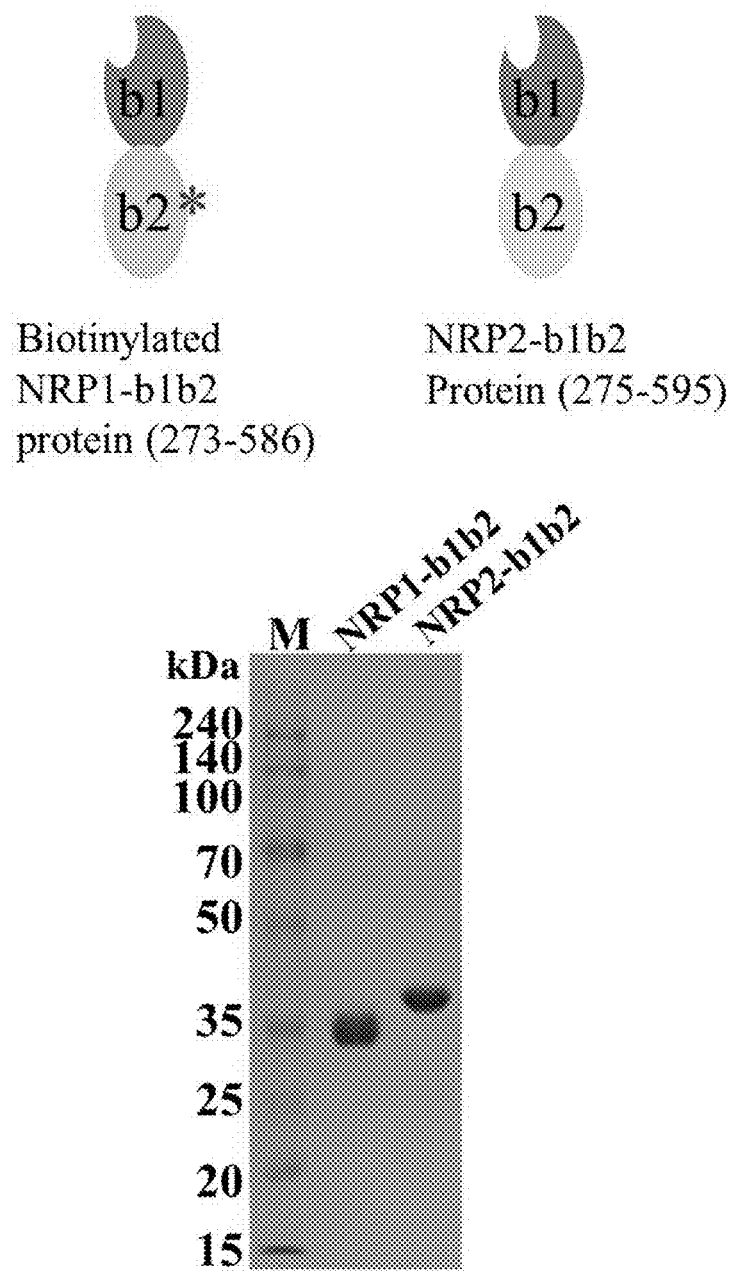

FIG. 4(A) schematically shows the structures of biotinylated neuropilin-1 b1b2 protein and neuropilin-2 b1b2 protein used to select a peptide that binds specifically to NRP1, and also shows the results of expressed and purified SDS-PAGE.

Figure 4B:
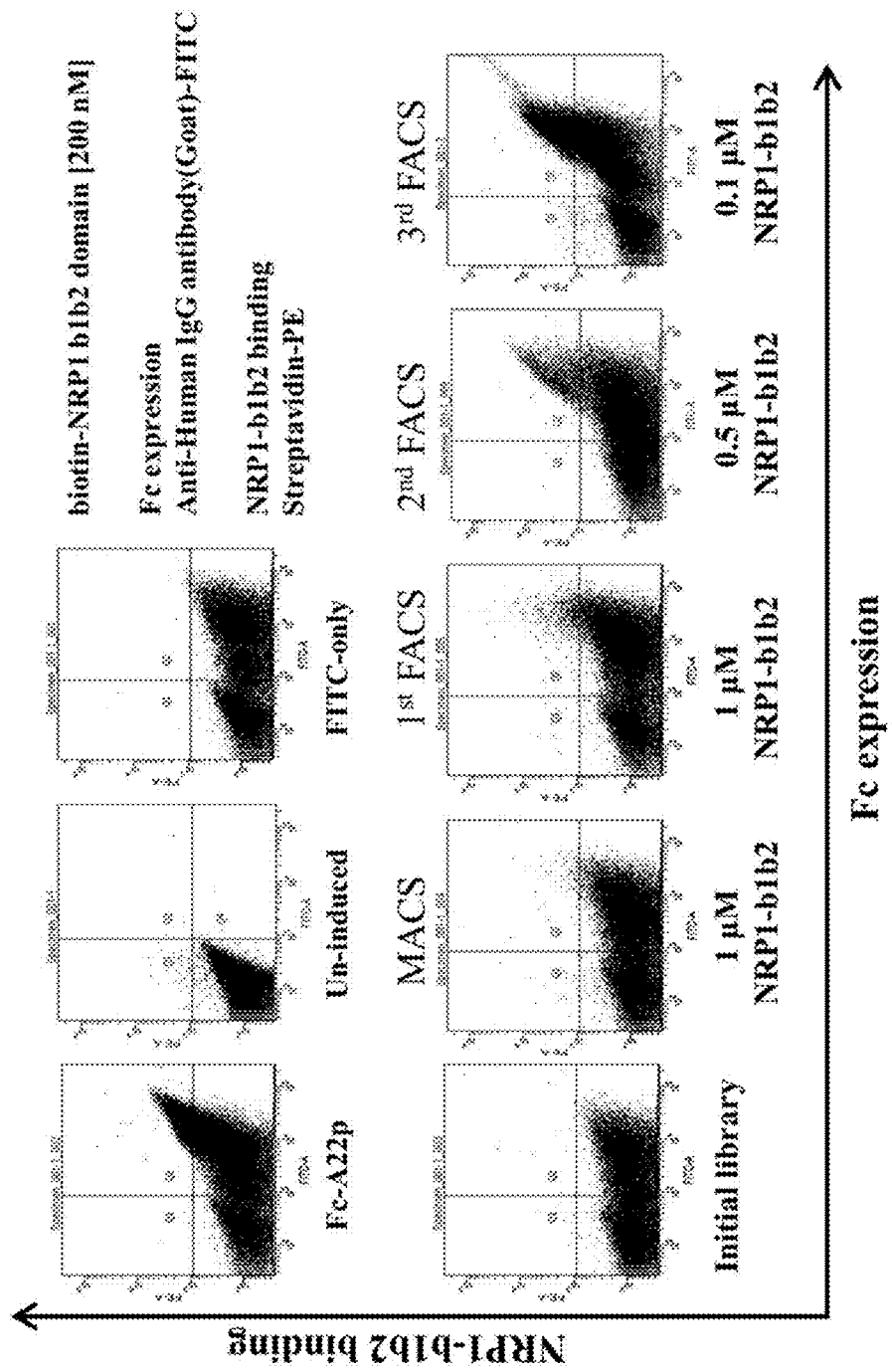

FIG. 4(B) shows the results of FACS performed to analyze a pool in each selection round after MACS and FACS of the constructed library. This can analyze the expression level of the antibody heavy-chain constant region (Fc) and binding to biotinylated NRP1-b1b2, and comparison with cells including Fc-A22p displayed on the yeast cell surface was performed. As MACS add FACS are repeated, the number of clones, which bind to biotinylated NRP1-b1b2 and do not affect the expression of the antibody heavy-chain constant region (Fc), increases.

1 µM biotinylated NRP1-b1b2 was bound to the antibody heavy-chain constant region (Fc)-fused peptide library, displayed on the yeast cell surface, at 37° C. for 1 hour. The antibody heavy-chain constant region (Fc)-fused peptide library, bound to the biotinylated NRP1-b1b2 and displayed on the yeast cell surface, was bound to streptavidin microbeads (Miltenyi Biotec Inc., Germany) at 4° C. for 10 minutes, and then clones bound to the biotinylated NRP1-b1b2 were selected using MACS (magnetic activated cell sorting). Next, 1 µM NRP1-b1b2 was bound to the antibody heavy-chain constant region (Fc)-fused peptide library, displayed on the yeast cell surface, at 37° C. for 1 hour, and then PE-conjugated streptavidin (Streptavidin-R-phycoerythrin conjugate (SA-PE), Invitrogen) and FITC-conjugated anti-Fc antibody (anti-Fc antibody FITC conjugated, goat, (SIGMA-ALDRICH co., USA)) were bound to the library at 4° C. for 20 minutes, after which clones, which express a high level of Fc and have binding affinity for the biotinylated NRP1-b1b2, were selected using FACS (fluorescence activated cell sorting). The second FACS round was performed in the same manner as described above, except that biotinylated NRP1-b1b2 was used at a concentration of 0.5 µM. In addition, in the MACS and FACS processes, non-biotinylated NRP2-b1b2 was used as a competitive protein for biotinylated NRP1-b1b2 at a 10-fold higher concentration, and individual clones that bind to NRP1-b1b2 were selected.

Figure 5B:
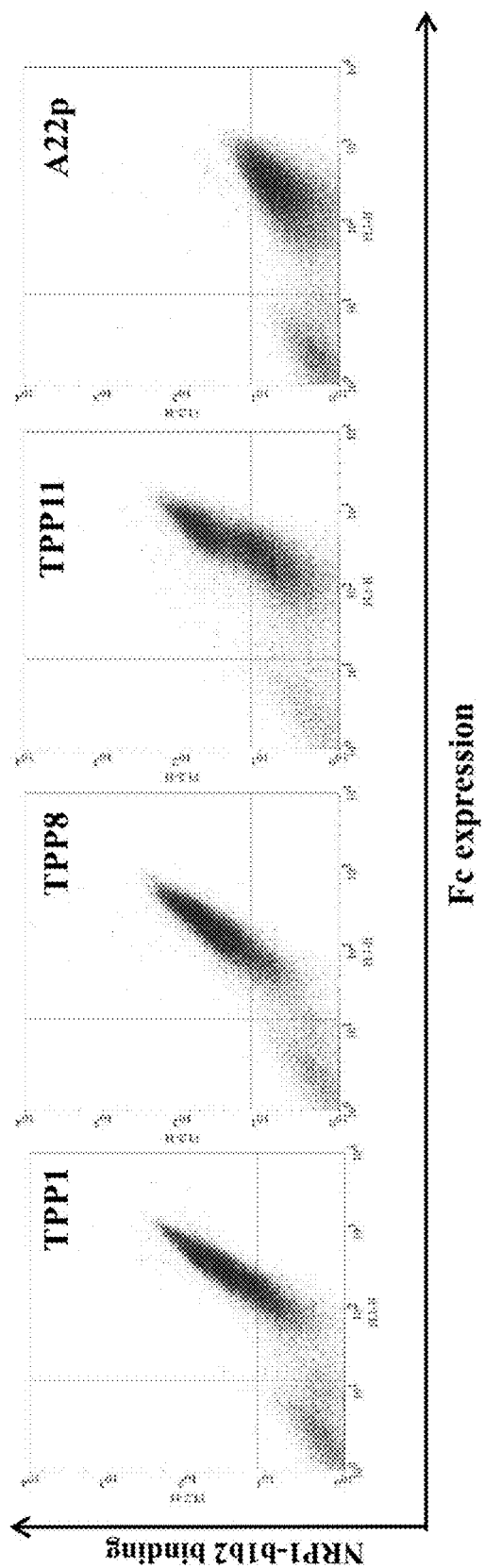
FIG. 5(B) shows the results of FACS analysis performed to analyze binding of Fc-TPP1, Fc-TPP8 and Fc-TPP11, displayed on the yeast cell surface, to 100 nM NRP1-b1b2.

In addition, as shown in FIGS. 5(A) and 5(B), individual clones having high binding affinity for 100 nM biotinylated NRP1-b1b2 were classified according to PE signals by FACS analysis, and clones, named TPP1, TPP8 and TPP11, were selected.

The selected individual clones were recovered from the yeast cells, and the DNA sequences and amino acid sequences thereof were analyzed.

Table 2 below shows the sequences of the selected peptides that bind specifically to NRP1 without binding to NRP2.

TABLE 2

Amino acid sequences and pI of individual clones selected from peptide library fused to antibody heavy-chain constant region (Fc)

| Name of TPP | NRP1-targeting peptide sequence (N-to-C terminus direction) | SEQ ID NOs: |
|---|---|---|
| TPP1 | HTPGNSNQFVLTSTRPPR | SEQ ID NO: 1 |
| TPP8 | HTPGIATRTPR | SEQ ID NO: 2 |
| TPP11 | HTPGNSKPTRTPRR | SEQ ID NO: 3 |

Table 3 shows sequences comprising a linker used when fusing the selected peptide to the antibody heavy-chain constant region.

TABLE 3

Linker-connected, NRP1-targeting peptide sequences

| | Linker-connected, NRP1-targeting peptide sequence (N-to-C terminus direction) | | |
|---|---|---|---|
| Name of TPP | Linker sequence | NRP1-targeting peptide sequence | SEQ ID NOs: |
| TPP1 | GGGGSGGGGSGGGGS | HTPGNSNQFVLTSTRPPR | SEQ ID NO: 4 |
| TPP8 | GGGGSGGGGSGGGGS | HTPGIATRTPR | SEQ ID NO: 5 |
| TPP11 | GGGGSGGGGSGGGGS | HTPGNSKPTRTPRR | SEQ ID NO: 6 |

Example 3: Construction and Expression/Purification of Antibody Heavy-Chain Constant Region Fused with Peptide that Binds Specifically to NRP1

Figure 6:
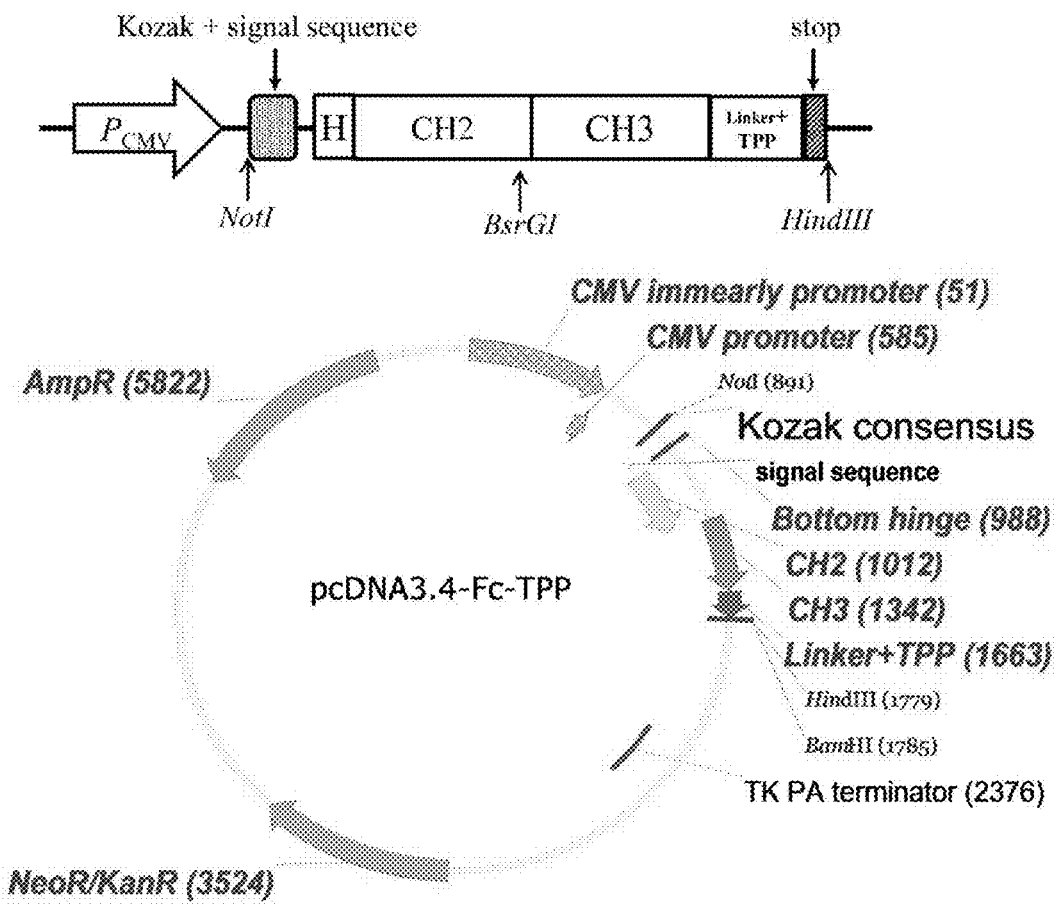
FIG. 6 is an example of a cleavage map of a vector for expressing Fc-TPP1, Fc-TPP8 or Fc-TPP11 protein, which is a Fc-fusion peptide obtained by fusing an antibody heavy-chain constant region with a selected peptide that binds specifically to NRP1, in mammalian cells, HEK293F.

To express the individual clones, selected in Example 2, in mammalian cells, the DNA recovered from the yeast cells was treated with BsrGI and HindII restriction enzymes to obtain the CH3 of the antibody heavy-chain constant region and the peptide portion that binds specifically to NRP1. The obtained DNA fragments were cloned into a pcDNA3.4 vector as shown in FIG. 6.

Using a HEK293-F system (Invitrogen), a plasmid encoding a fusion protein of the antibody heavy-chain constant Fc region and the selected peptide that binds specifically to NRP1 was transiently transfected to express the protein. In a shaking flask, HEK293-F cells (Invitrogen) suspended in serum-free FreeStyle 293 expression medium (Invitrogen) were transfected with a mixture of a plasmid and polyethylenimine (PEI) (Polyscience). For 200 mL transfection in a shaking flask (Corning), HEK293-F cells were seeded in 100 ml of medium at a density of $2.0 \times 10^6$ cells/ml, and incubated at 120 rpm in 8% $CO_2$. Next, a plasmid encoding a fusion protein of the antibody heavy-chain constant region and the selected peptide that binds specifically to NRP1 was diluted in 10 ml of FreeStyle 293 expression medium (Invitrogen) to 250 μg (2.5 μg/ml) and mixed with 10 ml of medium in which 750 μg (7.5 μg/ml) of PEI was diluted. The medium mixture was incubated at room temperature for 10 minutes. Next, the incubated medium mixture was added to 100 ml of the medium containing the seeded cells, and incubated for 4 hours at 120 rpm in 8% $CO_2$, after which the remaining 100 ml of FreeStyle 293 expression medium was added thereto and incubated for 7 days. The supernatant was collected after 7 days.

With reference to standard protocols, protein was purified from the collected cell culture supernatant. Antibody was applied to Protein A Sepharose column (GE healthcare) and washed with PBS (pH 7.4). The antibody was eluted using 0.1 M glycine buffer at pH 3.0, and then the sample was immediately neutralized using 1 M Tris buffer. The eluted antibody fraction was replaced with PBS (pH7.4) using Pierce Dextran Desalting Column (5K MWCO), and then concentrated using MILLIPORE Amicon Ultra (10 MWCO) centrifugal concentrator. The purified fusion protein of the antibody heavy-chain constant region and the selected peptide that binds specifically to NRP1 was quantified based on the absorbance at 280 nm and the extinction coefficient. The purified fusion protein of the antibody heavy-chain constant region and the selected peptide that binds specifically to NRP1 was analyzed on SDS-PAGE under reducing and non-reducing conditions.

FIG. 7(A) schematically shows an Fc-TPP protein wherein the selected peptide that binds specifically to NRP1 is fused to the antibody heavy-chain constant region (Fc). In FIG. 7(A), the antibody heavy-chain constant region (Fc) was constructed starting from the N-terminal hinge so as to maintain two disulfide bonds to easily form a dimer. The Fc-TPP protein has a structure in which the peptide that binds specifically to NRP1 is fused to the terminus of the heavy-chain constant region CH3 of an antibody by a linker peptide of (GGGGS)X3.

FIG. 7(B) shows the results of SDS-PAGE analysis of purified Fc-TPP1, Fc-TPP8 and Fc-TPP11 fusion proteins under reducing and non-reducing conditions. In FIG. 7(B), dimer formation and purity of each clone can be seen on SDS-PAGE.

Table 4 shows the yield of purified Fc-TPP1, Fc-TPP8 or Fc-TPP11 protein that is produced per L of culture. The results obtained in triplicate were statistically processed, and ± indicates standard deviation value. The yield of protein produced did not significantly differ from those of wild-type Fc protein and the control Fc-A22p fusion protein.

TABLE 4

Production yields of Fc-TPP1, Fc-TPP8 and Fc-TPP11 fusion proteins in HEK293 cells

| Name of Clone | Yield (mg/L) |
|---|---|
| Fc | 34.2 ± 4.8 |
| Fc-A22p | 36.1 ± 5.6 |
| Fc-TPP1 | 34.2 ± 3.6 |
| Fc-TPP8 | 32.5 ± 3.2 |
| Fc-TPP11 | 37.6 ± 2.2 |

Example 4: Evaluation of Binding Affinities of Fc-TPP1, Fc-TPP8 and Fc-TPP11 Fusion Proteins for b1b2 Domains of NRP1 and NRP2

The binding affinities of purified Fc-TPP1, Fc-TPP8 and Fc-TPP11 fusion proteins for the b1b2 domains of NRP1 and NRP2 were analyzed by ELISA (Enzyme Linked Immunosorbent Assay).

FIG. 8 shows the results of ELISA performed to measure the NRP1 binding affinities of the control Fc-A22p and the Fc-TPP1, Fc-TPP8 and Fc-TPP11 fusion proteins wherein the selected peptide that binds specifically to NRP1 is fused to the antibody heavy-chain constant region and which are the NRP1-specific individual clones selected from the library. It was shown that the Fc-TPP1, Fc-TPP8 and Fc-TPP11 fusion proteins selected from the library had an about 10-fold to 60-fold higher affinity than Fc-A22p.

To examine specificity for NRP1, the control VEGF165A and Fc, A22p, and each of the fusion proteins wherein the selected peptide that binds specifically to NRP1 is fused to the antibody heavy-chain constant Fc region, was biotinylated using a NHS-biotin kit (SIGMA-ALDRICH co., USA).

1 μg of each of NRP1-b1b2 (273-586) protein, NRP2-b1b2 (275-595) protein and the control group VEGFR2 (46-753) was immobilized in each well of a 96-well EIA/RIA plate (COSTAR Corning In., USA) at room temperature for 1 hour, and then washed three times with 0.1% PBST (0.1% Tween20, pH 7.4, 137 mM NaCl, 10 mM Phosphate, 2.7 mM KCl, SIGMA-ALDRICH co., USA) for 10 minutes. After binding with 5% skim milk (5% Skim milk, pH 7.4, 137 mM NaCl, 10 mM Phosphate, 2.7 mM KCl, SIGMA-ALDRICH co., USA) for 1 hour, each well was washed three times with 0.1% PBST (0.1% Tween20, pH 7.4, 137 mM NaCl, 10 mM Phosphate, 2.7 mM KCl, SIGMA-ALDRICH co., USA) for 10 minutes. Each of biotinylated VEGF165A and Fc as controls, A22p, and the TPP11 peptide and Fc-TPP11, which bind specifically neuropilin-1 as test groups, are bound at a concentration of 10 nM (or 100 nM for the peptide), and then washed three times with 0.1% PBST for 10 minutes. Each well was bound with AP-conjugated anti-biotin antibody (alkaline phosphatase-conjugated anti-biotin mAb, Sigma, USA), and then reacted with pNPP (pnitrophenyl palmitate, SIGMA-ALDRICH co., USA), and the absorbance at 405 nm was measured. Based on the ELISA results obtained by reaction with AP-pNPP for 30 minutes, the binding affinities of the expressed and purified Fc-TPP for the b1b2 domains of NRP1 and NRP2 were evaluated.

As can be seen in FIG. 8(B), it was shown that Fc-TPP11 did bind to NRP1 with high affinity and high specificity.

In addition, in order to further quantitatively analyze the binding affinities of Fc-TPP1, Fc-TPP8 and Fc-TPP11 fusion proteins for NRP1 and NRP2 b1b2 proteins, SPR (surface plasmon resonance) was performed using a Biacore2000 instrument (GE healthcare).

Specifically, each of NRP1 and NRP2 b1b2 proteins was diluted in 10 mM Na-acetate buffer (pH 4.0), and immobilized on a CM5 sensor chip (GE healthcare, USA) at about 1000 response units (RU). For analysis, HBS-EP buffer [10 mM Hepes, 3 mM ethylenediaminetetraacetic acid, and 0.005% surfactant P20 (pH 7.4), GE Healthcare] was used at a flow rate of 30 μl/min, and each of Fc-TPP1, Fc-TPP8 and Fc-TPP11 fusion proteins was used at a concentration of 100 nM to 0.4 nM. As a control, Fc-A22p was used. After binding and dissociation analysis, regeneration of the CM5 chip was performed by flushing buffer (20 mM NaOH, 1M NaCl, pH10.0) at a flow rate of 30 µl/min for 1 minute. Each sensorgram obtained by 3 minutes of binding and 3 minutes of dissociation was normalized and subtracted compared to a blank cell, thereby determining the affinity.

Table 5 below shows the results of analyzing the affinities of the Fc-TPP protein for NRP1-b1b2 and NRP2-b1b2 proteins by SPR (surface plasmon resonance, BIACORE 2000, GE healthcare, USA).

TABLE 5

Analysis of the NRP1-b1b2 and NRP2-b1b2 affinities and specificities of fusion proteins wherein the selected peptide that binds specifically to NRP1 is fused to the antibody heavy-chain constant Fc region

|  | NRP1-b1b2 Binding Affinity (nM) | NRP2-b1b2 Binding Affinity (nM) | Binding Affinity Ratio[($K_D$ for NRP2)/$K_D$ for NRP1)] |
|---|---|---|---|
| Fc-A22p | 63.0 ± 2.1 | 62.0 ± 1.4 | 0.98 |
| Fc-TPP1 | 1.81 ± 0.19 | 1126 ± 51 | 624.8 |
| Fc-TPP8 | 3.85 ± 0.52 | 253.5 ± 33 | 65.8 |
| Fc-TPP11 | 1.65 ± 0.18 | 1555 ± 205 | 945.3 |

As shown in Table 5 above, when Fc-TPP1, Fc-TPP8 and Fc-TPP11 that bind specifically to neuropilin-1 was compared with Fc-A22p that binds to the NRP1 and NRP2 b1b2 proteins, there was an about 60-fold difference in the affinity for NRP1, and the affinity for NRP1 was about 60-fold to 1000-fold higher than the affinity for NRP2. In analysis, at least five sensor grams were analyzed, and the results obtained in triplicate were statistically processed. ± indicates the standard deviation value of independent experiment results.

Example 5: Evaluation of Specific Binding of Fc-TPP1, Fc-TPP8 and Fc-TPP11 Fusion Proteins to NRP1 Displayed on Cell Surface and NRP1-Mediated Endocytosis In an experiment for biological identification of the peptides that binds specifically to NRP1, human umbilical vein endothelial cells (HUVECs) overexpressing NRP1 were used.

FIG. 9 shows the results of confocal microscopic analysis to observe co-localization with NRP1 displayed on the human umbilical vein endothelial cell (HUVEC) surface in order to determine whether the Fc-TPP1, Fc-TPP8 or Fc-TPP11 fusion protein binds specifically to NRP1 displayed on the cell surface.

Specifically, $5×10^4$ HUVEC cells were added to each well of a 24-well plate and incubated in 0.5 ml of EGM2 (Endothelial growth medium, Promocell) medium for 24 hours under the conditions of 5% $CO_2$ and 37° C. When the cells were stabilized, each well was washed with 0.5 ml of PBS, and then incubated in EBM2 (Endothelial basal medium, Promocell) medium for 4 hours, after which each of Fc, Fc-A22p, Fc-TPP1, Fc-TPP8 and Fc-TPP11 was diluted in 0.5 ml of EBM2 medium at 1 µM and incubated for 30 minutes at 4° C. Next, the medium was removed, and each well was washed with cold PBS. Then, the fusion protein wherein the selected peptide that binds specifically to NRP1 is fused to the antibody heavy-chain constant region was stained with FITC (green fluorescence)-labeled antibody (Sigma) that specifically recognizes Fc, and NRP1 was stained with primary antibody (Abcam) that recognizes NRP1 and with TRITC (red fluorescence)-labeled secondary antibody. The nucleus was stained (blue fluorescence) with DAPI and analyzed by confocal microscopy.

As shown in FIG. 9, Fc-A22p, Fc-TPP1, Fc-TPP8 and Fc-TPP11 did bind to NRP1 on the HUVEC cell surface, unlike Fc.

In addition, in order to examine whether the fusion protein of the antibody heavy-chain constant region and the selected peptide that binds specifically to NRP1 can be endocytosed by NRP1, like other neuropilin ligands, endocytosis of the fusion protein and co-localization of the fusion protein with NRP1 were observed by confocal microscopy. Each of Fc, Fc-A22p, Fc-TPP1, Fc-TPP8 and Fc-TPP11 was diluted to 1 µM and incubated for 10 minutes under the conditions of 37° C. and 5% $CO_2$. Then, as described above, Fc and the fusion protein of the antibody heavy-chain constant region and the selected peptide that binds specifically to NRP1 were stained and analyzed by confocal microscopy.

FIG. 10 shows the results of confocal microscopy performed to observe co-localization of the fusion protein (wherein the selected peptide that binds specifically to NRP1 is fused to the antibody heavy-chain constant Fc region) with NRP1 in order to confirm whether the Fc-TPP1, Fc-TPP8 and Fc-TPP11 fusion proteins can be endocytosed by NRP1. As shown in FIG. 10, the control Fc was not endocytosed, and Fc-TPP1, Fc-TPP8 and Fc-TPP11 that bind specifically to NRP1 were more endocytosed than Fc-A22p that binds to NRP1 and NRP2, indicating that these fusion proteins more co-localize with NRP1. This suggests that Fc-TPP1, Fc-TPP8 and Fc-TPP11 can be endocytosed specifically by NRP1.

Example 6: Evaluation of Enhanced Cell Penetration Ability of Fc-TPP1, Fc-TPP8 and Fc-TPP11 Fusion Proteins (1) Western Blot Analysis to Examine the Biological Mechanisms of Fc-TPP1, Fc-TPP8 and Fc-TPP11 Fusion Proteins in HUVECs It is known that semaphorin 3A or VEGF165A enhances vascular permeability using NRP1 as a co-receptor. In this procedure, changes occur, such as a decrease in vascular endothelial (VD) cadherin, phosphorylation, or the like. Namely, VE-cadherin or epithelial (E)-cadherin is an adhesion factor forming the intercellular space between endothelial cells or between epithelial cells, and a decrease in such molecules densifies the intercellular space to interfere with material movement.

In an experimental method that can indirectly demonstrate an increase in vascular permeability, a change in VE-cadherin was analyzed by Western blot analysis. Specifically, $5×10^5$ HUVEC cells were seeded into each well of a 6-well plate and incubated for 24 hours, and then treated with 0.1 µM of the fusion protein of the antibody heavy-chain constant Fc region and the selected peptide that binds specifically to NRP1, for 10 minutes, followed by Western blot analysis. After SDS-PAGE, the gel was transferred to a PVDF membrane, and detection was performed using primary antibodies (SantaCruz) that recognize VE-cadherin and β-actin and using HRP-conjugated secondary antibody (SantaCruz), and analysis was performed using ImageQuant LAS4000 mini (GE Healthcare).

FIG. 11(A) shows the results of Western blot analysis performed to examine the biological mechanisms of Fc-TPP1, Fc-TPP8 and Fc-TPP11 fusion proteins in HUVEC. As shown in FIG. 11(A), in the case of the control VEGF165A and Fc-A22p, a decrease in VE-cadherin was observed, unlike the case of Fc. In the case of Fc-TPP8 and Fc-TPP11 specific for NRP1, a decrease in VE-cadherin was also observed. However, in the case of Fc-TPP1, a decrease in VE-cadherin was insignificant. In the case of Fc-A22p, VE-cadherin significantly decreased upon treatment with 1 µM of Fc-A22p. In the case of Fc-TPP8 and Fc-TPP11 that bind specifically to NRP1 with high affinity, a significant decrease in VE-cadherin was observed even at 0.1 µM, which is 10-fold lower than that of Fc-A22p. Among them, Fc-TPP11 was observed to most effectively induce a decrease in VE-cadherin.

(2) Transwell Assay to Examine the Abilities of Fc-TPP1, Fc-TPP8 and Fc-TPP11 Fusion Proteins to Penetrate Vascular Endothelial Cells Based on the experimental results as described above, in order to examine whether the fusion proteins have an improved ability to penetrate vascular endothelial cells, the Fc-TPP1, Fc-TPP8 and Fc-TPP11 fusion proteins were subjected to a transwell assay.

Specifically, $5 \times 10^4$ human umbilical vein endothelial cells (HUVECs) were seeded into the upper chamber of a transwell plate (Corning) and incubated in EGM2 for 3 days under the conditions of 37° C. and 5% $CO_2$. Next, the medium was replaced with EBM medium, and the cells were treated with each of about 1.3 nM of the control VEGF165A and 1 µM of each of Fc-A22p, Fc-TPP1, Fc-TPP8 and Fc-TPP11 for 30 minutes. Then, 50 µl of dextran-FITC (Sigma) was added to the upper chamber. After 30 minutes, based on the principle according to which the fluorescent substance would be observed when penetration into the vascular endothelial cells was increased, the medium was sampled from the lower chamber and the fluorescence thereof was measured.

FIG. 11(B) shows the results of Transwell assay performed to confirm whether the peptide binding specifically to NRP1 has an improved ability to penetrate human umbilical vein endothelial cells (HUVEC). As shown in FIG. 11(B), VEGF165A and Fc-A22p had an increased ability to penetrate vascular endothelial cells, and Fc-TPP8 and Fc-TPP11 specific for NRP1 had an increased ability to penetrate vascular endothelial cells, unlike Fc. On the other hand, Fc-TPP1 had a very low ability to penetrate vascular endothelial cells. Taking the results together, it was confirmed that the results shown in FIGS. 11(A) and 11(B) had a close connection with each other, and among the fusion peptides wherein the selected peptide that binds specifically to NRP1 is fused to the antibody heavy-chain constant Fc region, Fc-TPP11 is the most effective tumor-penetrating peptide (TPP) that penetrates tumor tissue by NRP1.

(3) Immunohistochemistry (IHC) Experiment for Examining Enhanced Penetration of Fc-TPP1, Fc-TPP8 and Fc-TPP11 Fusion Proteins in Mouse Models In Examples 6(1) and 6(2) above, it was found in vitro that the fusion protein of the antibody heavy-chain constant Fc region and the selected peptide that binds specifically to NRP1 had an enhanced ability to penetrate vascular endothelial cells. Thus, in order to confirm enhanced penetration of the Fc-TPP1, Fc-TPP8 and Fc-TPP11 fusion proteins in mouse models, an immunohistochemistry (IHC) experiment was performed.

In order to confirm that the Fc-TPP1, Fc-TPP8 and Fc-TPP11 fusion proteins have an enhanced ability to penetrate tumor tissue, $5 \times 10^6$ A431 cells expressing neuropilin-1 were injected subcutaneously into Balb/c nude mice, and after about 9 days, when the tumor volume reaches about 300 to 400 mm³, each of PBS, Fc, Fc-A22p, Fc-TPP1, Fc-TPP8 and Fc-TPP11 was injected intravenously into the mice in an amount of 10 mg/kg. At 15 hours after injection, the tumor was extracted from the mice and subjected to immunohistochemistry. The extracted tumor tissue was sectioned to a thickness of 20 µm by a frozen-section method, and the blood vessels were stained with the primary antibody CD31 antibody (BD Pharmingen) and TRITC (red fluorescence)-labeled secondary antibody that recognizes the same. In addition, to observe the distribution of the Fc-TPP1, Fc-TPP8 and Fc-TPP11 fusion proteins in the tissue, an FITC (green fluorescence)-labeled antibody that recognizes Fc was used.

FIG. 12 shows the results of immunohistochemistry performed to confirm actual tumor tissue penetration of the peptide that binds specifically to NRP1. As shown in FIG. 12, Fc-A22p selectively reached tumor tissue, unlike the control PBS and Fc, and Fc-TPP1 and Fc-TPP11 specific for NRP1 also penetrated tumor tissue. Furthermore, it was shown that Fc-TPP1 and Fc-TPP11 having higher selectivity and affinity for NRP1 than Fc-A22p more effectively penetrated tissue. However, Fc-TPP8 did not penetrate tumor tissue. Since Fc-TPP1 and Fc-TPP11 had high affinity for NRP1, they selectively reached NRP1-expressing tumor tissue. In addition, since Fc-TPP11 had a higher ability to penetrate tumor tissue than Fc-TPP1, it was more broadly distributed in tumor tissue.

(4) Examination of the Enhanced Ability of Fc-TPP1, Fc-TPP8 and Fc-TPP11 Fusion Proteins to Penetrate Cancer Cells In order to examine whether the Fc-TPP1, Fc-TPP8 and Fc-TPP11 fusion proteins also have an enhanced ability to penetrate cancer cells, a change in E-cadherin in human head and neck cancer FaDu cells expressing NRP1 was analyzed by Western blot analysis under the same conditions as described above.

FIG. 13(A) shows the results of Western blot analysis performed to examine a change E-cadherin in human head and neck cancer FaDu cells. As shown in FIG. 13(A), Fc-A22p induced a decrease in E-cadherin. In addition, in the case of NRP1-specific Fc-TPP1, Fc-TPP8 and Fc-TPP11, a decrease in E-cadherin was also observed. Like the in vitro results obtained in Examples 6(1) and 6(2), Fc-TPP11 most effectively induced a decrease in E-cadherin.

(5) Ex Vivo Tumor Penetration Assay to Examine Tumor Penetration in Cancer Cells Additionally, in order to examine whether Fc-TPP alleviates the intracellular space between epithelial cells to penetrate tumor tissue even in the absence of blood vessels, an ex vivo tumor penetration assay was performed. In an experimental method, $5 \times 10^6$ FaDu cells were injected subcutaneously into Balb/c nude mice (Nara Biotec, 4-week old, female), and after about 10 days, when the tumor volume reached about 300 to 400 mm³, the tumor tissue was extracted. The extracted tumor tissue was washed with MEM medium containing 1% BSA (Welgene), and then incubated with 3 µM of each of the control PBS and Fc and the test sample Fc-TPP11 for 2 hours and 30 minutes under the conditions of 37° C. and 5% $CO_2$. The incubated tissue was washed twice with 1% BSA-containing MEM medium for 10 minutes each time, fixed with 4% para-formaldehyde, and then subjected to immunohistochemistry. The tumor tissue was sectioned to a thickness of 20 µm by a frozen-section method, and stained with FITC (green fluorescence)-labeled antibody recognizing Fc in order to observe Fc and Fc-TPP11.

FIG. 13(B) shows the results of the ex vivo tumor penetration assay performed to examine whether Fc-TPP11 can penetrate tumor tissue due to NRP1-mediated tumor tissue penetration activity independently of convection caused by blood flow. As shown in FIG. 13(B), it was observed that the control Fc did not penetrate tumor tissue, whereas Fc-TPP11 did bind to tumor tissue even in the absence of blood vessels. This indicates that Fc-TPP11 allows NRP1 to reduce E-cadherin to thereby regulate the intercellular space in epithelial tissue so that Fc-TPP11 has the ability to penetrate tumor tissue.

Example 7: Evaluation of Competitive Binding of TPP11 Peptide and VEGF165A to NRP1-b1b2

In order to evaluate competitive binding of the TPP11 peptide, which binds specifically to NRP1 without binding to NRP2, and VEGF165A and a RPARPAR peptide, known to bind to the arginine-binding pocket of the NRP1-b1 domain, competitive ELISA was performed.

Specifically, binding NRP1-b1b2 (273-586) protein to each well of a 96-well EIA/RIA plate or a 96-well EIA/RIA black plate (COSTAR Corning In., USA) at room temperature for hour, is followed by washing three times with 0.1% PBST (0.1% Tween20, pH 7.4, 137 mM NaCl, 10 mM Phosphate, 2.7 mM KCl, SIGMA-ALDRICH co., USA) for 10 minutes. After binding with 5% skim milk (5% Skim milk, pH 7.4, 137 mM NaCl, 10 mM Phosphate, 2.7 mM KCl, SIGMA-ALDRICH co., USA) for 1 hour, each well was washed three times with 0.1% PBST (0.1% Tween20, pH 7.4, 137 mM NaCl, 10 mM Phosphate, 2.7 mM KCl, SIGMA-ALDRICH co., USA) for 10 minutes. A mixture of Fc-A22p (50 nM) and Fc-TPP1, and a mixture of Fc-TPP11 (3 nM) and VEGF165A (25 nM to 0.02 nM), were prepared, and each mixture was allowed to bind to the NRP1-b1b2 protein. Then, each mixture was incubated with AP-conjugated anti-human antibody (alkaline phosphatase-conjugated anti-human mAb, Sigma, USA), and then reacted with pNPP (p-nitrophenyl palmitate, SIGMA-ALDRICH co., USA), and the absorbance at 405 nm was measured. The ELISA results indicated that Fc-TPP1 and Fc-TPP11 did bind to NRP1-b1b2 competitively with VEGF165A.

FIG. 14(A) shows the results of analyzing whether or not Fc-A22p, Fc-TPP1 and Fc-TPP11 would bind to NRP1 competitively with VEGF165A. It was shown that a portion of NRP1, to which Fc-TPP1, Fc-TPP11 and Fc-A22p did bind, overlapped a portion of NRP1 to which VEGF165A did bind. In addition, it was shown that Fc-TPP1 and Fc-TPP11 had high affinity for NRP1. This suggests that the position at which Fc-TPP1 and Fc-TPP11 bind to NRP1-b1b2 is the arginine-binding pocket to which VEGF165A binds.

FIG. 14(B) shows the results of evaluating the competitive binding of VEGF165A and RPARPAR peptide, known to bind to the arginine-binding pocket of the NRP1-b1 domain, and the TPP11 peptide to NRP2. It was shown that the TPP11 peptide, a small peptide, inhibited the binding of the RPARPAR peptide and VEGF165 to NRP1. This demonstrates that TPP11 binds to the arginine-binding pocket of NRP1-b1.

Example 8: Evaluation of Anti-Angiogenesis Activity of Fc-TPP11

(1) Tube Formation Assay to Examine the Ability of Fc-TPP11 to Inhibit Tube Formation in HUVECs VEGF165A is known to inhibit angiogenesis using NRP1 as a co-receptor. Based on this, as a method capable of observing angiogenesis in vitro, a tube formation assay was performed. In an experimental method, 50 µl of ECMatrix was added to a 96-well plate and polymerized at 37° C. for 2 hours. After 2 hours, HUVEC cells were suspended in EBM2 medium, mixed with VEGF165A (20 ng/ml), Fc or Fc-TPP11 (1 µM), plated on the ECMatrix at a density of $1\times10^4$ cells per well, and incubated for 8 hours. The incubated cells were imaged with a microscope.

FIG. 15(A) shows the results of the tube formation assay performed to examine the ability to inhibit tube formation. As shown in FIG. 15(A), tube formation increased in the cells treated with VEGF165A alone, and Fc-TPP11 inhibited tube formation, unlike Fc.

(2) In Vivo Matrigel Plug Assay to Examine the Anti-Angiogenesis Activity of Fc-TPP11

Additionally, in order to examine anti-angiogenesis activity in vivo, a matrigel plug assay was performed. In an experimental method, each of 6-8-week-old Balb/c nude mice was injected subcutaneously with $7.5\times10^6$ A431 cells, 200 µg of Fc, Fc-A22p or Fc-TPP11, and 0.4 ml of Matrigel (BD Biosciences). After 8 days, the matrigel plug was extracted, imaged (FIG. 15(B)), and then sectioned to a thickness of 20 µm by a frozen-section method, and subjected to immunohistochemistry. The blood vessels were stained with the primary antibody CD31 and a TRITC (red fluorescence)-labeled secondary antibody recognizing the same, and the density of the blood vessels was measured. FIG. 15(C) shows results indicating that Fc-TPP11 could inhibit VEGF165A-induced angiogenesis in living mice.

(3) Wound Healing Assay to Examine the Inhibitory Activity of Fc-TPP11 Against Migration of Vascular Endothelial Cells In addition to the results obtained in Examples 8(1) and 8(2), in order to examine the inhibitory activity of Fc-TPP11 against VEGF165A-induced migration of vascular endothelial cells, a wound healing assay was performed. In an experimental method, $5\times10^5$ HUVEC cells were seeded into each well of a 6-well plate, and then incubated in 0.5% serum EBM2 medium containing 1 µg/ml mitomycin c for 1 hour until the cells were saturated (95% or more) in the plate. The dish bottom was linearly rubbed with a yellow tip to make injury lines having a uniform width. Then, the cells were washed with PBS such that the cells were detached from the bottom. After removal of PBS, medium was added slowly to the HUVEC cells. The cells were treated with 0 or 20 ng/ml of VEGF165A, treated with each of Fc and Fc-TPP11 (1 µM), and then incubated under the conditions of 37° C. and 5% $CO_2$. The cells were imaged with a microscope (Primo vert, Carl Zeiss co., Germany) at 0 hour and 18 hours, and the distance between both ends, measured with a computer program (AxioVision LE, Carl Zeiss co., Germany) included in the microscope, was statistically processed.

FIG. 16(A) shows the results of a wound healing assay performed to examine whether Fc-TPP11 inhibits VEGF165A-induced migration of vascular endothelial cells. The control VEGF165A increased the migration activity of vascular endothelial cells, and Fc-TPP11 inhibited the migration activity of vascular endothelial cells, unlike Fc. This suggests that Fc-TPP11 binds specifically to neuropilin-1 to inhibit the binding of VEGF165A to the arginine-binding pocket of NRP1-b1 to thereby inhibit the migration activity of vascular endothelial cells by VEGF165A.

(4) Transwell Assay to Examine the Inhibitory Activity of Fc-TPP11 Against Invasion of Vascular Endothelial Cells Additionally, in order to examine the inhibitory activity of Fc-TPP11 against VEGF165A-induced invasion of vascular endothelial cells, a transwell assay was performed. A transwell (Corning Costar, USA) having a polycarbonate membrane with a 8-mm pore size was used. Matrigel (Corning Costar, USA) was coated on the lower layer surface of the filter at a ratio of 1:10 and polymerized for 2 hours under the conditions of 37° C. and 5% $CO_2$, and then $5×10^4$ HUVEC cells and each of Fc and Fc-TPP11 (1 μM) were seeded in EBM2 medium in the upper layer well. In addition, EBM2 medium containing VEGF165A (20 ng/ml) was added to the lower layer well. Next, the cells were incubated for 12 hours under the conditions of 37° C. and 5% $CO_2$, and then unmoved cells in the upper layer well were removed with cotton, and the cells were fixed with 4% para-formaldehyde. Then, the cells were stained with crystal violet. Moved cells were observed with a microscope and counted.

FIG. 16(B) shows the results of the transwell assay, which indicate that Fc-TPP11 inhibits VEGF165A-induced invasion of HUVEC cells. The control VEGF165A increased the invasion activity of vascular endothelial cells whereas Fc-TPP11 inhibited the invasion activity of vascular endothelial cells. This suggests that Fc-TPP11 binds specifically to the arginine-binding pocket of NRP1-b1 to inhibit the binding of VEGF165A to NRP1 so that Fc-TPP11 inhibits the invasion activity of vascular endothelial cells by VEGF165A.

Example 9: In Vivo Evaluation of Inhibitory Activity of Fc-TPP11 Against Tumor Growth and Angiogenesis In Example 8, the anti-angiogenesis of Fc-TPP11 was confirmed. Thus, in order to examine whether Fc-TPP11 has tumor growth inhibitory activity resulting from anti-angiogenesis activity in mouse models, each of Balb/c nude mice was injected subcutaneously with $5×10^6$ FaDu cells, and then injected with Fc-TPP11. Specifically, about 5 days after transplantation of the cells, when the tumor volume reached about 60 $mm^3$, 20 mg/kg of each of Fc and Fc-TPP11 was injected intravenously into each mouse six times at 3-day intervals (N=6).

As shown in FIG. 17(A), Fc-TPP11 inhibited cancer cell growth, unlike the control PBS and Fc. Furthermore, as shown in FIG. 17(B), Fc-TPP11 showed no difference in the mouse weight from the case of PBS and Fc, indicating that Fc-TPP11 is not toxic.

FIG. 17(C) shows the results of performing immunohistochemistry (IHC) of the tumor extracted in the above-described experiment, on the assumption that the tumor growth inhibitory activity of Fc-TPP11 as shown in FIG. 17(A) is attributable to the anti-angiogenesis activity thereof. Angiogenic blood vessels were stained with CD31 antibody, and pericytes surrounding the blood vessels were stained with α-SMA, followed by observation with a confocal microscope. As a result, the density of blood vessels in the tumor tissue of the mice injected with Fc-TPP11 decreased compared to that in the mice injected with the control PBS or Fc, and thus co-localization between the blood vessels and the pericytes decreased. This suggests that Fc-TPP11 inhibits VEGF165A-induced angiogenesis which is produced from tumors.

Taking the above-described experimental results together, as shown in FIG. 19, it was confirmed that the fusion protein (Fc-TPP), wherein the selected peptide that binds specifically to NRP1 without binding to NRP2 is fused to the antibody heavy-chain constant Fc region, shows signaling tendencies such as a decrease in VE-cadherin or E-cadherin, even when it binds specifically to NRP1. In addition, it was shown that when the peptide that binds specifically to NRP1 was present alone, it did not induce significant NRP1 signaling, but when the peptide was present as the Fc-TPP fusion protein that is a bivalently bound form, it effectively induced signaling. This suggests that the fusion protein, wherein the peptide that binds specifically to NRP1 is fused to the antibody heavy-chain constant Fc region, binds bivalently to NRP1 to induce NRP1 signaling, thereby exhibiting effective biological activity. Furthermore, the Fc-TPP fusion protein specific for NRP1 binds to NRP1 competitively with VEGF165A to thereby inhibit VEGF165A-induced angiogenesis, indicating that it has an activity of inhibiting tumor growth in vivo. Moreover, Fc-TPP11 obtained by fusing TPP11 among the selected peptides was most effective in tumor penetration.

Example 10: Evaluation of Enhanced Tumor Tissue Accumulation and Penetration of Small-Molecule Drug Co-Administered with Fc-TPP11

In order to examine tumor tissue penetration of a small-molecule drug co-administered with the Fc-TPP11 constructed in the above-described experiment, immunohistochemistry was performed. Specifically, each of Balb/c nude mice was injected subcutaneously with $5×10^6$ FaDu cells, and after about 15 days, when the tumor volume reached about 300 to 400 $mm^3$, 10 mg/kg of the anticancer drug doxorubicin and 2.5 mg/kg of each of PBS, Fc and Fc-TPP11 were injected intravenously into each mouse. At 1 hour after injection, the mouse heart was perfused with PBS and perfused with 4% para-formaldehyde to fix tissue. Next, the tumor tissue was extracted and subjected to immunohistochemistry. The extracted tumor was sectioned to a thickness of 20 μm by a frozen-section method, and the blood vessels were stained with the primary antibody CD31 (BD Pharmingen) and a FITC (green fluorescence)-labeled secondary antibody recognizing the same. It was observed that doxorubicin distributed in the tissue showed red fluorescence by itself.

FIG. 18(A) shows the results of immunohistochemistry (IHC) performed to examine tumor tissue penetration of doxorubicin co-administered with Fc-TPP11. As can be seen therein, in the FaDu cancer cell tissue, little or no red fluorescence was observed in the case of doxorubicin, whereas doxorubicin co-administered with Fc-TPP11 penetrated the tissue more distinct from the blood vessels, compared to doxorubicin alone. In addition, it was observed that co-administration of doxorubicin and the control Fc had no effect on penetration.

FIG. 18(B) shows the results obtained by homogenizing the extracted tumor tissue and measuring the fluorescence value of doxorubicin in the tumor tissue in order to quantitatively determine the accumulation of doxorubicin in the tissue. According to the same method as that used for FIG. 18(A), doxorubicin and each of PBS, Fc and Fc-TPP11 were injected intravenously into mice, and the mouse heart was perfused with PBS, and the tumor tissue was extracted. The extracted tissue was lysed in 1 ml of lysis buffer containing 1% SDS (sodium dodecyl sulfate) and 1 mM sulfuric acid. Then, a 1:1 mixture of chloroform and isopropyl alcohol was mixed with the lysed tissue at a ratio of 2:1 and then frozen at −80° C. Then, the tissue was thawed at 37° C. and centrifuged, and the fluorescence (Excitation 485 nm/emission 528 nm) of the supernatant was measured to quantify the amount of doxorubicin penetrated.

The above-described results indicate that the tumor-penetrating peptide that binds specifically to NRP1 may generally be applied to various small-molecule drugs.

Example 11: Construction and Production of TPP11-Fused Full-Length Antibody (mAb-TPP11)

In Examples 7 and 8, it was found in vitro and in vivo that the fusion protein of the antibody heavy-chain constant Fc region and the selected peptide that binds specifically to NRP1 has an enhanced ability to penetrate vascular endothelial cells. Thus, in order to verify the effect of the peptide that binds specifically to NRP1 in mouse models, the anti-EGFR antibody Cetuximab which is an antibody for treatment of solid tumors was selected as a model antibody for a peptide that binds specifically to mAb-NRP1. To construct Cetuximab-TPP11, in the vector for producing the fusion protein of the TPP11 peptide and the antibody heavy-chain constant region (Fc) as described in Example 3 above, the TPP11-fused DNA in the antibody heavy-chain constant region CH3 obtained by treatment with BsrGI and HindII restriction enzyme was substituted into a vector encoding a wild-type Cetuxmab heavy-chain. FIG. 20 is a schematic view of the constructed Cetuxmab heavy chain-TPP11, and FIG. 21 shows a vector encoding the light-chain of wild-type Cetuximab.

FIG. 22(A) is a schematic view of cetuximab-TPP11 which is a TPP11 peptide-fused full-length IgG monoclonal antibody. Expression and purification of the antibody was performed in HEK293F according to the method described in Example 3, and the purity of the antibody was analyzed by SDS-PAGE. FIG. 22(B) shows the results obtained by co-transforming the antibody into HEK293F cells, transiently expressing and purifying the antibody, and then analyzing the size and purity of the antibody on SDS-PAGE under reducing and non-reducing conditions.

Table 6 below the yield of the purified TPP11-fused antibody produced per L of culture. The results obtained in triplicate were statistically processed, and ± indicates standard deviation value. The yield of the produced protein (Cetuximab-TPP11) did not significantly differ from that of wild-type protein (Cetuximab).

TABLE 6

Comparison of expression/purification yield of TPP11 peptide-fused antibody with wild-type antibody

| Name of Clone | Yield (mg/L) |
|---|---|
| Cetuximab | 39.9 ± 6.2 |
| Cetuximab-TPP11 | 40.2 ± 5.0 |

FIG. 22(C) shows the results of ELISA performed to compare the EGFR binding affinity of TPP11-fused Cetuximab-TPP11 with that of wild-type antibody (Cetuximab) as described in Example 4 above. It was shown that, even when the TPP11 was fused to Cetuximab, it did not affect the binding affinity of Cetuximab to the antigen EGFR.

Example 12: Evaluation of Enhanced Tissue Penetration Ability of Cetuximab-TPP11 Antibody In order to evaluate tumor tissue penetration of the TPP11 peptide-fusion antibody constructed in the above-described experiment, each of Balb/c nude mice was injected subcutaneously with $5 \times 10^6$ FaDu cells, and after about 9 days, when the tumor volume reached about 300 to 400 $mm^3$, 1.25 mg/kg of PBS, Cetuximab and Cetuximab-TPP11 was injected intravenously into each mouse. At 3 hours after injection, the tumor was extracted from the mice and subjected to immunohistochemistry. The tissue was stained and observed in the same manner as described in Example 6.

FIG. 23 shows the results of immunohistochemistry (IHC) performed to evaluate tumor tissue penetration of TPP11 peptide-fused Cetuximab. As can be seen therein, in the case of Cetuximab, green fluorescence was observed around the blood vessels in the FaDu cancer cell tissue, whereas TPP11-fused Cetuximab-TPP11 penetrated the tissue more distant from the blood vessels, compared to Cetuximab. To quantify this penetration, ImageJ program was used. Particularly, TPP11-fused Cetuximab-TPP11 having higher binding affinity for NRP1 more effectively penetrated the tissue compared to Cetuximab-A22p. The above-described results indicate that the tumor-penetrating peptide that binds specifically to NRP1 may generally be applied to various monoclonal antibodies that recognize various antigens.

The invention claimed is:

1. A peptide comprising the amino acid sequence selected from the group consisting of SEQ ID NO: 1 to SEQ ID NO: 3.

2. The peptide of claim 1, wherein the peptide has tumor tissue-penetrating activity and/or anti-angiogenesis activity.

3. The peptide of claim 1, wherein the peptide further comprises a linker peptide.

4. The peptide of claim 3, wherein the linker peptide consists of 1 to 50 amino acids.

5. The peptide of claim 3, wherein the linker peptide comprises the amino acid sequence of (GGGGS)n (SEQ ID NO:10), wherein n is each independently an integer between 1 and 20.

6. The peptide of claim 5, wherein the peptide comprises the amino acid sequence selected from the group consisting of SEQ ID NO: 4 to SEQ ID NO: 6.

7. A fusion protein comprising the peptide of claim 1 and a biologically active agent which is fused to the peptide of claim 1.

8. The fusion protein of claim 7, wherein the biologically active agent is selected from the group consisting of an antibody, antibody fragment, immunoglobulin, peptide, enzyme, growth factor, cytokine, transcription factor, toxin, antigen peptide, hormone, carrier protein, motor function protein, receptor, signaling protein, storage protein, membrane protein, transmembrane protein, internal protein, external protein, secretory protein, viral protein, glycoprotein, cleaved protein, protein complex, and chemically modified protein.

9. The fusion protein of claim 7, wherein the fusion protein binds to neuropilin-1 bivalently or multivalently.

10. The fusion protein of claim 7, wherein the fusion protein further comprises a linker peptide.

11. The fusion protein of claim 8, wherein the antibody fragment is a heavy-chain constant region fragment (Fc), a heavy-chain constant region domain fragment CHI, CH2, or CH3, an antigen binding fragment (Fab), a single-chain variable fragment (scFv), a heavy-chain variable region fragment (VH), a light- chain constant region fragment (CL), or a light-chain variable region fragment (VL).

12. The fusion protein of claim 8, wherein the biologically active agent is a full-length antibody, and the peptide according to claim 1 is fused to the C-terminus of the heavy-chain constant region (Fc) of the full-length antibody.

13. The fusion protein of claim 12, wherein the fusion protein further comprises a linker peptide.

14. The fusion protein of claim 12, wherein the antibody is any one selected from the group consisting of IgG, IgM, IgA, IgD, and IgE.

15. A nanoparticle comprising the peptide of claim 1.

16. A complex comprising a liposome and the peptide of claim 1, which is fused to the liposome.

17. A complex comprising a small-molecule drug and the peptide of claim 1, which is fused to the small-molecule drug.

18. A polynucleotide that encodes the peptide of claim 1.

19. A composition comprising at least one of the following (a)-(e):
   (a) the peptide of claim 1,
   (b) a fusion protein comprising the peptide of claim 1 and a biologically active agent which is fused to the peptide,
   (c) a nanoparticle—peptide complex, said peptide comprising the peptide of claim 1,
   (d) a liposome—peptide complex, said peptide comprising the peptide of claim 1, or
   (e) a small-molecule drug—peptide complex, said peptide comprising the peptide of claim 1.

20. The composition according to claim 19, which is a pharmaceutical composition and comprises a pharmaceutically acceptable carrier.

21. A method for treating a head and neck cancer in a subject in need thereof, comprising administering the composition of claim 19, wherein the cancer is pharyngeal cancer and wherein the biologically active agent and the small-molecule drug are anti- cancer agents.

22. A method for inhibiting angiogenesis in tumor cells that express neuropilin-1 (NRP1) in a subject in need thereof, comprising administering the composition of claim 19, wherein the and the biologically active agent and the small-molecule drug are anti-cancer agents.

* * * * *

SEQUENCE LISTING

```
<160> NUMBER OF SEQ ID NOS: 10

<210> SEQ ID NO 1
<211> LENGTH: 18
<212> TYPE: PRT
<213> ORGANISM: Artificial Sequence
<220> FEATURE:
<223> OTHER INFORMATION: Synthetic construct (TPP1)

<400> SEQUENCE: 1

His Thr Pro Gly Asn Ser Asn Gln Phe Val Leu Thr Ser Thr Arg Pro
1               5                   10                  15

Pro Arg

<210> SEQ ID NO 2
<211> LENGTH: 11
<212> TYPE: PRT
<213> ORGANISM: Artificial Sequence
<220> FEATURE:
```

```
<223> OTHER INFORMATION: Synthetic construct (TPP8)

<400> SEQUENCE: 2

His Thr Pro Gly Ile Ala Thr Arg Thr Pro Arg
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic construct (TPP11)

<400> SEQUENCE: 3

His Thr Pro Gly Asn Ser Lys Pro Thr Arg Thr Pro Arg Arg
1               5                   10

<210> SEQ ID NO 4
<211> LENGTH: 33
<212> TYPE: PRT
<213> ORGANISM: Artificial Sequence
<220> FEATURE:
<223> OTHER INFORMATION: Synthetic construct (TPP1 linked to linker)

<400> SEQUENCE: 4

Gly Gly Gly Gly Ser Gly Gly Gly Ser Gly Gly Gly Gly Ser His
1               5                   10                  15

Thr Pro Gly Asn Ser Asn Gln Phe Val Leu Thr Ser Thr Arg Pro Pro
            20                  25                  30

Arg

<210> SEQ ID NO 5
<211> LENGTH: 26
<212> TYPE: PRT
<213> ORGANISM: Artificial Sequence
<220> FEATURE:
<223> OTHER INFORMATION: Synthetic construct (TPP8 linked to linker)

<400> SEQUENCE: 5

Gly Gly Gly Gly Ser Gly Gly Gly Ser Gly Gly Gly Gly Ser His
1               5                   10                  15

Thr Pro Gly Ile Ala Thr Arg Thr Pro Arg
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct (TPP11 linked to linker)

<400> SEQUENCE: 6

Gly Gly Gly Gly Ser Gly Gly Gly Ser Gly Gly Gly Gly Ser His
1               5                   10                  15

Thr Pro Gly Asn Ser Lys Pro Thr Arg Thr Pro Arg Arg
            20                  25

<210> SEQ ID NO 7
<211> LENGTH: 26
<212> TYPE: DNA
<213> ORGANISM: Artificial Sequence
<220> FEATURE:
<223> OTHER INFORMATION: forward primer

<400> SEQUENCE: 7
```

```
catcgagaaa accatctcca aagcca                                          26

<210> SEQ ID NO 8
<211> LENGTH: 127
<212> TYPE: DNA
<213> ORGANISM: Artificial Sequence
<220> FEATURE:
<221> NAME/KEY: misc_feature
<222> LOCATION: (58), (61), (64), (67), (70), (73), (76), (79), (82),
      (85), (88), (91), (94), (97), (100), (103), (106), (109)
<223> OTHER INFORMATION: a or g or c
<220> FEATURE:
<223> OTHER INFORMATION: reverse primer

<400> SEQUENCE: 8
aaagtcgatt tgttacatc tacactgttg ttatcagatc tcgagaagct tatcavdnvd      60
nvdnvdnvdn vdnvdnvdnv dnvdnvdnvd nvdnvdnvdn vdnvdnvdnt ccaggagtat    120
gtgatcc                                                              127

<210> SEQ ID NO 9
<211> LENGTH: 15
<212> TYPE: PRT
<213> ORGANISM: Artificial Sequence
<220> FEATURE:
<223> OTHER INFORMATION: Synthetic construct (Linker)

<400> SEQUENCE: 9

Gly Gly Gly Gly Ser Gly Gly Gly Gly Ser Gly Gly Gly Gly Ser
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: synthetic linker

<400> SEQUENCE: 10

Gly Gly Gly Gly Ser
1               5
```